US009676772B2

(12) United States Patent
Zajdel et al.

(10) Patent No.: US 9,676,772 B2
(45) Date of Patent: Jun. 13, 2017

(54) PYRROLOQUINOLINE DERIVATIVES AS 5-HT$_6$ ANTAGONISTS, PREPARATION METHOD AND USE THEREOF

(71) Applicants: CENTRE NATIONAL DE LA RECHERCHE SCIENTIFIQUE, Paris (FR); UNIVERSITE DE MONTPELLIER, Montpellier (FR); UNIWERSYTET JAGIELLONSKI, Cracow (PL); INSTYTUT FARMAKOLOGII POLSKIEJ AKADEMII NAUK, Cracow (PL)

(72) Inventors: Pawel Zajdel, Kraków (PL); Katarzyna Grychowska, Kraków (PL); Maciej Pawlowski, Wieliczka (PL); Anna Partyka, Kraków (PL); Anna Wesolowska, Kraków (PL); Andrzej J. Bojarski, Zabierzów (PL); Piotr Popik, Kraków (PL); Tomasz Kos, Kraków (PL); Grzegorz Satala, Kraków (PL); Frederic Lamaty, Montpellier (FR); Evelina Colacino, Montpellier (FR); Jean Martinez, Caux (FR); Gilles Subra, Saint Gély du Fesc (FR); Xavier Bantreil, Aigues-vives (FR)

(73) Assignees: Uniwersyter Jagiellonski, Cracow (PL); Instytut Farmakologii Polskiej Akademii Nauk, Cracow (PL); Centre National De La Recherche Scientifique, Paris (FR); Universite de Montpellier, Montpellier (FR)

( * ) Notice: Subject to any disclaimer, the term of this patent is extended or adjusted under 35 U.S.C. 154(b) by 0 days.

(21) Appl. No.: 14/907,050

(22) PCT Filed: Jul. 25, 2013

(86) PCT No.: PCT/PL2013/000097
§ 371 (c)(1),
(2) Date: Jan. 22, 2016

(87) PCT Pub. No.: WO2015/012704
PCT Pub. Date: Jan. 29, 2015

(65) Prior Publication Data
US 2016/0159790 A1    Jun. 9, 2016

(51) Int. Cl.
*C07D 471/04* (2006.01)
*A61K 31/4745* (2006.01)
*A61K 31/496* (2006.01)
*A61K 31/5377* (2006.01)
*A61K 31/551* (2006.01)

(52) U.S. Cl.
CPC ........ *C07D 471/04* (2013.01); *A61K 31/4745* (2013.01); *A61K 31/496* (2013.01); *A61K 31/5377* (2013.01); *A61K 31/551* (2013.01)

(58) Field of Classification Search
CPC ................. C07D 471/04; A61K 31/4745
See application file for complete search history.

(56) References Cited

U.S. PATENT DOCUMENTS

2003/0232843 A1   12/2003   Cole et al.

FOREIGN PATENT DOCUMENTS

WO      WO 00/12502       3/2000
WO      2008/147812 A2   12/2008

OTHER PUBLICATIONS

Sato et al.; JP 2001286284 A; 2000; SciFinder abstract; Accession No. 2001:752824.*
Benakki, et al., "Microwave-assisted multi-step synthesis of novel pyrrolo-[3,2-c]quinoline", Tetrahedron 64 (2008) 5949-5955.
Bentley, et al., "Investigation of stretching behaviour induced by the selective 5-HT6", British Journal of Pharmacology (1999) 126, 1537-1542.
Berge, "Pharmaceutical Salts", Journal of Pharmaceutical Sciences, Jan. 1977 vol. 66 No. 1.
Bickerton, et al., "Synthesis and Hypotensive Properties of New 4-Aminoquinolines", Journal of Medicinal Chemistry, 1971, vol. 14, No. 11.
Boissier, "A New Method for Rapid Screening of Minor Tranquillizers in Mice", European Journal of Pharmacology 4 (1968) 145-151, North-Holland Publishing Corp. Amsterdam.
Bojarski, "Structure-activity relationship studies of CNS agents, Part 9: 5-HT and 5-HT receptor affinity of some 2- and 3-substituted 1,2,3,4-tetrahydro-beta-", Pharmazie 48 (1993), H:4.
Brown, et al., "Reversible Inhibitors of the gastric (H+/K+)-ATPase. 1.1-Aryl-4-methylpyrrolo[3,2-c]quinolines as Conformationally Restrained Analogues of 4-(Arylamino)quinolines", J. Med. Chem. 1990, 33, 52-533.
Cheng, et al., "Relationship Between the Inhibitino Constant (K1) and the Concentration of Inhibitor which causes 50 per cent inhibition (I50) of an enzymatic reaction", Biomechanical Pharmacology, vol. 22, pp. 3099-3108, Pergamon Press, 1973.
Dawson, "The 5-HT6 Receptor Antagonist SB-271046 Selectively Enhances Excitatory Neurotransmission in the Rat Frontal Cortex and Hippocampus", Neuropsychopharmacology 2001—vol. 25, No. 5, 662-668.

(Continued)

*Primary Examiner* — Timothy Thomas
(74) *Attorney, Agent, or Firm* — KramerAmado P.C.

(57) ABSTRACT

This invention concerns pyrroloquinoline derivatives as antagonists of 5-HT6 receptors, to methods for the preparation of these compounds and to novel intermediates useful for their synthesis. The invention also relates to the uses of such compounds and compositions, particularly their use in administering them to patients to achieve a therapeutic effect in schizophrenia, anxiety, depression, maniac depression, epilepsy, obsessive compulsive disorders, mood disorders, migraine, Alzheimer's disease, age related cognitive decline, mild cognitive impairment, sleep disorders, eating disorders, anorexia, bulimia, panic attacks, attention deficit hyperactivity disorder, attention deficit disorder, Parkinson's disease, Huntington's disease, withdrawal from abuse of cocaine, ethanol, nicotine or benzodiazepines, pain, obesity and type-2 diabetes, functional bowel disorder, Irritable Bowel Syndrome. The compounds have the general formula (XIV), wherein the symbols have the meanings given in the description.

17 Claims, No Drawings

(56) References Cited

OTHER PUBLICATIONS

Dorje, et al., "MR Antagonist binding profiles of five cloned human muscarinic receptor subtypes", J. Pharmacol. Exp. Ther. 256: 727-733.

Dwyer, "Stereospecific Influences in Metal Complexes Containing Optically Active Ligands", J. Am. Chem. Soc. 1964, 86, 590-592.

Gerard, "Immuno-localization of serotonin 5-HT6 receptor-like material in the rat central nervous system", Brain Research 746 (1997) 207-219.

Greengrass, et al., "Binding Characteristics of 3H-Prazosin to Rat Brain alpha-Adrenergic Receptors", European Journal of Pharmacology, 55 (1979) 323-326.

Hannon, et al., "Molecular biology of 5-HT receptors", Behavioural Brain Research 195 (2008) 198-213.

Heal, et al., "Selective 5-HT6 receptor ligands: Progress in the development of a novel pharmacological approach to the treatment of obesity and related metabolic disorders", Pharmacology & Therapeutics 117 (2008) 207-231.

Heidempergher, et al., "Pyrrolo[3,2-c]quinoline derivataives: a new class of kynurenine-3-hydroxylase inhibitors", Il Farmaco 54 (1999) 152-160.

Helissey, et al., "Synthesis and cytotoxic activity of y-methoxy-1H-pyrrolo[3,2-c]-quinoline-6,9-dione and 3-methoxy-1IH-indolo[3,2-c]quinoline-1,4 diones", Eur. J. Med. Chem. 22 (1987) 366-368.

Hirano, et al., "Procognitive 5-HT6 antagonists in the rat forced swimming test: Potential therapeutic utility in mood disorders associatd with Alzheimer's disease", Life Sciences 84 (2009) 558-562.

Hoyer, et al., "Molecular, pharmacological and functional diverty of 5-HT receptors", Pharmacology, Biochemistry and Behavior, 71 (2002) 553-554.

King, "5-HT6 receptor antagonists reverse delay-dependent deficits in novel object discrimination by enhancing consolidation—an effect sensitive to NMDA receptor antagonism", Neuropharmacology 47 (2004) 195-204.

Kohen, et al., "Cloning, Characterization, and Chromosomal Localization of a Human 5-HT6 Serotonin Receptor", Journal of Neurochemistry 1996, 66, 47.

Lopez-Rodriguez, et al., "A Three-Dimensional Pharmacophore Model for t5-Hydroxytryptomine6 (5-HT6) Receptor Antagonists", J. Med. Chem. 2006 (48) 4216-4219.

MacKenzie, et al., "Characterization of the human dopamine D3 receptor expressed in transfected cell lines", European Journal of Pharmacology—Molecular Pharmacology Section, 266 (1994) 79-85.

Martin, et al., "Synthesis and Characterisatiaon of Two Clusters . . . having an Unusual Metal Geometry and Considerable Elongation of the μ6-C—O Bond", J. Chem. Soc., Dalton Trans. 1995 (2741-2748).

Mitchell, "5-HT6 receptors: a novel target for cognitive enhancement", Pharmacology & Therapeutics 108 (2005) 320-333.

Monsma, et al., "Cloning and Expression of a Novel Serotonin Receptor with High Affinity for Tricyclic Psychotropic Drugs", Molecular Pharmacology, 43:320-327.

Paluchowska, et al., "The influence of modifications in imide fragment structure on 5-HT1a and 5-HT7 receptor affinity and in vivo pharmacological properties of some new 1-(m-trifluoromethylphenyl)piperazines", Bioorganic & Medicinal Chemistry 15 (2007) 7116-7125.

Porsolt, et al., "Behavioural Despair in Mice: A Primary Screening Test for Antidepressants", Arch. int. Pharmacodyn Ther. 229, 327-336 (1977).

Pouzet, et al., "Effects of the 5-HT6 receptor antagonist, SB-271046, in animal models for schizophrenia", Pharmacology, Biochemistry and Behavior 71 (2002) 635-643.

Pullagurla, et al., "Possible differences in modes of agonist and antagonist binding at human 5-HT6 receptors", Bioorganic & Medicinal Chemistry Letters 14 (2004) 4569-4573.

Riemer, et al., "Influence of the 5-HT6 Receptor on Acetylcholine Release in the Cortex: Pharmacological Characterization of . . . a Potent and Selective 5-HT6 Receptor Antagonist", J. Med. Chem. 2003 (46) 1273-1276.

Rodefer, et al., "Reversal of Subchronic PCP-Induced Deficits in Attentional Set Shifting in Rats by Sertindole and a 5-HT6 Receptor Antagonist: Comparison Among Antipsychotics", Neuropsychopharmacology (2008) 33, 2657-2666.

Rogers, et al., "5-HT6 receptor antagonists enhance retention of a water maze task in the rat", Psuchopharmacology, (2001) 158: 114-119.

Ruat, et al., "A Novel Rat Serotonin (5-HT6) Receptor: Molecular Cloning, Localization and Stimulation of cAMP Accumulation", Biochemical and Biophysical Research Communications, vol. 193, No. 1993, pp. 268-276.

Schechter, et al., "Meetings", Soc. Neurosci. Meet, 2004, Presentation No. 394.11.

Schoeffter, et al., "5-Hydroxytryptamine receptors with a 5-HT6 receptor-like profile stimulating adenylyl cyclase activity in pig caudate membranes", Naunyn-Schmiedeberg's Arch Pharmacol (1994) 350: 356-360.

Smit, et al., "Regulation of the human histamine H1 receptor stably expressed in Chinese hamster ovary cells", British Journal of Pharmaacaology (1996) 117, 1071-1080.

Stam, et al., "Genomic organisation and functional expression of the gene encoding the human serotonin 5-HT2c receptor", European Journal of Pharmacology Molecular Pharmacology Section 269 (1994) 339-348.

Upton, et al., "5-HT6 Receptor Antagonists as Novel Cognitive Enhancing Agents for Alzheimer's Disease", Neurotherapeutics: The Journal of the American Society for Experimental NeuroTherapeutics, vol. 5, 458-469—Jul. 2008.

Ward, et al., "Localization of Serotonin Subtype 6 Receptor Messenger RNA in the rat brain by in situ Hybridization Histochemistry", Neuroscience vol. 64, No. 4, pp. 1105-1111 (1995).

Wesolowska, et al., "Anxiolytic-like and antidepressant-like effects produced by the selective 5-HT6 receptor antagonist SB-258585 after intrahippocampal administration to rats", Behavioural Pharmacology 2007, 18: 439-446.

Wesolowska, et al., "Effects of the brain-penetrant and selective 5-HT6 receptor antaognist SB-399885 in animal models of anxiety and depression", Neuropharmacology 52 (2007) 1274-1283.

Zajdel, et al., "Quinoline- and isoquinoline-sulfonamide derivatives of LCAP as potent CNS multi-receptor-5-HT1A/5-HT2a/5-HT7 and D2/D3/D4-agents: The synthesis and pharmacological evaluation", Bioorganic & Medicinal Chemistry 20 (2012) 1545-1556.

Zajdel, et al., "The multiobjective based design, synthesis and evaluation of arylsulfonamide/amide deritvaties of aryloxyethyl- and aryltioethyl-piperdines and pyrrolidines as a novel class of potent 5-HT7 receptor antagonists", European Journal of Medicinal Chemistry 56 (2012) 348-360.

* cited by examiner

PYRROLOQUINOLINE DERIVATIVES AS 5-HT$_6$ ANTAGONISTS, PREPARATION METHOD AND USE THEREOF

FIELD OF THE INVENTION

The invention relates to the field of pharmaceutical and organic chemistry, and provides pyrroloquinolone derivatives, formulations and methods.

BACKGROUND ART

Serotonin (5-Hydroxytryptamine; 5-HT) receptors play a critical role in many physiological and behavioral functions in humans and animals (Hannon et al., 2008). These functions are mediated via 15 subtypes of 5-HT receptors (Hoyer et al., 2002). One of the recent additions to the serotonin receptors superfamily constitute 5-HT$_6$ subtype, which via stimulating adenyl cyclase increases the cAMP intracellular level (Ruat et al., 1993; Schoeffter and Weaber, 1994).

The results of the autoradiographic and immunohistochemical studies, as well as mRNA hybridization experiments, revealed that 5-HT$_6$ receptors were almost exclusively found in the central nervous system (CNS), displaying the highest density in the olfactory tubercle, cortex, striatum, nucleus accumbens and hippocampus (Kohen et al., 1996; Gerard et al., 1997; Ward et al., 1995).

Much of the recent interest in the 5-HT$_6$ receptor results from the fact that several psychotropic agents display high affinity for 5-HT$_6$ receptor and show antagonistic properties at these sites (Monsma et al., 1993). These compounds include amitriptyline, clozapine, quetiapine, olanzapine, sertindole. However, they display multitarget profile.

The results of the in vivo tests published so far have indicated that the 5-HT$_6$ antagonists may evoke antidepressant and antianxiolytic responses in the animal models. As it was demonstrated by Wesotowska et al. compound SB-258585 displayed an antidepressant-like effect in the forced swim test in rats and anxiolytic-like effect in the conflict drinking test in rats (Wesotowska and Nikiforuk, 2007a). Other 5-HT$_6$ antagonits, i.e. SB-399885, and SB-271046 also produced antidepressant-like activity in the forced swim test in rats (Hirano et al., 2009). Moreover, SB-399885 showed antianxiety-like effect in the conflict drinking (Vogel) test and an elevated plus maze test performed in rats (Wesotowska and Nikiforuk, 2007b).

The investigation of the potential role of 5-HT$_6$ receptors in schizophrenia, conducted in the standard models of this disorder, revealed that 5-HT$_6$ antagonists do not seem probable to display antipsychotic action (Pouzet et al., 2002). However, such compounds improve learning and memory in animal models, including novel object discrimination (King et al., 2004), Morris water maze learning (Rogers and Hagan, 2001) and attention set shifting (Rodefer et al., 2008). These results suggest that 5-HT$_6$ antagonist might be useful for the treatment of cognitive deficits in schizophrenia and other cognitive disorders such as Alzheimer's disease.

The pharmacological studies of 5-HT$_6$ ligands allowed observing interaction of the 5-HT$_6$ modulators and other brain neurotransmitters, mainly acetylcholine (Ach) and glutamate (Glu). The 5-HT$_6$ receptor antagonists have been shown to increase the acetylcholine transmission (Bentley et al., 1999; Riemer et al., 2003). Other studies have also presented that SB-271046, a 5-HT$_6$ receptor antagonist, increases the level of glutamate in the cortex and hippocampus (Dawson et al., 2001), while application of a 5-HT$_6$ receptor agonist WAY-466 leads to the hippocampal glutamate level decrease (Schechter et al., 2004). Taking into account the role of Ach and Glu in the learning and memory, these results might suggest that 5-HT$_6$ receptors may impact the cognitive processes, which are often disturbed in the affective disorders and neurodegenerative diseases (Mitchell and Neumaier, 2005; Upton et al., 2008).

In the last years, the 5-HT$_6$ receptor agents were reported to reduce the food intake in rats, thus suggesting that the 5-HT$_6$ receptors modulators might be of potential use in the feeding disorders like obesity, anorexia and bulimia (Heal et al., 2008). As the current pharmacological approaches to the obesity treatment are not effective enough, these observations make the 5-HT$_6$ receptors a promising molecular target for a new anti-obesity agents. These seems important, since obesity—characterized by an increase in body fat content resulting in excess body weight above accepted norms—is the most prevalent nutritional disorder in the western world. Importantly, it leads to increased mortality due to increased incidences of diseases such as cardiovascular, digestive, respiratory diseases, and type-2 diabetes.

Concluding, 5-HT$_6$ selective agents have been identified as potentially useful in the treatment or prophylaxis of certain disorders of the central nervous system such as Parkinson's disease, schizophrenia, anxiety depression, maniac depression, obsessive compulsive disorders, mood disorders, Alzheimer's disease, age related cognitive decline, mild cognitive impairment, neurodegenerative disorders characterized by impaired neuronal growth, panic attacks, epilepsy, attention deficit hyperactivity disorder (ADHD), withdraw from drug abuse such as cocaine, ethanol, nicotine and benzodiazepines, and pain. 5-HT$_6$ ligands are also expected to be useful in the treatment or prophylaxis of obesity and type-2 diabetes.

The first selective 5-HT$_6$ receptors ligands were identified by the high throughput screening of the compound libraries, which resulted in the selection of the antagonist I-SB-271046 (Formula (I)). It was the first 5-HT$_6$ receptor agent that entered clinical trials for cognitive impairment in schizophrenia and Alzheimer's disease.

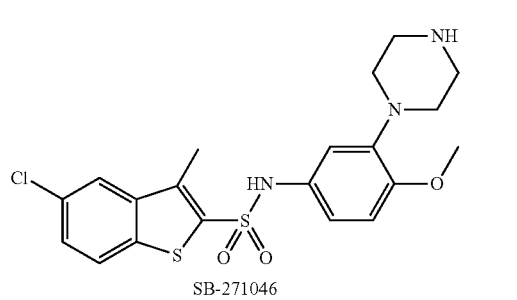

SB-271046

In the same time, a series of tryptamine derivatives based around EMDT was reported as 5-HT$_6$R agonists. In a next move, arylsulfonamide derivatives of indole and indole-like structures were designed. It was found, that compound MS-245 displayed high affinity for 5-HT$_6$ receptors and high selectivity over other monoaminergic receptors (Formulas (II)-(III)). Moreover, an introduction of the sulfonamide moiety switched the functional profile from agonistic to antagonistic one.

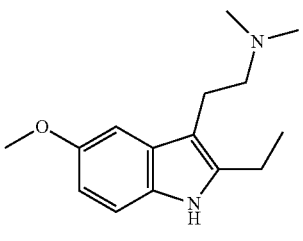
EMDT
II

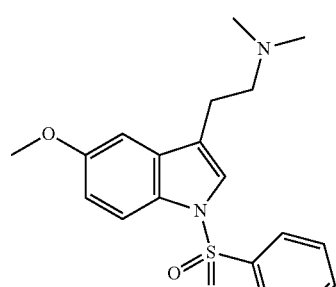
MS-245
III

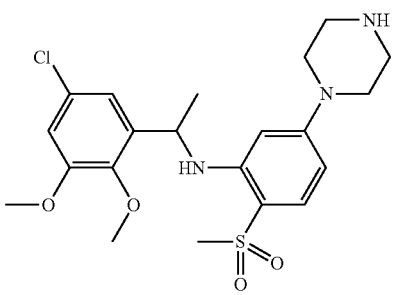
PRX-07034
V

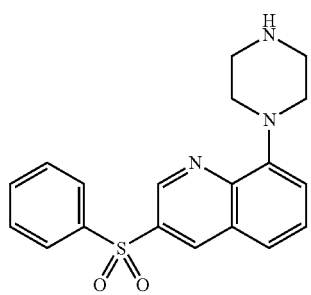
SB-742457
VI

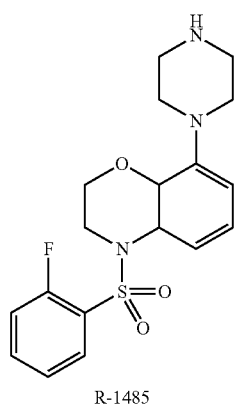
R-1485
VII

Since that time, several 5-HT$_6$ ligands possessing sulfonyl or sulfonamide moiety have been developed. Chemically, they might be divided into two main groups. The first one consists in the indole and indole-like based structures. Among them PF-05212365 is currently under clinical development for the treatment of cognitive deficits in schizophrenia and Alzheimer disease (Formula (IV)).

The second group comprises arylpiperazine derivatives, containing one or more condensed aromatic rings. PRX-07034 belongs to monoarylpiperazine derivatives modified with sulfonyl moiety (Formula (V)). Currently it is investigated under clinical trials for cognition and suppression of the food intake. Other arylpiperazine derivatives with planar aromatic systems, e.g. SB-742457 and R-1485 are the subject of clinical trials for cognitive impairment in schizophrenia and Alzheimer's disease (Formulas (VI)-(VII)).

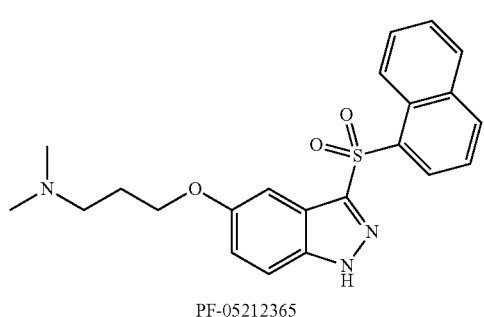
PF-05212365
IV

It is worth noting that the above mentioned structures, adapt in the pharmacophore models for 5-HT$_6$ receptors antagonists, independently developed by Pullagurla (Pullagurla et al., 2004) and López-Rodriguez (López-Rodriguez et al. 2005). The key elements proposed in these models are the two hydrophobic regions, double hydrogen bond acceptor (mainly sulfonyl or sulfonamide moiety) and the basic center of the molecule.

Although the sulfonyl or sulfonamide group may be replaced by its amide or alkyl bioisoster or carboxamide group (Cole et al., 2003; WO2005030724), arylsulfonyl and arylsulfonamide derivatives remain an important class of 5-HT$_6$ ligands. Several patent publication e.g. U.S. Pat. No. 8,003,670, U.S. Pat. No. 6,423,717, U.S. Pat. No. 7,960,374 B2, US 2009/0069337 A1, WO 2011/044134 A1, EP 2069310 B1, disclose several classes of arylsulfonamides, and claim their potential application in the treatment of CNS disorders related to disturbance of 5-HT$_6$ receptor functions.

The goal of the present invention relates to providing potent and selective 5-HT$_6$ antagonists based on a pyrroloquinoline core structure, as compounds useful for the treatment of certain CNS disorders.

Since many years the pyrrolo[3,2-c]quinoline system has been widely used as a central core of biologically active compounds possessing antitumor (Helissey et al., 1987), hypotensive (Wright et al., 1971) and anti-inflammatory properties (U.S. Pat. No. 5,216,162). Pyrroloquinoline-derived heterocycles were also shown to inhibit the gastric $(H^+/K^+)$-ATPase, an enzyme responsible for secretion of acid into the gastric lumen (Brown et al., 1990).

The antisecretory activity of pyrrolo[3,2-c]quinolines was found beneficial in the treatment of the gastric ulcer and was disclosed in the international patent publication WO 00/01696 (Formulas (VIII)-(IX)).

It is worth noting that pyrrolo[2,3-f]quinolines were reported to show affinity for $5-HT_{2A}$, $5-HT_{2B}$ and $5-HT_{2C}$ receptors. Patent publication U.S. Pat. No. 6,365,598 B1 discloses series of differently substituted pyrroloquinolines as agonists and antagonists of $5-HT_{2A}$ and $5-HT_{2C}$ sites and their application in the treatment of CNS disorders, including obesity, schizophrenia, depression, anxiety, migraine, sexual disorders, pain and gastrointestinal dysfunctions (Formula (XII)).

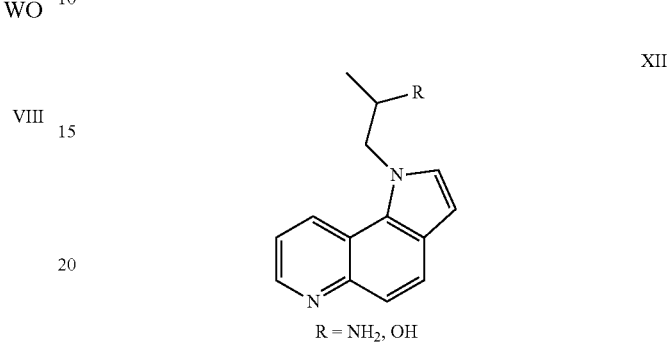

R = NH$_2$, OH

Moreover, their structural analogs, pyrroloquinoxaline derivatives, have been developed as potent $5-HT_3$ receptors agonists with potential analgesic-like properties.

Recently, Benakki et al. reported on a synthesis of N-methyl-pyrrolo-[3,2-c]quinoline derivatives of general formula (XIII) (Benakki et al., 2008).

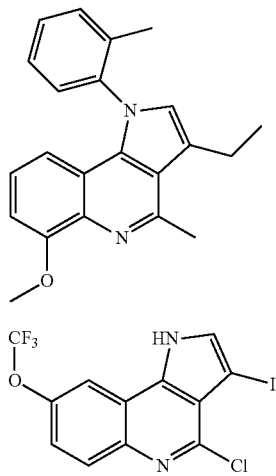

Furthermore, derivatives containing pyrrolo[3,2-c]quinoline core unit might act as inhibitors of kynurenine-3-hydroxylase (KYN-OH) enzyme, which is involved in the tryptophan metabolism and leads to the accumulation of the potent neurotoxic quinolinic acid. It is believed that selective inhibition of KYN-OH might play a rote in the neuronal protection (Heidempergher et al., 1999). The synthesis of pyrrolo[3,2-c]quinoline derivatives along with their use for the prevention and treatment in the neurodegenerative diseases, revealed by such mechanism of action, was the subject of the international patent application WO 98/05660 (Formulas (X)-(XI)).

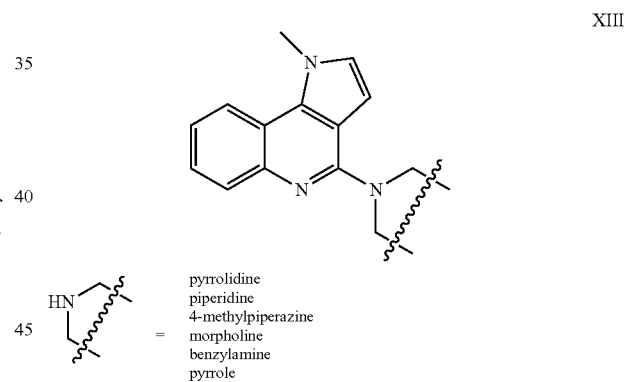

pyrrolidine
piperidine
4-methylpiperazine
= morpholine
benzylamine
pyrrole

DISCLOSURE

Surprisingly, it was found that certain pyrroloquinolone derivatives are $5-HT_6$ receptor antagonists. The invention relates to a compound of the general formula (XIV):

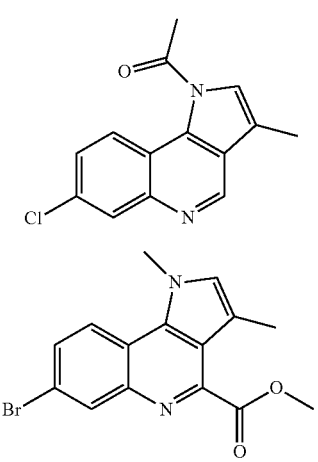

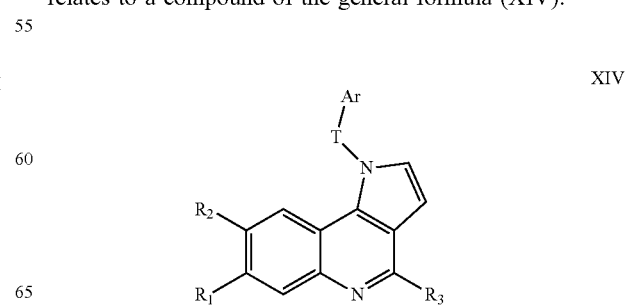

or a tautomer, stereoisomer, N-oxide, isotopically-labelled analogue, or a pharmacologically acceptable salt, hydrate or solvate of any of the foregoing, wherein:

$R_1$, $R_2$ independently represent hydrogen, an unsubstituted alkyl($C_1$-$C_3$) group, an alkyl($C_1$-$C_3$) group substituted with one or more halogen atoms, an alkoxyl ($C_1$-$C_3$) group, or independently a group selected from: cyano, nitro, amino, hydroxyl;

T represents CO, $CH_2$, substituted alkyl($C_1$-$C_2$) group, SO, $SO_2$;

Ar represents unsubstituted aryl (5-6 membered), biaryl (8-10 membered), heteroaryl (5-6 membered), heteroaryl (8-10 membered) having 1-3 heteroatoms independently selected from the group consisting of N, O, S, optionally substituted with one or more substituents selected from alkyl($C_1$-$C_3$) group, an alkyl($C_1$-$C_3$) group substituted with one or more halogen atoms, alkoxy($C_1$-$C_3$) group, alkenyl($C_2$-$C_4$), halogen, nitro, hydroxyl, cyano, amino, alkylamino, carboxamide;

$R_3$ represents substituent selected from the group of cyclic or linear substituted or not substituted amines consisting of (XV)-(XVIII):

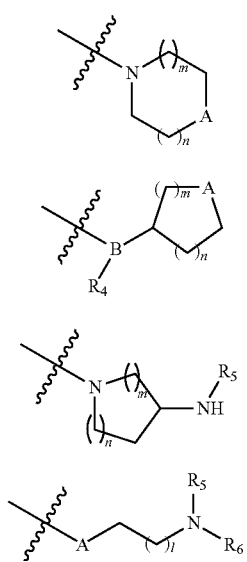

XV

XVI

XVII

XVIII wherein:
A represents NH, O, $CH_2$, $NR_5$;
B represents NH, O, $NR_4$;
$R_4$ represents hydrogen atom or alkyl($C_1$-$C_3$) group;
$R_5$ represents alkyl($C_1$-$C_3$) group or benzyl;
$R_6$ represents alkyl($C_1$-$C_3$) group;
n is selected from 0, 1, 2;
m is selected from 0, 1, 2;
l is selected from 1 and 2.

The invention particularly relates to a compound of the general formula (XIV) or a tautomer, stereoisomer, N-oxide or a pharmacologically acceptable salt, hydrate or solvate of any of the foregoing, wherein:

$R_1$, $R_2$ independently represent hydrogen, methyl, ethyl groups optionally substituted with one or more halogen atoms, or independently substituted with group selected from: cyano, nitro, amino, hydroxyl, methoxyl;

T represents CO, $CH_2$, substituted alkyl($C_1$-$C_2$) group, $SO_2$;

Ar represents unsubstituted aryl (5-6 membered), biaryl (8-10 membered), heteroaryl (5-6 membered), heteroaryl (8-10 membered) having 1-3 heteroatoms independently selected from the group consisting of N, O, S, optionally substituted with one or more substituents selected from alkyl($C_1$-$C_3$) group, an alkyl($C_1$-$C_3$) group substituted with one or more halogen atoms, methoxy, ethoxy, halogen, nitro, hydroxy, cyano, amino, alkylamino, carboxamide;

$R_3$ represents substituent selected from the group of cyclic or linear substituted or not substituted amines consisting of structures XV-XVIII, wherein: A, n, m, l have the meanings as given above;

B represents NH, O;
$R_4$ represents hydrogen atom;
$R_5$ represents alkyl ($C_1$-$C_3$) group or benzyl;
$R_6$ represents alkyl ($C_1$-$C_3$) group.

The invention relates to racemates, mixtures of diastereomers as well as the individual stereoisomers of the compounds having formula (XIV).

The compounds of the invention of formula (XIV), as well as pharmacologically acceptable salts thereof, have 5-$HT_6$ receptor antagonistic activity and as such are useful in treating and preventing diseases, disorders or conditions involving 5-$HT_6$ receptors, or treatable by manipulation of those receptors. Thus one aspect of the invention provides a method for the treatment, control or prevention of such diseases, disorders or conditions in a mammal which comprises administering to such mammal a therapeutically effective amount of a compound of formula XIV. The diseases, disorders or conditions for which the compounds of the present invention are useful in treating or preventing include, but are not limited to: schizophrenia, anxiety, depression, maniac depression, epilepsy, obsessive compulsive disorders, mood disorders, migraine, Alzheimer's disease, age related cognitive decline, mild cognitive impairment, steep disorders, eating disorders, anorexia, bulimia, panic attacks, attention deficit hyperactivity disorder, attention deficit disorder, Parkinson's disease, Huntington's disease, withdrawal from abuse of cocaine, ethanol, nicotine or benzodiazepines, pain, obesity and type-2 diabetes, functional bowel disorder, Irritable Bowel Syndrome.

Other embodiments of the invention include:
pharmaceutical compositions for treating disorders resulting from disturbance of 5-$HT_6$ transmission, the composition comprising a compound of formula (XIV), prodrugs, pharmaceutically acceptable salts and solvates thereof, and a pharmaceutically acceptable carrier;

methods of treating a disorder or condition treatable by blocking 5-HT6 receptors, the method comprising administering to a mammal in need of such treating a compound of formula (XIV) or pharmaceutically acceptable salt thereof;

pharmaceutical compositions for treating a disorder or condition chosen from the disorders listed herein, the compositions comprising a compound of formula (XIV) or a pharmaceutically acceptable salt thereof, and a pharmaceutically acceptable carrier;

methods of antagonizing a 5-$HT_6$ receptor that comprises administering to a subject in need thereof, an effective amount of a compound.

The invention also provides the use of a compound or salt according to formula (XIV) for the manufacture of medicament.

The invention further relates to combination therapies wherein a compound of the invention, of a pharmaceutically acceptable salt thereof, or a pharmaceutical composition or formulation comprising a compound of the invention, is administrated concurrently or sequentially or as a combined preparation with another therapeutic agent or agents, for treating one or more of the conditions listed. Such other therapeutic agent(s) may be administrated prior to, simultaneously with, of following the administration of the compounds of the invention.

The therapeutic agent or agents used in the combination with the compound of invention relates to the compounds used for treating a disorder or conditions chosen from the disorders listed in the invention, with the mechanism of action that synergistically ameliorate the positive outcomes of therapy.

The compounds of the invention exert 5-HT$_6$ receptor antagonist properties. This activity of the compounds of the

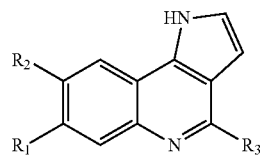

or a tautomer, stereoisomer, N-oxide, isotopically-labelled analogue or a pharmacologically acceptable salt, hydrate or solvate of any of the foregoing, wherein $R_1$, $R_2$, $R_3$ are the same as in formula (XIV).

The invention relates to racemates, mixtures of diastereomers as well as the individual stereoisomers of the compounds having formula (XIX).

The compounds of formula XIV can be prepared e.g. using the reactions and techniques described below. Generally, compounds described in the scope of this patent application can be synthesized by the route described in Scheme 1 and the Examples.

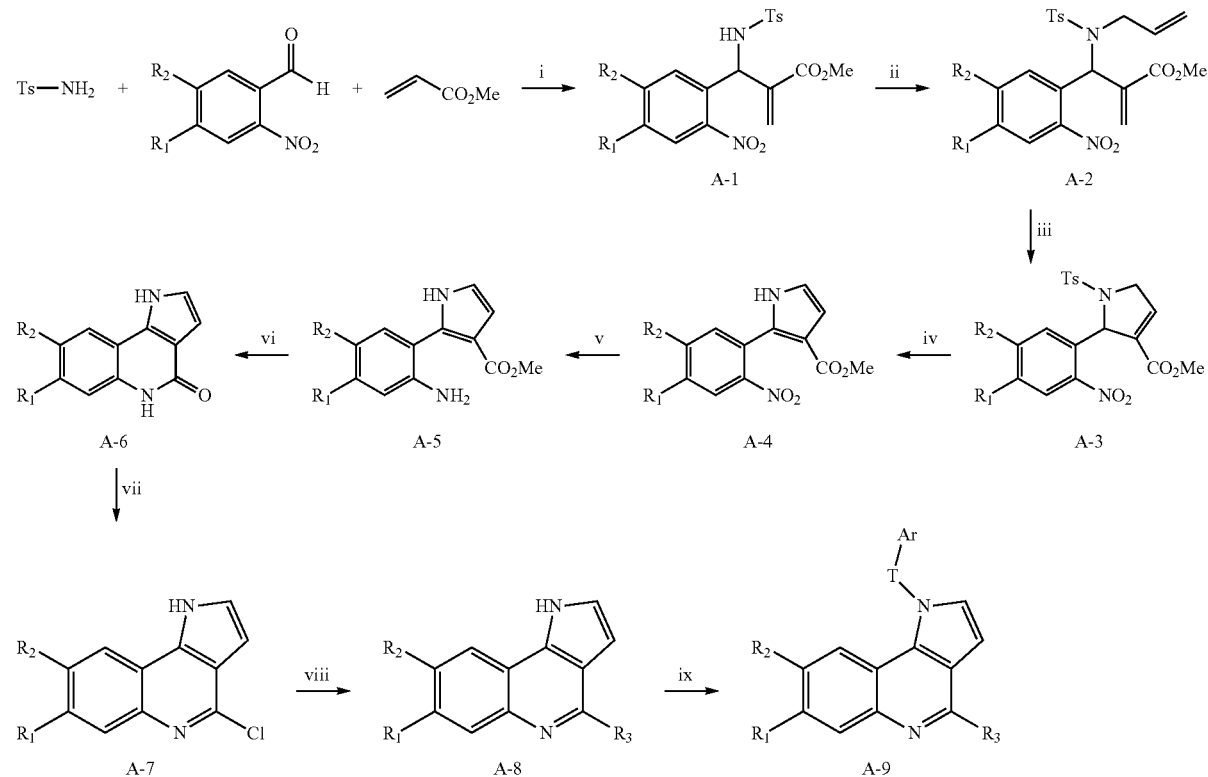

Scheme 1 invention is readily demonstrated, for example, using one or more of the assays described herein or known in the art.

The invention also provides methods of preparing the compounds of the invention and the intermediates used in those methods.

The invention relates to intermediates of general formula XIX:

In Scheme 1 compounds of formula XIV (A-9) and XIX (A-8) can be prepared by:
a) aza-Bayliss-Hillman reaction performed in a polar solvent selected from acetonitrile, ethanol, isopropanol, DMF or DMSO in the presence of tertiary amine such as DABCO (1,4-diazabicyclo[2.2.2]octane), quinuclidine or 3-hydroxyquinuclidine and Lewis acid selected from Sc(OTf)$_3$, Yb(OTf)$_3$, Ti(Oi-Pr)$_4$ and Cu(OTf)$_2$. The process is typically conducted for 24-48 hours at room temperature, b) Generation of diene derivative A-2 upon alkylation of A-1 with allyl bromide in the presence of a strong base selected from t-BuOK, t-BuONa, K$_2$CO$_3$, Cs(CO$_3$)$_2$, TEA, in a polar solvent preferably alcohol, acetonitrile or DMF, c) Ring-closing metathesis reaction of the derivative A-2. The process is typically performed using 3-10 mot % of ruthenium catalyst in dichloromethane or toluene and additionally supported by microwave irradiation, d) Treating the resulting pyrroline A-3 with a strong base to yield pyrrole derivative A-4. The reaction is typically performed in a suitable solvent such as DMF or DMSO, in a presence of base selected from t-BuOK, t-BuONa, K$_2$CO$_3$, Cs(CO$_3$)$_2$ or TEA, e) Reduction of the nitro derivative A-4 to its amino analog A-5. The conversion to the amino derivative is a conventional process, performed under hydrogen atmosphere, using 5-10 mol % of palladium on activated charcoal, f) Cyclization of the compound A-5 to the lactam A-6 in acidic conditions, a polar protic solvent e.g. 2-methoxyethanol, isopropanol, n-BuOH, sec-BuOH, t-BuOH, g) Conversion of the lactam derivative A-6 to its chloro analog A-7 by treating compound A-6 with a chlorinating agent such as POCl$_3$, SOCl$_2$, PCl$_5$ at the elevated temperature, h) Preparation of the amine/ether substituted pyrroloquinolines of the general structure A-8. The process may be performed using various solvents selected from non polar solvents such as toluene, benzene, xylenes, tetrahydrofuran and dioxane or polar solvents selected from acetone, acetonitrile, DMF, DMSO. The reaction is typically conducted at 70-140° C. for 2-24 h and is often supported by microwave irradiation, i) Treatment of pyrroloquinoline A-8 with differently substituted aryl sulfonyl halide, arylacyl halide or arylalkyl halide derivatives in the presence of a strong base selected from t-BuOK, t-BuONa, NaOH, NaH, TEA, DIEA or phosphazene bases such as BTPP to yield the final products A-9, in case of the Boc-protected amines the final products were deprotected in acidic conditions.

Isolation and purification of the compounds and intermediates described herein can be affected, if desired, by any suitable separation or purification procedure such as, for example, filtration, extraction, crystallization, column chromatography, thin layer chromatography, preparative low or high-pressure liquid chromatography, or a combination of these procedures.

Suitable separation and isolation procedures can be taken from the preparation and examples. However, other equivalent separation or isolation procedures could, of course, also be used.

The compounds of the present invention may contain one asymmetric center and can thus occur as racemates and racemic mixtures or single enantiomers.

Isomeric forms of compounds presented in general formula (XIV). Formula (XIV) shows the structure of the class of compounds without preferred stereochemistry. The independent syntheses of these isomers, or their chromatographic separation may be achieved as known in the art by appropriate modification of the methodology disclosed therein. Their absolute stereochemistry may be determined by the X-ray crystallography of crystalline products or crystalline intermediates, which are derivatized, if necessary, with a reagent containing as asymmetric center of known absolute configuration. The racemic mixture of compounds can be separated directly by chromatographic methods utilizing chiral stationary phases: methods well-known in the art. Alternatively, any enantiomer of a compound may be obtained by stereoselective synthesis using optically pure starting materials or reagents of known configuration by methods well-known in the art.

Some of the crystalline forms for the compounds may exist as polymorphs: as such intended to belong to the invention. In addition, some of the compounds may form solvates with water (i.e. hydrates), or common organic solvents. Such solvents also fall within the scope of this invention.

The compounds of the invention may also be used as reagents or standards in the biochemical study of neurological function, dysfunction and disease.

Examples of the compounds of the invention are the following:

1. N1,N1-dimethyl-N2-(1-(phenylsulfonyl)-1H-pyrrolo[3,2-c]quinolin-4-yl)ethane-1,2-diamine
2. 1-((3-chlorophenyl)sulfonyl)-N-(azetidin-3-yl)-1H-pyrrolo[3,2-c]quinolin-4-amine
3. 1-(naphthalen-1-ylsulfonyl)-N-(azetidin-3-yl)-1H-pyrrolo[3,2-c]quinolin-4-amine
4. 1-(phenylsulfonyl)-N-(pyrrolidin-3-yl)-1H-pyrrolo[3,2-c]quinolin-4-amine
5. 1-((3-chlorophenyl)sulfonyl)-N-(pyrrolidin-3-yl)-1H-pyrrolo[3,2-c]quinolin-4-amine
6. (S)-1-((3-chlorophenyl)sulfonyl)-N-(pyrrolidin-3-yl)-1H-pyrrolo[3,2-c]quinolin-4-amine
7. (R)-1-((3-chlorophenyl)sulfonyl)-N-(pyrrolidin-3-yl)-1H-pyrrolo[3,2-c]quinolin-4-amine
8. 1-((3-fluorophenyl)sulfonyl)-N-(pyrrolidin-3-yl)-1H-pyrrolo[3,2-c]quinolin-4-amine
9. (S)-1-((3-fluorophenyl)sulfonyl)-N-(pyrrolidin-3-yl)-1H-pyrrolo[3,2-c]quinolin-4-amine
10. (R)-1-((3-fluorophenyl)sulfonyl)-N-(pyrrolidin-3-yl)-1H-pyrrolo[3,2-c]quinolin-4-amine
11. 1-((4-fluorophenyl)sulfonyl)-N-(pyrrolidin-3-yl)-1H-pyrrolo[3,2-c]quinolin-4-amine
12. 1-((2,5-difluorophenyl)sulfonyl)-N-(pyrrolidin-3-yl)-1H-pyrrolo[3,2-c]quinolin-4-amine
13. 1-((3-methoxyphenyl)sulfonyl)-N-(pyrrolidin-3-yl)-1H-pyrrolo[3,2-c]quinolin-4-amine
14. 1-((3-(trifluoromethyl)phenyl)sulfonyl)-N-(pyrrolidin-3-yl)-1H-pyrrolo[3,2-c]quinolin-4-amine
15. (S)-1-((3-(trifluoromethyl)phenyl)sulfonyl)-N-(pyrrolidin-3-yl)-1H-pyrrolo[3,2-c]quinolin-4-amine
16. (R)-1-((3-(trifluoromethyl)phenyl)sulfonyl)-N-(pyrrolidin-3-yl)-1H-pyrrolo[3,2-c]quinolin-4-amine
17. 1-((4-(tert-butyl)phenyl)sulfonyl)-N-(pyrrolidin-3-yl)-1H-pyrrolo[3,2-c]quinolin-4-amine
18. 1-((4-aminophenyl)sulfonyl)-N-(pyrrolidin-3-yl)-1H-pyrrolo[3,2-c]quinolin-4-amine
19. (S)-1-((4-aminophenyl)sulfonyl)-N-(pyrrolidin-3-yl)-1H-pyrrolo[3,2-c]quinolin-4-amine
20. (R)-1-((4-aminophenyl)sulfonyl)-N-(pyrrolidin-3-yl)-1H-pyrrolo[3,2-c]quinolin-4-amine
21. 1-(naphthalen-1-ylsulfonyl)-N-(pyrrolidin-3-yl)-1H-pyrrolo[3,2-c]quinolin-4-amine
22. 1-(quinolin-8-ylsulfonyl)-N-(pyrrolidin-3-yl)-1H-pyrrolo[3,2-c]quinolin-4-amine
23. 1-((5-methylbenzo[b]thiophen-2-yl)sulfonyl)-N-(pyrrolidin-3-yl)-1H-pyrrolo[3,2-c]quinolin-4-amine
24. 7-fluoro-1-((3-chlorophenyl)sulfonyl)-N-(pyrrolidin-3-yl)-1H-pyrrolo[3,2-c]quinolin-4-amine
25. 8-chloro-1-((3-chlorophenyl)sulfonyl)-N-(pyrrolidin-3-yl)-1H-pyrrolo[3,2-c]quinolin-4-amine
26. N-methyl-1-(1-(phenylsulfonyl)-1H-pyrrolo[3,2-c]quinolin-4-yl)pyrrolidin-3-amine
27. 1-(phenylsulfonyl)-4-(piperazin-1-yl)-1H-pyrrolo[3,2-c]quinoline
28. 1-((2-bromophenyl)sulfonyl)-4-(piperazin-1-yl)-1H-pyrrolo[3,2-c]quinoline
29. 1-((3-chlorophenyl)sulfonyl)-4-(piperazin-1-yl)-1H-pyrrolo[3,2-c]quinoline

| | |
|---|---|
| 30 | 1-((3-fluorophenyl)sulfonyl)-4-(piperazin-1-yl)-1H-pyrrolo[3,2-c]quinoline |
| 31 | 1-((4-fluorophenyl)sulfonyl)-4-(piperazin-1-yl)-1H-pyrrolo[3,2-c]quinoline |
| 32 | 1-((2,5-difluorophenyl)sulfonyl)-4-(piperazin-1-yl)-1H-pyrrolo[3,2-c]quinoline |
| 33 | 1-((3,4-difluorophenyl)sulfonyl)-4-(piperazin-1-yl)-1H-pyrrolo[3,2-c]quinoline e |
| 34 | 1-((3,4-dichlorophenyl)sulfonyl)-4-(piperazin-1-yl)-1H-pyrrolo[3,2-c]quinoline |
| 35 | 1-((3-(trifluoromethyl)phenyl)sulfonyl)-4-(piperazin-1-yl)-1H-pyrrolo[3,2-c]quinoline |
| 36 | 1-((4-(trifluoromethyl)phenyl)sulfonyl)-4-(piperazin-1-yl)-1H-pyrrolo[3,2-c]quinoline |
| 37 | 1-((3-methoxyphenyl)sulfonyl)-4-(piperazin-1-yl)-1H-pyrrolo[3,2-c]quinoline |
| 38 | 1-((3-cyanophenyl)sulfonyl)-4-(piperazin-1-yl)-1H-pyrrolo[3,2-c]quinoline |
| 39 | 1-((3-methylphenyl)sulfonyl)-4-(piperazin-1-yl)-1H-pyrrolo[3,2-c]quinoline |
| 40 | 1-((4-isopropylphenyl)sulfonyl)-4-(piperazin-1-yl)-1H-pyrrolo[3,2-c]quinoline |
| 41 | 1-((4-(tert-butyl)phenyl)sulfonyl)-4-(piperazin-1-yl)-1H-pyrrolo[3,2-c]quinoline |
| 42 | 1-(4-(aminophenyl)sulfonyl)-4-(piperazin-1-yl)-1H-pyrrolo[3,2-c]quinoline |
| 43 | 1-(naphthalen-1-ylsulfonyl)-4-(piperazin-1-yl)-1H-pyrrolo[3,2-c]quinoline |
| 44 | 1-(naphthalen-2-ylsulfonyl)-4-(piperazin-1-yl)-1H-pyrrolo[3,2-c]quinoline |
| 45 | 1-(quinolin-8-ylsulfonyl)-4-(piperazin-1-yl)-1H-pyrrolo[3,2-c]quinoline |
| 46 | 1-((5-chlorothiophen-2-yl)sulfonyl)-4-(piperazin-1-yl)-1H-pyrrolo[3,2-c]quinoline |
| 47 | 1-((5-methylbenzo[b]thiophen-2-yl)sulfonyl)-4-(piperazin-1-yl)-1H-pyrrolo[3,2-c]quinoline |
| 48 | 1-((5-chloro-3-methylbenzo[b]thiophen-2-yl)sulfonyl)-4-(piperazin-1-yl)-1H-pyrrolo[3,2-c]quinoline |
| 49 | 1-(3-chlorobenzyl)-4-(piperazin-1-yl)-1H-pyrrolo[3,2-c]quinoline |
| 50 | 1-(3-fluorobenzyl)-4-(piperazin-1-yl)-1H-pyrrolo[3,2-c]quinoline |
| 51 | (3-chlorophenyl)-(4-(piperazin-1-yl)-1H-pyrrolo[3,2-c]quinolin-1-yl)methanone |
| 52 | (3-methylphenyl)-(4-(piperazin-1-yl)-1H-pyrrolo[3,2-c]quinolin-1-yl)methanone |
| 53 | 1-(phenylsulfonyl)-4-(4-methylpiperazin-1-yl)-1H-pyrrolo[3,2-c]quinoline |
| 54 | 1-((3-chlorophenyl)sulfonyl)-4-(4-methylpiperazin-1-yl)-1H-pyrrolo[3,2-c]quinoline |
| 55 | 1-((3-fluorophenyl)sulfonyl)-4-(4-methylpiperazin-1-yl)-1H-pyrrolo[3,2-c]quinoline |
| 56 | 1-((4-fluorophenyl)sulfonyl)-4-(4-methylpiperazin-1-yl)-1H-pyrrolo[3,2-c]quinoline |
| 57 | 1-((4-aminophenyl)sulfonyl)-4-(4-methylpiperazin-1-yl)-1H-pyrrolo[3,2-c]quinoline |
| 58 | 1-(naphthalen-1-ylsulfonyl)-4-(4-methylpiperazin-1-yl)-1H-pyrrolo[3,2-c]quinoline |
| 59 | 1-(quinolin-8-ylsulfonyl)-4-(4-methylpiperazin-1-yl)-1H-pyrrolo[3,2-c]quinolone |
| 60 | 1-(phenylsulfonyl)-4-(4-benzylpiperazin-1-yl)-1H-pyrrolo[3,2-c]quinoline |
| 61 | 1-((5-chlorothiophen-2-yl)sulfonyl)-4-(4-benzylpiperazin-1-yl)-1H-pyrrolo[3,2-c]quinoline |
| 62 | 1-(quinolin-8-ylsulfonyl)-4-(4-benzylpiperazin-1-yl)-1H-pyrrolo[3,2-c]quinoline |
| 63 | 8-nitro-1-((4-isopropylphenyl)sulfonyl)-4-(piperazin-1-yl)-1H-pyrrolo[3,2-c]quinoline |
| 64 | 8-nitro-1-((3-(trifluoromethyl)phenyl)sulfonyl)-4-(piperazin-1-yl)-1H-pyrrolo[3,2-c]quinoline |
| 65 | 8-amino-1-((3,4-dichlorophenyl)sulfonyl)-4-(piperazin-1-yl)-1H-pyrrolo[3,2-c]quinoline |
| 66 | 8-carbonitrile-1-(3-methylphenyl)-4-(piperazin-1-yl)-1H-pyrrolo[3,2-c]quinoline |
| 67 | 8-carbonitrile-1-(naphthalen-1-ylsulfonyl)-4-(piperazin-1-yl)-1H-pyrrolo[3,2-c]quinoline |
| 68 | 8-methoxy-1-((3-(trifluoromethyl)phenyl)sulfonyl)-4-(piperazin-1-yl)-1H-pyrrolo[3,2-c]quinoline |
| 69 | 8-methoxy-1-((3-fluorophenyl)sulfonyl)-4-(piperazin-1-yl)-1H-pyrrolo[3,2-c]quinoline |
| 70 | 8-chloro-1-((3-chlorophenyl)sulfonyl)-4-(piperazin-1-yl)-1H-pyrrolo[3,2-c]quinoline |
| 71 | 8-chloro-1-(naphthalen-1-ylsulfonyl)-4-(piperazin-1-yl)-1H-pyrrolo[3,2-c]quinoline |
| 72 | 7-fluoro-1-((3-methylphenyl)sulfonyl)-4-(piperazin-1-yl)-1H-pyrrolo[3,2-c]quinoline |
| 73 | 7-fluoro-1-((3-chlorophenyl)sulfonyl)-4-(piperazin-1-yl)-1H-pyrrolo[3,2-c]quinoline |
| 74 | 1-((3,4-difluorophenyl)sulfonyl)-4-(1,4-diazepan-1-yl)-1H-pyrrolo[3,2-c]quinoline |
| 75 | 1-((3-chlorophenyl)sulfonyl)-4-(1,4-diazepan-1-yl)-1H-pyrrolo[3,2-c]quinoline |
| 76 | 1-((3-chlorophenyl)sulfonyl)-4-(piperidin-1-yl)-1H-pyrrolo[3,2-c]quinoline |
| 77 | 1-(quinolin-8-ylsulfonyl)-4-(piperidin-1-yl)-1H-pyrrolo[3,2-c]quinoline |
| 78 | 1-((3-chlorophenyl)sulfonyl)-4-(morpholine-4-yl)-1H-pyrrolo[3,2-c]quinoline |
| 79 | 1-(quinolin-8-ylsulfonyl)-4-(morpholine-4-yl)-1H-pyrrolo[3,2-c]quinoline |
| 80 | 1-((3-methylphenyl)sulfonyl)-4-(pyrrolidin-3-yloxy)-1H-pyrrolo[3,2-c]quinoline |
| 81 | 1-((2,5-difluorophenyl)sulfonyl)-4-(pyrrolidin-3-yloxy)-1H-pyrrolo[3,2-c]quinoline |

The chemical names of the substances were generated using ChemBioDraw Ultra 12.0. For the avoidance of doubt, if chemical name and chemical structure of the above illustrated compounds do not correspond by mistake, the chemical structure is regarded to unambiguously define the compound.

DEFINITIONS

General terms used in the description of compounds herein disclosed bear their usual meanings. The term alkyl as used herein denotes a univalent saturated branched or straight hydrocarbon chain. Unless otherwise stated such chains can contain from 1 to 3 carbon atoms. Representative of such alkyl groups are methyl, ethyl, propyl, isopropyl and the like. The same carbon content applies to the patent term 'alkane', and to derivative terms such as 'alkoxy'. The carbon content of various hydrocarbon containing moieties is indicated by a prefix designating the minimum and maximum number of carbon atoms in the moiety, i.e., the prefix $C_x$-$C_y$ defines the number of carbon atoms present from the integer "x" to the integer "y" inclusive. 'Alkyl($C_{1-3}$)' for example, means methyl, ethyl, n-propyl or isopropyl.

The term 'aryl' embraces monocyclic or fused bicyclic aromatic or hetero-aromatic groups, including but not limited to furyl, thienyl, pyrroryl, oxazolyl, thiazolyl, imidazolyl, imidazo[2,1-b][1,3]thiazolyl, pyrazolyl, isoxazolyl, isothiazolyl, pyridyl, pyridazinyl, pirymidinyl, pyrazinyl, 1,3,5-triazinyl, phenyl, 1H-indazol-7-yl, 1H-indol-2-yl, 1H-indol-6-yl, indolizinyl, isoindolyl, 1-benzofuran-2-yl, 1-benzofuran-3-yl, 1,2,3,4-tetrahydronaphtyl, 1,2,3,4-tetrahydroisoquinolinyl, indanyl, indenyl, 1-benzothien-3-yl, 1-benzothien-2-yl, 2,3-dihydro-1,4-benzodioxin-5-yl, benzimidazolyl, 1,3-benzothiazol-4-yl, 1,3-benzothiazol-5-yl, benzo[1,2,5]thiaz-diazolyl, quinolinyl, isoquinolinyl, phtalazinyl, quinazolinyl, quinoxalinyl, 1,8-naphthyridinyl, naphtyl, pteridinyl or azulenyl. 'Halo' or 'Halogen' means chloro, fluoro, bromo or iodo; 'hetero' as in 'heteroalkyl, heteroaromatic' etc. means containing one or more N, O or S atoms. 'heteroalkyl' includes alkyl groups with heteroatoms in any position, thus including N-bound O-bound or S-bound alkyl groups.

The term 'substituted' means that the specified group or moiety bears one or more substituents. Where any group may carry multiple substituents, and a variety of possible substituents is provided, the substituents are independently selected, and need not to be the same. The term 'unsubstituted' means that the specified group bears no substituents.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertary amines, or less active. While N-oxides can easily be reduced to their corresponding tertary amines by chemical means, in human body this happens to varying degrees. Some N-oxides undergo nearly quantitative reductive conversion to the corresponding tertiary amines, in other cases is a mere trace reaction, or even completely absent.

Any compound metabolized in vivo to provide the bioactive agent (i.e., the compound of formula (XIV) is a prodrug within the scope and spirit of the application. Prodrugs are therapeutic agents, inactive per se but transformed into one or more active metabolites. Thus in the methods of treatment of the present invention, the term "administering" shall encompass treating the various disorders described with the compound specifically disclosed, or with a compound that not specifically disclosed, but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism and targeting limitations. Prodrugs, i.e. compounds that when administered to humans by any known route, are metabolized to compounds having formula (XIV) belong to the invention. In particular this relates to compounds with primary or secondary amino or hydroxy groups. Such compounds can be reacted with organic acids to yield compounds having formula (XIV) wherein an additional group is present that is easily removed after administration, for instance, but not limited to amidine, enamine, a Mannich base, a hydroxyl-methylene derivative, an O-(acyloxymethylene carbamate) derivative, carbamate, ester, amide or enaminone.

'Crystal form' refers to various solid forms of the same compound, for example polymorphs, solvates and amorphous forms. The compound of formula (XIV) and pharmaceutically acceptable salts thereof may exist in a form of hydrate or a solvate, and such a hydrate and solvate are also encompassed in the present invention. Examples thereof include 1/10 hydrates hydrate, 1/4 hydrate, monohydrate, dihydrochloride, dihydrate, dihydrochloride 3/2 hydrate, and the like. 'Amorphous' forms are non-crystalline materials with no long range order, and generally do not give a distinctive powder X-ray diffraction pattern.

The terms "selective" and "selectivity" refer to compounds that display reactivity towards a particular receptor (e.g. a 5-HT$_6$ receptor) without displaying substantial cross-reactivity towards another receptor (e.g. other 5-HT receptor sub-types). Thus, for example, selective compounds of the present invention may display reactivity towards 5-HT$_6$ receptors without displaying substantial cross-reactivity towards other 5-HT receptors. In one embodiment, a compound of the present invention has at least about 10 folds selectivity to the 5-HT$_6$ receptor, at least about 50 folds selectivity to the 5-HT$_6$ receptor, at least about 100 folds selectivity to 5-HT$_6$ receptor, at least about 250 folds selectivity to 5-HT$_6$ receptor, or at least about 500 folds selectivity to the desired target.

Throughout the description and the claim of the specification the word "comprise" and variations of the word, such as "comprising" and "comprises" is not intended to exclude other additives, components, integers or steps.

While it may be possible for the compounds of formula (XIV) to be administered as the raw chemical, it is preferable to present them as a 'pharmaceutical composition'. According to a further aspect, the present invention provides a pharmaceutical composition comprising a compound of formula (XIV), or pharmaceutically acceptable salt or solvate thereof, together with one or more pharmaceutically acceptable carriers thereof, and optionally one or more other therapeutic ingredients. The carrier(s) must be 'acceptable' in the sense of being compatible with the other ingredients of the formulation and not deleterious to the recipient thereof.

The term "composition" as used herein encompasses a product comprising specified ingredients in predetermined amount or proportions, as well as any product that results, directly or indirectly, from combining specified ingredients in specified amounts. In relation to pharmaceutical compositions, this term encompasses a product comprising one or more active ingredients, and an optimal carrier comprising inert ingredients, as well as any product that results, directly or indirectly from combination, complexation or aggregation of any two or more of the ingredients, or from dissociation of one or more of the ingredients, or from other types of reactions or interaction of one or more of the ingredients. In general, pharmaceutical compositions are prepared by uniformly and intimately bringing the active ingredients into association with a liquid carrier or a finely divided solid carrier or both, and then, if necessary, shaping the product into desired formulation. The pharmaceutical composition includes enough of the active object compound to produce the desired effect upon the progress or condition of disease. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

With the context of this application, the term "combination preparation" comprises both true combinations, meaning a compound of formula (XIV) and one or more other medicaments physically combined in one preparation such as a tablet or injection fluid, comprising a compound of formula (XIV) and one or more other medicaments in separate dosage forms, together with instruction for use, optionally with further means for facilitating compliance with the administration of the component compounds, e.g. label or drawings. With true combinations, the pharmacotherapy by definition is simultaneous.

The affinity of the compound of the invention for 5-HT$_6$ receptors was determined using radioligand binding assay. From the binding affinity measured for a given compound of formula (XIV), one can estimate a theoretical lowest effective dose. At a concentration of the compound equal to twice the measured $K_i$-value, nearly 100% of the 5-HT$_6$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The typical daily dose of the active ingredients varies within a wide range and will depend on various factors such as the relevant indication, the route of administration, the age, weight and sex of the patient and may be determined by a physician. In general, total daily dose administration to a patient a single or individual doses, may be in amounts, for example from 0.001 to 10 mg/kg body weight daily, and more usually 0.01 to 1000 mg per day, of total active ingredients.

The term "therapeutically effective amount" as used herein refers to an amount of a therapeutic agent to treat a condition treatable by administrating a composition of the invention. That amount is the amount sufficient to exhibit a detectable therapeutic or ameliorative response in as tissue system, animal or human. It is not useful to specify an exact effective amount in advance.

The term "pharmaceutically acceptable salt" refers to those salts that are, within the scope medical judgment, suitable for use in contact with tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic acids, including inorganic or organic acids (Berge, 1977). The "free base" form may be regenerated by contacting the salt with a base, and isolating the parent compound in the conventional matter. The parent form of the compound differs from the various salt forms in certain physical properties, such as solubility in polar solvents, but otherwise the salts are equivalent to the parent form of the compound for the purposes of the present invention.

"Complex" refers to a complex of the compound of the invention, e.g. formula (XIV), complexed with a metal ion, where at least one metal atom is chelated or sequestered. Complexes are prepared by methods well known in the art (Dwyer, 1964).

The term "treatment" as used herein refers to any treatment a mammalian, for example human condition or disease, and includes: (1) inhibiting the disease or condition, i.e., arresting its development, (2) relieving the disease or condition, i.e.; causing the condition to regress, or (3) stopping the symptoms of the disease.

As used herein, the term "medical therapy" intendeds to include prophylactic, diagnostic and therapeutic regimens carries out in vivo or ex vivo on humans or other mammals.

| Abbreviations | |
|---|---|
| AcOEt | ethyl acetate; |
| AcOH | acetic acid; |
| BINAP | 2,2'-bis(diphenylphosphino)-1,1'-binaphthyl |
| BTPP | phosphazene base P1-t-Bu-tris(tetramethylene); |
| BuOH | butanol; |
| CDCl$_3$ | deuterated chloroform; |
| CD$_3$OD | deuterated methanol; |
| DABCO | 1,4-diazabicyclo[2.2.2]octane; |
| DCM | dichloromethane; |
| DIEA | diisopropylethylamine; |
| DMF | dimethylformamide; |
| DMSO | dimethyl sulfoxide; |
| HCl | hydrochloric acid; |
| Hex | hexane; |
| MeCN | acetonitrile; |
| MeOH | methanol; |
| NaH | sodium hydride; |
| NaOH | sodium hydroxide; |
| NaH | sodium hydride; |
| NaOH | sodium hydroxide; |
| Na$_2$SO$_4$ | sodium sulfate; |
| PCl$_5$ | phosphorus pentachloride; |
| Pd/C | palladium on activated charcoal; |

| Abbreviations | |
|---|---|
| Pd$_2$(dba)$_3$ | tris(dibenzylideneacetone)-dipalladium(0); |
| POCl$_3$ | phosphorus oxychloride; |
| SOCl$_2$ | thionyl chloride; |
| t-BuOK | potassium tert-butoxide |
| t-BuONa | sodium tert-butoxide |
| TEA | triethylamine; |
| MW | molecular weight; |
| HPLC | high performance liquid chromatography; |
| $^1$H NMR | Proton Nuclear Magnetic Resonance; |
| LC-MS | high performance liquid chromatography coupled to mass spectrometer. |

GENERAL ANALYTICAL METHODS

The synthesis was carried out at ambient temperature, unless indicated otherwise. Organic solvents (from Aldrich and Chempur) were of reagent grade and were used without purification. The reagents were from Aldrich, Chembridge, Fluorochem.

Analytical HPLC were run on a Waters Alliance HPLC instrument, equipped with a ChromolithSpeedROD column (4.6×50 mm). Standard conditions were eluent system A (water/0.1% TFA), system B (acetonitrile/0.1% TFA). A flow rate of 5 mL/min and a gradient of (0-100)% B over 3 min were used. Detection was performed on a PDA detector.

$^1$H NMR spectra were obtained in a Varian BB 200 spectrometer using TMS (0.00 ppm) in chloroform-d$_1$, and were recorded at 300 MHz; J values are in hertz (Hz), and splitting patterns are designated as follows: s (singlet), d (doublet), t (triplet), m (multiplet).

LC/MS were carried out on a system consisted of a Waters Acquity UPLC, coupled to a Waters TQD mass spectrometer. All the analyses were carried out using a Acquity UPLC BEH C18, 50×2.1 mm column, at 40° C. A flow rate of 0.3 mL/min and a gradient of (5-95)% B over 10 min was used. Eluent A: water/0.1% HCO$_2$H; eluent B: acetonitrile/0.1% HCO$_2$H. The UPLC/MS purity of all the test compounds and key intermediates was determined to be >97%.

EXAMPLE 1

Example 1.1

Synthesis of Substituted 7-Chloropyrroloquinolines of General Structure A-7

Methyl 2-[(2-Nitrophenyl)-(4-Toluenesulfonylamino)-Methyl]acrylate (A-1)

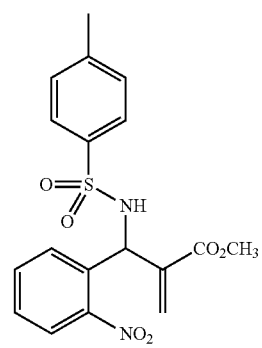 [SMILES: C=C(C(=O)OC)C(NS(=O)(=O)c1ccc(C)cc1)c1ccccc1[N+](=O)[O-]]

In a dried flask p-toluenosulfonamide (18 g, 105 mmol, 1 eq) and DABCO (1.78 g, 15.7 mmol, 1 eq) were mixed together with the previously activated molecular sieves (4 Å, 21 g). The mixture was suspended in isopropanol (300 ml), followed by addition of nitrobenzaldehyde (15.8 g, 105 mmol, 1 eq) and methyl acrylate (10.7 ml, 115 mmol, 1.1 eq). Subsequently, Ti(iOPr)$_4$ was added as a freshly prepared solution in isopropanol (0.6 ml, 2.1 mmol, 0.02 eq). The flask was filled with nitrogen and the mixture was stirred at room temperature for 24 h. Then, a mixture was filtered through Cetite which was rinsed with DCM. The solvent was evaporated and to the remaining crude was dissolved in AcOEt, washed with 1M KHSO$_4$, saturated NaHCO$_3$, water and brine and dried over MgSO$_4$. Evaporation of the solvent gave a yellow oil which was subsequently dissolved in AcOEt and crystalized upon addition of n-hexane. The appearing white precipitate was filtrated, rinsed with diethyl ether and dried under vacuum.

White solid, Mp 109-111° C., yield 63%, C$_{18}$H$_{18}$N$_2$O$_6$S, MW 390.41, Monoisotopic Mass 390.09, [M+H]$^+$ 391.4.

$^1$H NMR (300 MHz, CDCl$_3$) δ (ppm) 2.40 (s, 3H), 3.56 (s, 3H), 5.68 (s, 1H), 5.84-5.87 (d, 1H, J=8.72 Hz), 6.06-6.09 (d, 1H, J=8.46 Hz), 6.21 (s, 1H), 7.22-7.26 (m, 2H), 7.36-7.42 (td, 1H, J=7.44 Hz, J=1.28 Hz), 7.51-7.56 (td, 1H, J=7.70 Hz, J=1.28 Hz), 7.67-7.70 (m, 3H), 7.80-7.84 (dd, 1H, J=8.08 Hz, J=1.54 Hz).

Methyl 2-[(N-allyl-N-tosylamino)-(2-nitrophenyl)-methyl]acrylate (A-2)

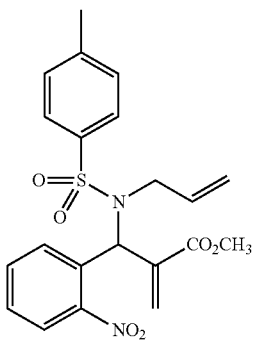 [SMILES: C=CCN(C(C(=C)C(=O)OC)c1ccccc1[N+](=O)[O-])S(=O)(=O)c1ccc(C)cc1]

β-aminoester A-1 (10 g, 25.6 mmol, 1 eq) was dissolved in DMF (100 ml), followed by addition of K$_2$CO$_3$ (10.5 g, 76.5 mmol, 3 eq). Subsequently, allyl bromide (4.42 ml, 51.2 mmol, 2 eq) was added dropwisely. The reaction mixture was stirred at room temperature for 6 h. Then, the mixture was diluted with ethyl acetate and washed with water (5×) and brine. The organic phase was concentrated under vacuum. The obtained yellow solid was treated with diethyl ether giving a white precipitate which was filtrated and dried under vacuum.

White solid, Mp 83-85° C., yield 95%, C$_{21}$H$_{22}$N$_2$O$_6$S, MW 430.47, Monoisotopic Mass 430.12, [M+H]$^+$430.8. $^1$H NMR (300 MHz, CDCl$_3$) δ (ppm) 2.41 (s, 3H) 3.49-3.55 (m, 3H) 3.92-4.01 (m, 1H) 4.15-4.25 (m, 1H) 4.92-5.03 (m, 2H) 5.43-5.59 (m, 2H) 6.44 (s, 1H) 6.79 (s, 1H) 7.23-7.27 (m, 2H) 7.42-7.49 (m, 1H) 7.61-7.68 (m, 3H) 7.75-7.80 (d, 1H, J=7.69 Hz) 7.89-7.93 (dd, 1H, J=8.21 Hz, J=1.28 Hz).

Methyl 2,5-dihydro-2-(2-nitrophenyl)-1-tosyl-1H-pyrrole-3-carboxylate (A-3)

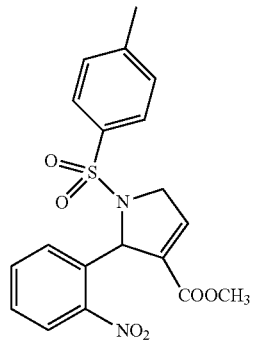 [SMILES: COC(=O)C1=CCN(S(=O)(=O)c2ccc(C)cc2)C1c1ccccc1[N+](=O)[O-]]

The β-aminoester A-2 (2 g, 4.64 mmol, 1 eq) was dissolved in DCM (12 ml) the Grubbs II catalyst (300 mg, 0.36 mmol, 0.03 eq) was added. The mixture was irradiated by microwaves at 38° C. for 30 min in Biotage MW. Then, DMSO (0.71 ml, 10 mmol, 2.1 eq) was added to a reaction mixture and it was stirred at room temperature for 20 h. After this time silica gel was added and was stirred for next 5 minutes. The mixture was diluted with DCM and filtrated through a layer of silica gel. The filtrate was concentrated under reduced pressure and the obtained residue was treated with diethyl ether to give a white precipitate which was filtrated and dried under vacuum.

Light brown solid, yield 80%, Mp 124-125° C., C$_{19}$H$_{18}$N$_2$O$_6$S, MW 402.42, Monoisotopic Mass 402.09, [M+H]$^+$ 403.31. $^1$HNMR 300 MHz, CDCl$_3$) δ (ppm) 2.36 (s, 3H), 3.45 (s, 3H), 4.29 (m, 1H), 4.54 (m, 1H), 6.61-6.64 (m, 1H), 6.68 (t, 1H, J=2.0 Hz), 7.27 (d, 2H, J=8.27 Hz), 7.31-7.36 (m, 1H), 7.48-7.50 (m, 2H), 7.74 (d, 2H, J=8.27 Hz), 7.83 (d, 1H, J=8.22 Hz).

Methyl 2-(2-nitrophenyl)-1H-pyrrole-3-carboxylate (A-4)

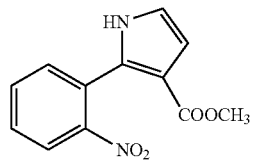

To a solution of 2,5-dihydropyrrole A-3 (2.5 g, 6.2 mmol, 1 eq) in DMF (40 ml) t-BuOK (2.09 g, 18.7 mmol, 3 eq) was added. The reaction mixture was stirred at ambient temperature for 2 hours under HPLC monitoring. Then, the mixture was diluted with ethyl acetate, neutralized with 1 M KHSO$_4$ (20 ml) and washed with saturated solution of NaHCO$_3$, water (3×) and brine. The organic layer was dried under Na$_2$SO$_4$ and concentrated under reduced pressure. The obtained crude was purified on silica gel with AcOEt/Hex (4/6) as a developing solvent.

Light brown solid, yield 100%, C$_{12}$H$_{10}$N$_2$O$_4$, MW 246.22, Monoisotopic Mass 246.06, [M+H]$^+$ 247.3. $^1$H NMR (300 MHz, CDCl$_3$) δ (ppm) 3.62-3.63 (m, 3H) 6.69-

6.73 (t, 1H, J=2.95 Hz) 6.82-6.85 (m, 1H) 7.44-7.48 (m, 1H) 7.51-58 (m, 1H) 7.60-7.66 (m, 1H) 8.03-8.04 (dd, 1H, J=8.21, J=1.28 Hz).

Methyl 2-(2-aminophenyl)-1H-pyrrole-3-carboxylate (A-5)

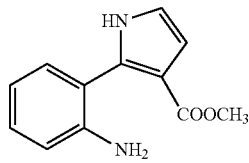

The nitro derivative A-4 (2.5 g, 10.2 mmol, 1 eq) was dissolved in 50 mL of methanol; subsequently 10% Pd/C (180 mg, 7 weigh %) and acetic acid (0.26 ml, 4.6 mmol, 0.45 eq) were added. The mixture was stirred for 2 h under hydrogen atmosphere. Then it was filtrated though Celite, and concentrated under vacuum to give compound 5, as a light-brown solid.

Light brown solid, Mp 295-297° C., yield 98%, $C_{12}H_{12}N_2O_2$, MW 216.24, Monoisotopic Mass 216.09, $[M+H]^+$ 217.0. $^1$H NMR (300 MHz, $CD_3OD/CDCl_3$) δ (ppm) 3.60-3.62 (m, 3H) 6.59-6.60 (d, 1H, J=3.08 Hz) 6.67-6.70 (m, 2H) 6.71-6.73 (m, 1H) 7.04-7.11 (m, 2H).

1H-pyrrolo[3,2-c]quinolin-4(5H)-one (A-6)

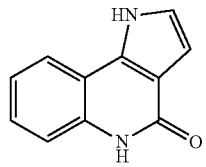 [SMILES: O=c1[nH]c2ccccc2c2[nH]ccc12]

A suspension of compound A-5 (2.5 g, 11.6 mmol, 1 eq) in sec-butanol (50 ml) and AcOH (0.5 ml, 8.7 mmol, 0.75 eq) was stirred at 70° C. for 3 h. Then a solvent was evaporated under vacuum to give the light brown solid.

Light brown solid, Mp 292-294° C., yield 99%, $C_{11}H_8N_2O$, MW 184.19, Monoisotopic Mass 184.06, $[M+H]^+$ 185.0. $^1$H NMR (300 MHz, $CD_3OD/CDCl_3$) δ (ppm) 6.81-6.82 (d, 1H, J=3.08 Hz) 7.18-7.20 (d, 1H, J=3.08 Hz) 7.23-7.30 (m, 1H) 7.36-7.45 (m, 2H) 7.95-7.98 (d, 1H, J=7.69 Hz).

4-chloro-1H-pyrrolo[3,2-c]quinoline (A-7a)

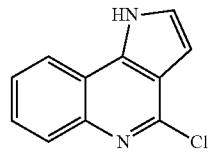 [SMILES: Clc1nc2ccccc2c2[nH]ccc12]

A mixture of lactam A-6 (1.2 g, 6.5 mmol, 1 eq) and 12 mL of $POCl_3$ was heated at 105° C. for 12 hours. It was then poured on ice and was neutralized with ammonia solution. The aqueous phase was extracted with DCM to give key synthon A-7 as a light-brown solid. The precipitate in aqueous phase was filtrated and combined with the extracted product.

Light brown solid, yield 85%, $C_{11}H_7ClN_2$, MW 202.64, Monoisotopic Mass 202.03, $[M+H]^+$ 202.9. $^1$H NMR (300 MHz, DMSO-$d_6$) δ (ppm) 6.71-6.73 (m, 1H) 7.60-7.66 (m, 3H) 7.93-7.98 (m, 1H) 8.36-8.42 (m, 1H) 12.82 (s, 1H).

The following compounds were prepared according to the above procedure:

4-chloro-8-nitro-1H-pyrrolo[3,2-c]quinoline (A-7b)

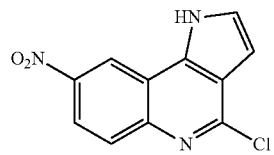 [SMILES: O=[N+]([O-])c1ccc2nc(Cl)c3cc[nH]c3c2c1]

Brown solid, yield 72%, $C_{11}H_6ClN_3O_2$, MW 247.64, Monoisotopic Mass 247.01, $[M+H]^+$ 248.0.

4-chloro-1H-pyrrolo[3,2-c]quinoline-8-carbonitrile (A-7c)

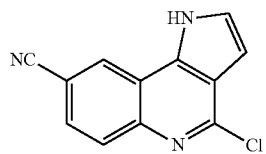 [SMILES: N#Cc1ccc2nc(Cl)c3cc[nH]c3c2c1]

Light brown solid, yield 80%, $C_{12}H_6ClN_3$, MW 227.65, Monoisotopic Mass 227.03, $[M+H]^+$ 228.0.

4-chloro-8-methoxy-1H-pyrrolo[3,2-c]quinoline (A-7d)

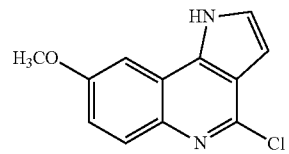 [SMILES: COc1ccc2nc(Cl)c3cc[nH]c3c2c1]

Brown solid, yield 78%, $C_{12}H_9ClN_2O$, MW 232.67, Monoisotopic Mass 232.04, $[M+H]^+$ 233.0.

4-chloro-7-fluoro-1H-pyrrolo[3,2-c]quinoline (A-7e)

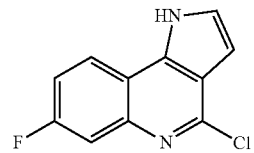 [SMILES: Fc1ccc2c(c1)nc(Cl)c1cc[nH]c12]

Brown solid, yield 75%, Mp 143-145° C., $C_{11}H_6ClFN_2$, MW 220.63, Monoisotopic Mass 220.02, $[M+H]^+$ 221.0.

4,8-dichloro-1H-pyrrolo[3,2-c]quinoline (A-7f)

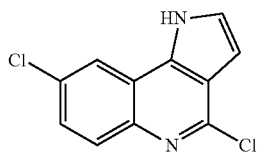 [SMILES: Clc1ccc2nc(Cl)c3cc[nH]c3c2c1]

Light brown solid, yield 81%, $C_{11}H_6Cl_2N_2$, MW 237.08, Monoisotopic Mass 235.99, $[M+H]^+$ 237.0. $^1$H NMR (300 MHz, DMSO-d$_6$) δ (ppm) 6.68-6.71 (m, 1H) 7.59-7.68 (m, 3H) 7.90-8.00 (m, $^1$H), 12.75 (s, 1H).

Example 1.2

General Procedure for Preparation of Aliphatic Amine Derivatives A-8

Procedure for Preparation of Chain Aliphatic Amine Derivative A-8a

Compound A-7 (200 mg, 1 mmol, 1 eq) was suspended in 5 ml of MeCN followed by addition of amine (539 μl, 4.9 mmol, 5 eq). The mixture was irradiated by microwave for 10 h at 140° C. The solvent was then evaporated and the mixture was purified on silica with DCM/MeOH/NH$_{3aq}$ 9/1.5/0.1 (v/v/v) as a developing solvent.

$N^1,N^1$-dimethyl-$N^2$-(1H-pyrrolo[3,2-c]quinolin-4-yl)ethane-1,2-diamine (A-8a)

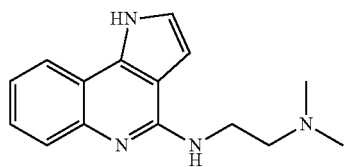 [SMILES: CN(C)CCNc1nc2ccccc2c2[nH]ccc12]

Brown oil, yield 56%, $C_{15}H_{18}N_4$, MW 254.33, Monoisotopic Mass 254.15, $[M+H]^+$255.0. $^1$H NMR (300 MHz, CD$_3$OD/CDCl$_3$) δ (ppm) 2.27-2.29 (s, 6H) 2.56-2.61 (t, 2H, J=5.90) 3.75-3.78 (t, 2H, J=5.90 Hz) 6.61-6.62 (d, 1H, J=3.08 Hz) 7.12-7.16 (m, 2H) 7.26-7.38 (m, 1H) 7.73-7.76 (d, 1H, J=8.21 Hz) 7.86-7.88 (d, 1H, J=7.95 Hz).

Procedure for Preparation of Primary Alicyclic Amine Derivatives A-8(b-g)

Compound A-7 (0.35 g, 1.7 mmol, 1 eq) was suspended in 12 ml of MeCN followed by addition of amine (6.9 mmol, 4 eq). The mixture was irradiated by microwave for 5 h at 140° C. The solvent was subsequently evaporated and the mixture was purified on silica with DCM/MeOH 9/1.5 (v/v) as a developing solvent.

tert-butyl-3-((1H-pyrrolo[3,2-c]quinolin-4-yl)amino)azetidine-1-carboxylate (A-8b)

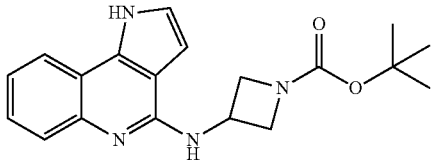 [SMILES: CC(C)(C)OC(=O)N1CC(Nc2nc3ccccc3c3[nH]ccc23)C1]

White foam, yield 57%, $C_{19}H_{22}N_4O_2$, MW 338.40, Monoisotopic Mass 338.17, $[M+H]^+$ 339.26.

tert-butyl 3-[(1H-pyrrolo[3,2-c]quinolin-4-yl)amino]pyrrolidine-1-carboxylate (A-8c)

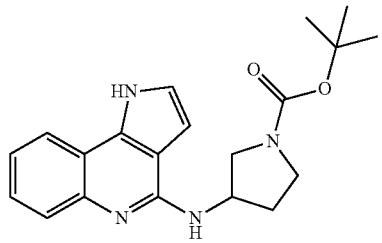 [SMILES: CC(C)(C)OC(=O)N1CCC(Nc2nc3ccccc3c3[nH]ccc23)C1]

Light brown foam, yield 60%, $C_{20}H_{24}N_4O_2$, MW 352.43, Monoisotopic Mass 352.19, $[M+H]^+$ 353.5.

(S)-tert-butyl 3-[(1H-pyrrolo[3,2-c]quinolin-4-yl)amino]pyrrolidine-1-carboxylate (A-8d)

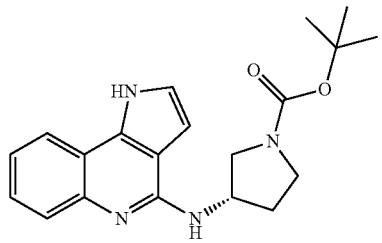 [SMILES: CC(C)(C)OC(=O)N1CC[C@H](Nc2nc3ccccc3c3[nH]ccc23)C1]

Light brown foam, yield 60%, $C_{20}H_{24}N_4O_2$, MW 352.43, Monoisotopic Mass 352.19, $[M+H]^+$ 353.2. $^1$H NMR (300 MHz, DMSO-d$_5$) δ (ppm) 1.35-1.49 (m, 9H) 1.98 (b s, 1H) 2.30 (b s, 1H) 3.27-3.56 (m, 4H) 3.71-3.81 (m, 1H) 4.93 (b s, 1H) 6.55 (d, 1H, J=3.08 Hz) 7.13 (d, 1H J=3.08 Hz) 7.16-7.23 (m, 1H) 7.25-7.27 (m, 1H) 7.33-7.34 (t, 1H, J=7.31 Hz) 7.71-7.81 (d, 1H, J=8.46 Hz) 7.86 (dd, 1H, J=7.95, 1.28 Hz).

(S)—N-(pyrrolidin-3-yl)-1H-pyrrolo[3,2-c]quinolin-4-amine (A-8d')

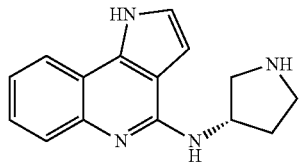 [SMILES: c1ccc2c(c1)nc(N[C@H]1CCNC1)c1cc[nH]c12]

Obtained from A-8d using a solution of 4N HCl in dioxane and isolated as a HCl salt. White solid, yield 60%, C$_{15}$H$_{16}$N$_4$, MW 252.31, Monoisotopic Mass 252.14, [M+H]$^+$ 253.1. $^1$H NMR (300 MHz, CD$_3$OD/CDCl$_3$) δ (ppm) 2.10-2.26 (m, 1H) 2.43-2.57 (m, 1H) 3.16 (m, 1H) 3.22-3.34 (m, 1H) 3.47-3.68 (m, 3H), 5.36 (b s, 1H) 7.03 (t, 2H, J=7.95 Hz) 7.28-7.37 (m, 1H) 7.47 (t, 1H, J=7.82 Hz) 7.68 (dd, 2H, J=7.82, J=4.74 Hz) 7.74-7.80 (m, 1H) 7.83 (dd, 1H, J=3.85, J=1.28 Hz).

(R)-tert-butyl 3-[(1H-pyrrolo[3,2-c]quinolin-4-yl)amino]pyrrolidine-1-carboxylate (A-8e)

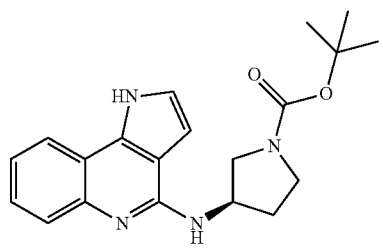 [SMILES: CC(C)(C)OC(=O)N1CC[C@@H](Nc2nc3ccccc3c3[nH]ccc23)C1]

Light brown foam, yield 62%, C$_{20}$H$_{24}$N$_4$O$_2$, MW 352.43, Monoisotopic Mass 352.19, [M+H]' 353.2. $^1$H NMR (300 MHz, DMSO-d$_5$) δ (ppm) 1.37-1.50 (m, 9H), 2.00 (b s, 1H), 2.30 (b s, 1H), 3.28-3.56 (m, 4H), 3.70-3.85 (m, 1H), 4.92 (b s, 1H), 6.50-5.58 (d, 1H, J=3.08 Hz), 7.10-7.15 (d, 1H, J=3.08 Hz), 7.17-7.24 (m, 1H), 7.25-7.28 (m, 1H), 7.34-7.43 (t, 1H, J=7.18 Hz), 7.72-7.82 (d, 1H, J=7.95 Hz), 7.83-7.90 (dd, 1H, J=7.95, J=1.03 Hz).

tert-butyl 3-[(7-fluoro-1H-pyrrolo[3,2-c]quinolin-4-yl)amino]pyrrolidine-1-carboxylate (A-A-8f)

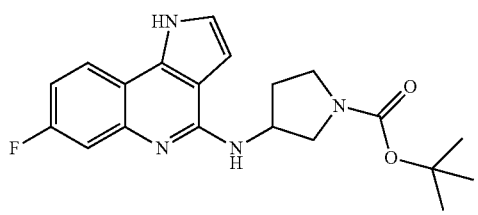 [SMILES: CC(C)(C)OC(=O)N1CCC(Nc2nc3cc(F)ccc3c3[nH]ccc23)C1]

Brown oil, yield 61%, C$_{20}$H$_{23}$FN$_4$O$_2$, MW 370.42, Monoisotopic Mass 370.18, [M+H]$^+$ 371.2.

tert-butyl 3-((8-chloro-1H-pyrrolo[3,2-c]quinolin-4-yl)amino)pyrrolidine-1-carboxylate (A-8g)

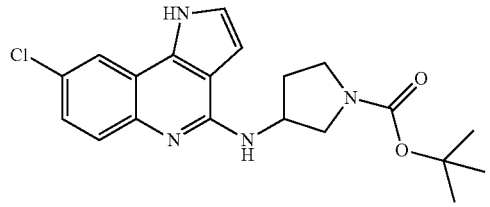 [SMILES: CC(C)(C)OC(=O)N1CCC(Nc2nc3ccc(Cl)cc3c3[nH]ccc23)C1]

Light brown foam, yield 63%, C$_{20}$H$_{23}$ClN$_4$O$_2$, MW 386.88, Monoisotopic Mass 386.15, [M+H]' 387.2.
$^1$H NMR (300 MHz, DMSO-d$_5$) δ (ppm) d ppm 1.37-1.51 (m, 9H), 2.00 (b s, 1H) 2.32 (b s, 1H) 3.28-3.57 (m, 4H) 3.71-3.81 (m, 1H) 4.92 (b s, 1H) 6.55 (d, 1H, J=3.08 Hz) 7.13 (d, 1H J=3.08 Hz) 7.20-7.24 (m, 1H) 7.26-7.28 (m, 1H) 7.71-7.81 (d, 1H, J=8.40 Hz) 7.83 (m, 1H).

Procedure for Preparation of Secondary Amine Derivatives A-8(h-q)

Compound A-7 (0.35 g, 1.7 mmol, 1 eq) was suspended in a mixture of toluene and TEA (1.4 ml, 10.2 mmol, 6 eq). Subsequently, an amine (2.4 mmol, 2 eq) was added and the reaction was stirred at 114° C. for 14 hours. For homopiperazine derivatives the reaction was assisted by the microwave irradiation at 140° C. for 6 hours. The reaction mixture was evaporated, the remaining crude product was purified on silica gel with respective eluents: AcOEt/Hex 4/6 (v/v) for Boc-N-methylpyrrolidin-3-amine and Boc-piperazine derivatives, and DCM/MeOH 9/1.5 (v/v) for methylpiperazine, benzylpiperazine and homopiperazine.

tert-butyl (1-(1H-pyrrolo[3,2-c]quinolin-4-yl)pyrrolidin-3-yl)(methyl)carbamate (A-8 h)

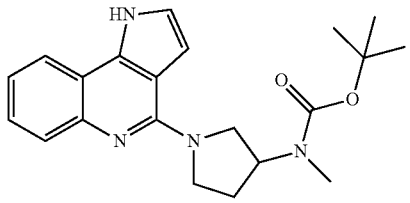 [SMILES: CN(C(=O)OC(C)(C)C)C1CCN(c2nc3ccccc3c3[nH]ccc23)C1]

Brown oil, yield 67%, C$_{21}$H$_{26}$N$_4$O$_2$, MW 366.46, Monoisotopic Mass 366.21, [M+H]$^+$ 367.2.

tert-butyl 4-(1H-pyrrolo[3,2-c]quinolin-4-yl)piperazine-1-carboxylate (A-8i)

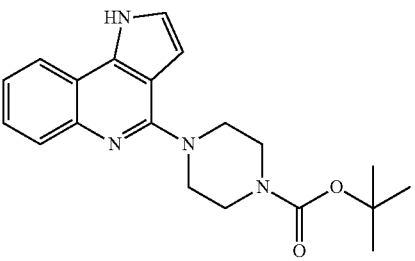 [SMILES: CC(C)(C)OC(=O)N1CCN(c2nc3ccccc3c3[nH]ccc23)CC1]

Light brown foam, yield 63%, C$_{20}$H$_{24}$N$_4$O$_2$, MW 352.43, Monoisotopic Mass 352.19, [M+H]$^+$ 353.4. $^1$H NMR (300 MHz, CDCl$_3$) δ (ppm) 3.45-3.55 (m, 4H) 3.57-3.66 (m, 4H) 6.45-6.46 (d, 1H, J=3.07 Hz) 7.03-7.08 (d, 1H, J=3.34 Hz) 7.09-7.15 (m, 1H) 7.56-7.64 (d, 1H, J=7.95 Hz) 7.82-7.86 (dd, 1H, J=1.01 Hz, J=7.95 Hz).

4-(piperazin-1-yl)-1H-pyrrolo[3,2-c]quinoline (A-8i')

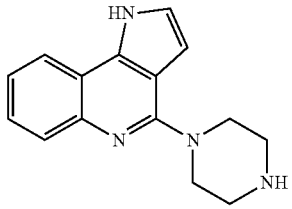 [SMILES: c1ccc2c(c1)nc(N1CCNCC1)c1cc[nH]c12]

Obtained from A-8i using a solution of 4N HCl in dioxane and isolated as a HCl salt. White solid, yield 100%, C$_{15}$H$_{16}$N$_4$, MW 252.31, Monoisotopic Mass 252.14, [M+H]+=253.1. $^1$H NMR (300 MHz, CD$_3$OD/CDCl$_3$) δ (ppm) 2.55-2.59 (t, 4H, J=5.17 Hz) 3.82-3.87 (t, 4H, J=4.90 Hz) 6.64-6.68 (m, 1H) 7.17-7.29 (m, 2H) 7.34-7.41 (m, 1H) 7.79-7.84 (m, 2H).

4-(4-methylpiperazin-1-yl)-1H-pyrrolo[3,2-c]quinoline (A-8j)

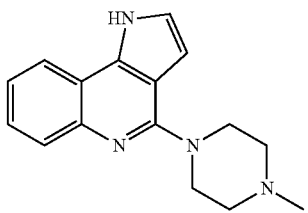 [SMILES: CN1CCN(c2nc3ccccc3c3[nH]ccc23)CC1]

Light brown foam, yield 62%, C$_{16}$H$_{18}$N$_4$, MW 266.34, Monoisotopic Mass 266.15, [M+H]$^+$ 267.4. $^1$H NMR (300 MHz, CD$_3$OD/CDCl$_3$) δ (ppm) 2.33 (s, 3H) 260-2.64 (t, 4H, J=5.12 Hz) 3.87-3.90 (t, 4H, J=4.87 Hz) 6.64-6.64 (d, 1H, J=3.07 Hz) 7.15-7.26 (m, 2H) 7.36-7.42 (m, 1H) 7.83-7.87 (m, 2H).

4-(4-benzylpiperazin-1-yl)-1/1-pyrrolo[3,2-c]quinoline (A-8k)

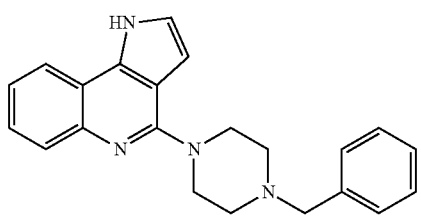 [SMILES: c1ccc(CN2CCN(c3nc4ccccc4c4[nH]ccc34)CC2)cc1]

Brown oil, yield 55%, C$_{22}$H$_{22}$N$_4$, MW 342.44, Monoisotopic Mass 342.18, [M+H]$^+$ 343.5. $^1$H NMR (300 MHz, CD$_3$OD/CDCl$_3$) δ (ppm) 2.66-2.69 (t, 4H, J=4.87 Hz) 3.61 (s, 2H) 3.87-3.90 (t, 4H, J=4.87 Hz) 6.68-6.70 (m, 1H) 7.17-7.19 (m, 1H) 7.24-7.49 (m, 7H) 7.78-7.86 (m, 2H).

tert-butyl 4-(8-nitro-1H-pyrrolo[3,2-c]quinolin-4-yl)piperazine-1-carboxylate (A-8l)

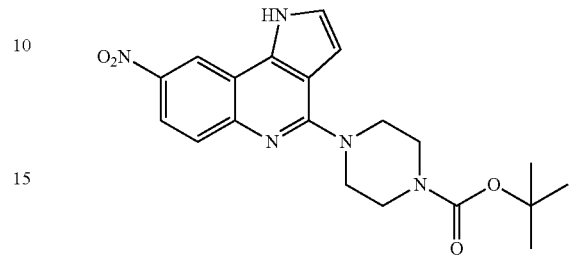

Yellow oil, yield 62%, C$_{20}$H$_{23}$N$_5$O$_4$, MW 397.43, Monoisotopic Mass 397.18, [M+H]$^+$ 398.2.

tert-butyl 4-(8-amino-1H-pyrrolo[3,2-c]quinolin-4-yl)piperazine-1-carboxylate (A-8m)

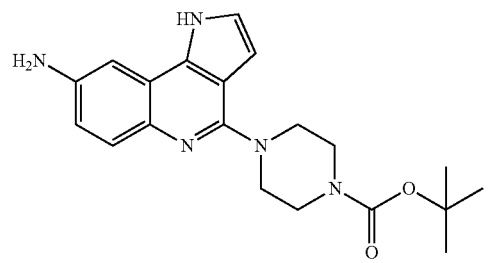 [SMILES: CC(C)(C)OC(=O)N1CCN(c2nc3ccc([N+](=O)[O-])cc3c3[nH]ccc23)CC1]

Obtained from A-9l under palladium-catalyzed reduction. Compound A-9l (300 mg, 0.82 mmol) was dissolved in methanol, and subsequently, 10% Pd/C (30 mg, 10 weigh %) and acetic acid (21 μl, 0.37 mmol, 0.45 eq) were added. The mixture was stirred for 2 h under hydrogen atmosphere. Then, it was filtrated though Celite, and concentrated under vacuum. The remaining crude was purified on silica with AcOEt/Hex 5/5 as developing solvent.

Brown oil, C$_{20}$H$_{25}$N$_5$O$_2$, yield 62%, MW 367.44, Monoisotopic Mass 367.20, [M+H]$^+$ 368.2.

tert-butyl 4-(8-cyano-1H-pyrrolo[3,2-c]quinolin-4-yl)piperazine-1-carboxylate (A-8n)

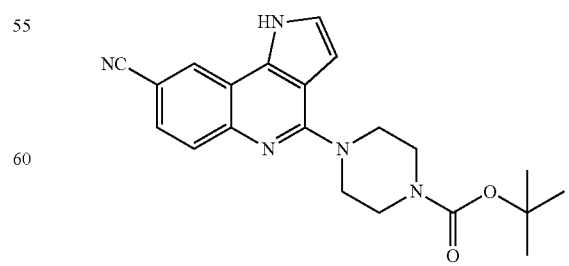

Brown oil, yield 59%, C$_{21}$H$_{23}$N$_5$O$_4$, MW 377.44, Monoisotopic Mass 377.19, [M+H]$^+$ 378.2.

29 tert-butyl 4-(8-methoxy-1H-pyrrolo[3,2-c]quinolin-4-yl)piperazine-1-carboxylate (A-8o)

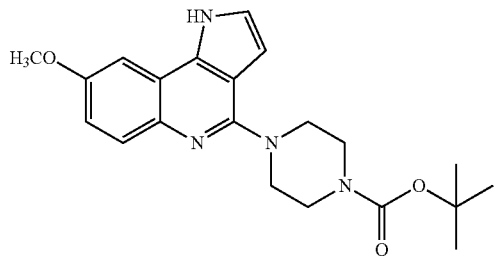 [SMILES: COc1ccc2nc(N3CCN(C(=O)OC(C)(C)C)CC3)c3cc[nH]c3c2c1]

Light brown foam, yield 64%, $C_{21}H_{26}N_4O_3$, MW 382.46, Monoisotopic Mass 382.20, [M+H]$^+$ 383.2.

tert-butyl 4-(8-chloro-1H-pyrrolo[3,2-c]quinolin-4-yl)piperazine-1-carboxylate (A-8p)

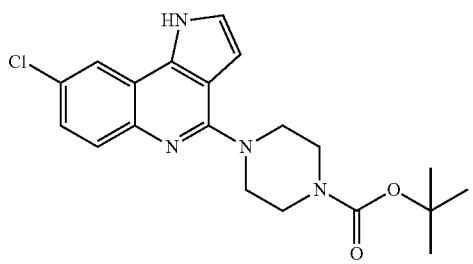 [SMILES: CC(C)(C)OC(=O)N1CCN(c2nc3ccc(Cl)cc3c3[nH]ccc23)CC1]

Brown oil, yield 65%, $C_{20}H_{23}ClN_4O_2$, MW 386.88, Monoisotopic Mass 386.15, [M+H]$^+$ 387.2.

8-chloro-4-(piperazin-1-yl)-1H-pyrrolo[3,2-c]quinoline (A-8p')

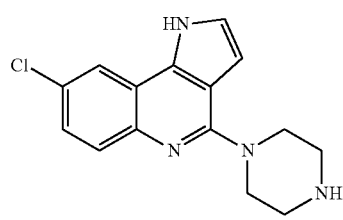 [SMILES: Clc1ccc2nc(N3CCNCC3)c3cc[nH]c3c2c1]

Obtained from A-8p using a solution of 4N HCl in dioxane and isolated as a HCl salt. White solid, $C_{15}H_{15}ClN_4$, MW 286.76, Monoisotopic Mass 286.10, [M+H]$^+$ 287.1

$^1$H NMR (300 MHz, CD$_3$OD/CDCl$_3$) δ (ppm) 2.56-2.59 (t, 4H, J=5.19 Hz) 3.83-3.89 (t, 4H, J=4.87 Hz) 6.65-6.67 (m, 1H) 7.19-7.30 (m, 1H) 7.32-7.39 (m, 1H) 7.80-7.84 (m, 2H).

30 tert-butyl 4-(7-fluoro-1H-pyrrolo[3,2-c]quinolin-4-yl)piperazine-1-carboxylate (A-8q)

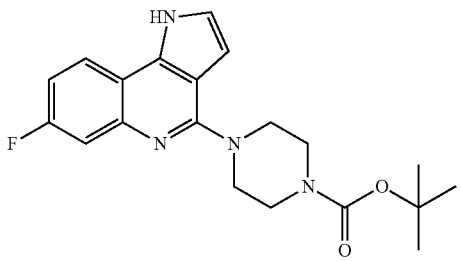 [SMILES: CC(C)(C)OC(=O)N1CCN(c2nc3cc(F)ccc3c3[nH]ccc23)CC1]

Brown oil, yield 60%, $C_{20}H_{23}FN_4O_2$, MW 370.42, Monoisotopic Mass 370.18, [M+H]$^+$ 371.2.

tert-butyl 4-(1H-pyrrolo[3,2-c]quinolin-4-yl)-1,4-diazepane-1-carboxylate (A-8r)

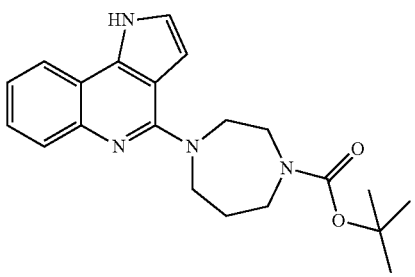 [SMILES: CC(C)(C)OC(=O)N1CCCN(c2nc3ccccc3c3[nH]ccc23)CC1]

Light brown foam, yield 85%, $C_{21}H_{26}N_4O_2$, MW 366.46, Monoisotopic Mass 366.21, [M+H]$^+$ 367.2.

4-(1,4-diazepan-1-yl)-1H-pyrrolo[3,2-c]quinoline (A-8r')

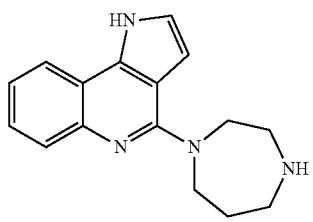 [SMILES: c1ccc2c(c1)nc(N1CCCNCC1)c1cc[nH]c12]

Obtained from A-8r using a solution of 4N HCl in dioxane and isolated as a HCl salt. White solid, yield 85%, $C_{16}H_{18}N_4$, MW 266.34, Monoisotopic Mass 266.15, [M+H]$^+$ 267.2.

$^1$H NMR (300 MHz, CD$_3$OD/CDCl$_3$) δ (ppm) 1.64-1.67 (m, 2H), 2.55-2.57 (m, 2H), 2.78-2.82 (m, 2H), 3.18-3.22 (m, 2H), 3.68-3.42 (m, 2H), 6.42-6.45 (d, 1H, J=3.07 Hz), 7.02-7.10 (m, 1H), 7.36-7.39 (m, 1H), 7.68-7.75 (m, 1H), 7.83-7.89 (m, 1H), 8.00-8.12 (m, 1H).

4-(piperidin-1-yl)-1H-pyrrolo[3,2-c]quinoline (A-8s)

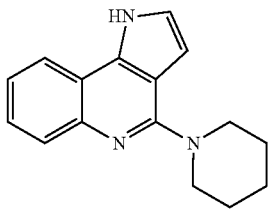 [SMILES: c1ccc2c(c1)nc(N1CCCCC1)c1cc[nH]c12]

Compound A-7 (180 mg, 0.89 mmol, 1 eq) was suspended in toluene (3 ml) and added the respective amine (3.56 mmol, 4 eq). The mixture was irradiated by microwave at 125° C. for 1 h. The solvent was evaporated and the remaining crude was purified on silica with AcOEt/Hex 4/6 as a developing solvent.

Yellow foam, yield 60%, $C_{16}H_{17}N_3$, MW 251.33, Monoisotopic Mass 251.14. $^1$H NMR (300 MHz, CDCl$_3$) δ (ppm) 1.62-1.79 (m, 6H) 3.33 (s, 4H) 6.72 (b s, 1H) 7.25-7.33 (m, 1H) 7.38-7.47 (m, 2H) 7.66-7.74 (d, 1H, J=8.22 Hz) 8.16-8.22 (dd, 1H, J=8.02, J=1.17 Hz) 12.35-12.44 (m, 1H).

4-(1H-pyrrolo[3,2-c]quinolin-4-yl)morpholine (A-8t)

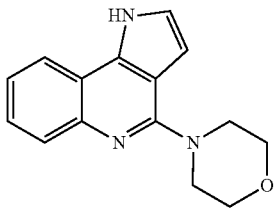 [SMILES: c1ccc2c(c1)nc(N1CCOCC1)c1cc[nH]c12]

Compound A-7 (180 mg, 0.89 mmol, 1 eq) was suspended in toluene (3 ml) and added the respective amine (3.56 mmol, 4 eq). The mixture was irradiated by microwave at 125° C. for 1 h. The solvent was evaporated and the remaining crude was purified on silica with AcOEt/Hex 4/6 as a developing solvent.

Light brown foam, yield 62%, $C_{15}H_{15}N_3O$, MW 253.30, Monoisotopic Mass 253.12. $^1$H NMR (300 MHz, CDCl$_3$) δ (ppm) 3.65-3.74 (m, 4H) 3.78-3.87 (m, 4H) 6.74-6.78 (dd, 1H, J=3.13, J=1.76 Hz) 7.27-7.33 (m, 1H) 7.38-7.45 (m, 2H) 7.64-7.70 (m, 1H) 8.14-8.21 (m, 1H) 12.29 (b s, 1H).

Example 1.3

General Procedure for Preparation of the Ether Derivatives A-8(w,x)

Compound A-7 (400 mg, 2 mmol, 1 eq) was dissolved in DMF and added Cs$_2$CO$_3$ (775 mg, 2.38 mmol, 1.2 eq). Benzyl bromide (270 μl, 2.18 mmol, 1.1 eq) was added dropwisely. The reaction was conducted at room temperature for 30 min. Then, the mixture was diluted with AcOEt, washed with water (3×) and brine (1×), dried over Na$_2$SO$_4$, filtrated and concentrated under reduced pressure. The remaining crude was purified on chromatographic column with AcOEt/Hex 2/8 (v/v) as a developing solvent. The obtained compound A-8u (500 mg, 1.71 mmol, 1 eq) was mixed together with Pd$_2$(dba)$_3$ (31 mg, 0.03 mmol, 0.02 eq), BINAP (42 mg, 0.07 mmol, 0.04 eq) and t-BuOK (268 mg, 2.4 mmol, 1.4 eq). The mixture was suspended in toluene (10 ml) and 1-Boc-3-hydroxypyrrolidine (382 mg, 2.00 mmol, 1.2 eq) was added. The reaction was irradiated by microwave at 115° C. for 1 h. The resulting mixture was concentrated and purified on silica gel using AcOEt/Hex 3/7 (v/v) as a developing solvent. Compound A-8w (620 mg, 1.40 mmol, 1 eq) was suspended in DMSO, and t-BuOK (1.25 g, 11.2 mmol, 8 eq) was added as a solid. The flask was placed in the oil bath and the air was bubbled into the mixture. The reaction was carried out at 70° C. for 30 min to obtain deprotected ether derivative A-9x. Next, the mixture was diluted with water and was extracted AcOEt (3×40 mL). After drying over MgSO$_4$ it was concentrated and purified on the silica with AcOEt/Hex 4/6 (v/v) as a developing solvent.

1-benzyl-4-chloro-1H-pyrrolo[3,2-c]quinoline (A-8u)

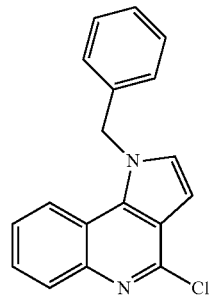 [SMILES: Clc1nc2ccccc2c2c1ccn2Cc1ccccc1]

White foam, yield 80%, $C_{18}H_{13}ClN_2$, MW 292.76, Monoisotopic Mass 292.08, [M+H]$^+$ 293.20.

tert-butyl 3-((1-benzyl-1H-pyrrolo[3,2-c]quinolin-4-yl)oxy)pyrrolidine-1-carboxylate (A-8w)

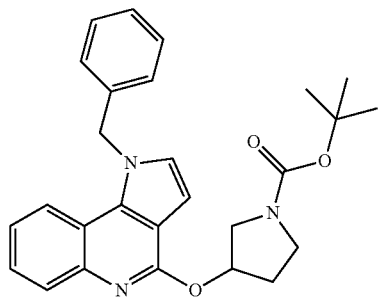 [SMILES: CC(C)(C)OC(=O)N1CCC(Oc2nc3ccccc3c3c2ccn3Cc2ccccc2)C1]

White foam, yield 91%, $C_{27}H_{29}N_3O_3$, MW 443.54, Monoisotopic Mass 443.22, $[M+H]^+$ 444.1.

tert-butyl 3-((1H-pyrrolo[3,2-c]quinolin-4-yl)oxy)pyrrolidine-1-carboxylate (A-9x)

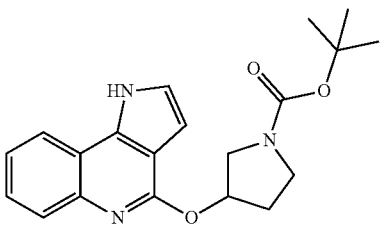 [SMILES: CC(C)(C)OC(=O)N1CCC(Oc2nc3ccccc3c3[nH]ccc23)C1]

White foam, yield 90%, $C_{20}H_{23}N_3O_3$, MW 353.41, Monoisotopic Mass 353.17, $[M+H]^+$ 354.2.

Example 1.4

General Procedure for Preparation of Pyrrolo[3,2-C]quinoline Derivatives of General structure A-9

Compound A-8 (0.28 mmol, 1 eq) was dissolved in DCM (5 ml). The mixture was placed in the ice-bath and sulfonyl chloride or arylacyl chloride or arytalkyl halide (0.50 mmol, 1.8 eq) was added in portions. The reaction was carried out in the presence of a strong base chosen from potassium tert-butoxide, sodium hydride, cesium carbonate or BTPP and was performed for 3 h. Subsequently, the mixture was evaporated and the remaining yellow crude was purified on silica get. All the Boc-protected arylsulfonamide, arylamide and arytalkyl derivatives of 1H-pyrrolo[3,2-c]quinolines of general structure A-9 were characterized by LC-MS and $^1$H NMR methods (data given for representative compounds 5', 21', 27', 29', 43', 46', 48'). They were further deprotected using 4N HCl solution in dioxane to yield the final arytsulfonamide derivatives of amine/ether-substituted pyrroloquinolines A-9.

| | | | |
|---|---|---|---|
| 1 | N1,N1-dimethyl-N2-(1-(phenylsulfonyl)-1H-pyrrolo[3,2-c]quinolin-4-yl)ethane-1,2-diamine | The title compound was prepared starting from amine A-9a and benzenesulfonyl chloride. Yield 60%, $C_{21}H_{22}N_4O_2S$, MW 394.49, Monoisotopic Mass 394.15, $[M + H]^+$ 395.0 | $^1$H NMR (300 MHz, CD$_3$OD) δ (ppm) 2.50 (s, 6 H), 2.80-2.86 (t, 2 H, J = 5.82 Hz), 3.82-3.85 (t, 2 H, J = 5.82 Hz), 7.15-7.17 (m, 1 H), 7.35-7.40 (m, 2 H), 7.55-7.57 (m, 2 H), 7.64-7.68 (m, 2 H), 7.82-7.86 (m, 2 H), 7.93-7.94 (m, 1 H), 8.76-8.77 (m, 1 H) |
| 2 | 1-((3-chlorophenyl)sulfonyl)-N-(azetidin-3-yl)-1H-pyrrolo[3,2-c]quinolin-4-amine | The title compound was prepared starting from amine A-9b and 3-chlorobenzenesulfonyl chloride, and isolated as HCl salt. Yield, 62%, $C_{20}H_{17}ClN_4O_2S$, MW 412.89, Monoisotopic Mass 412.08, $[M + H]^+$ 413.1 | $^1$H NMR (300 MHz, DMSO-d$_6$) δ (ppm) 2.5 (b s , 1 H), 3.35-3.45 (m, 1 H), 3.60-3.87 (m, 4 H), 4.29 (b s, 1 H), 6.39-6.43 (d, 1 H, J = 7.5 Hz), 7.25-7.29 (s, 1 H, J = 7.5 Hz), 7.37-7.39 (m, 1 H), 7.47-7.51 (m, 1 H), 7.65-7.80 (m, 4 H), 8.15-8.20 (m, 1 H), 8.23 (s, 1 H) |
| 3 | 1-(naphthalen-1-ylsulfonyl)-N-(azetidin-3-yl)-1H-pyrrolo[3,2-c]quinolin-4-amine | The title compound was prepared starting from amine A-9b and 1-naphtalenesulfonyl chloride, and isolated as HCl salt. Yield 64%, $C_{24}H_{20}N_4O_2S$, MW 428.51, Monoisotopic Mass 428.13, $[M + H]^+$ 429.1 | |
| 4 | 1-(phenylsulfonyl)-N-(pyrrolidin-3-yl)-1H-pyrrolo[3,2-c]quinolin-4-amine | The title compound was prepared starting from amine A-9c and benzenesulfonyl chloride, and isolated as HCl salt. Yield, 80%, $C_{21}H_{20}N_4O_2S$, MW 392.47, Monoisotopic Mass 392.13, $[M + H]^+$ 393.1 | |
| 5 | 1-((3-chlorophenyl)sulfonyl)-N-(pyrrolidin-3-yl)-1H-pyrrolo[3,2-c]quinolin-4-amine | The title compound was prepared starting from amine A-9c and 3-chlorobenzenesutfonyl chloride, and isolated as HCl salt. Yield 90%, $C_{21}H_{19}ClN_4O_2S$, MW 426.92, Monoisotopic Mass 426.09, $[M + H]^+$ 427.3 | |
| 5' | tert-butyl 3-((1-((3-chlorophenyl)sulfonyl)-1H-pyrrolo[3,2-c]quinolin-4-yl)amino)pyrrolidine-1-carboxylate | The title compound was prepared starting from amine A-9c and 3-chloro-benzenesulfonyl chloride. Yield 90%, $C_{26}H_{27}ClN_4O_4S$, MW 527.03, Monoisotopic Mass 526.14, $[M + H]^+$ 527.22. | $^1$H NMR (300 MHz, CDCl$_3$) δ (ppm) 1.50 (s, 9 H), 2.05-2.08 (m, 2 H), 2.17-2.18 (m, 1 H), 3.19-3.38 (m, 1 H), 3.49-3.70 (m, 2 H), 3.83-3.90 (m, 1 H), 4.88-4.91 (b s, 1 H), 6.71-6.73 (d, 1 H, J = 3.85 Hz), |

-continued

| # | Compound | Preparation | ¹H NMR |
|---|---|---|---|
| | | | 7.21-7.27-7.35 (m, 2 H), 7.44-49 (m, 2 H), 7.54-7.60 (m, 1 H), 7.69-7.80 (m, 2 H), 7.86-7.87 (d, 1 H, J = 3.59 Hz), 8.70-8.74 (dd, 1 H, J = 8.60 Hz, J = 1.02 Hz) |
| 6 | (S)-1-((3-chlorophenyl)sulfonyl)-N-(pyrrolidin-3-yl)-1H-pyrrolo[3,2-c]quinolin-4-amine | The title compound was prepared starting from amine A-9d and 3-chlorobenzenesulfonyl chloride, and isolated as HCl salt. Yield 92%, Mp 211-21° C., $C_{21}H_{19}ClN_4O_2S$, MW 426.92, Monoisotopic Mass 426.09. [M + H]⁺ 427.2 | ¹H NMR (300 MHz, $CD_3OD/CDCl_3$) δ (ppm) 2.24-2.40 (m, 1 H) 2.52-2.69 (m, 1 H) 3.27-3.44 (m, 2 H) 3.56-3.79 (m, 3 H) 5.46-5.68 (m, 1 H) 7.32-7.64 (m, 5 H) 7.69-7.73 (t, 1 H, J = 1.79 Hz) 7.85-8.01 (m, 2 H) 8.44-8.53 (d, 1 H, J = 8.25 Hz) 8.72-8.79 (dd, 1 H, J = 8.53, J = 1.10 Hz) |
| 7 | (R)-1-((3-chlorophenyl)sulfonyl)-N-(pyrrolidin-3-yl)-1H-pyrrolo[3,2-c]quinolin-4-amine | The title compound was prepared starting from amine A-9e and 3-chlorobenzenesulfonyl chloride, and isolated as HCl salt. Yield 91%, 221-223, $C_{21}H_{19}ClN_4O_2S$, MW 426.92, Monoisotopic Mass 426.09, [M + H]⁺ 427.2 | ¹H NMR (300 MHz, $CD_3OD/CDCl_3$) δ (ppm) 2.25-2.38 (m, 1 H) 2.54-2.68 (m, 1 H) 3.23-3.35 (m, 1 H) 3.38-3.43 (m, 1 H) 3.57-3.76 (m, 3 H) 5.50-5.64 (m, 1 H) 7.29-7.63 (m, 5 H) 7.68-7.73 (t, 1 H, J = 1.80 Hz) 7.84-7.98 (m, 2 H) 8.41-8.49 (d, 1 H, J = 8.46 Hz) 8.72-8.78 (dd, 1 H, J = 8.59, J = 1.15 Hz) |
| 8 | 1-((3-fluorophenyl)sulfonyl)-N-(pyrrolidin-3-yl)-1H-pyrrolo[3,2-c]quinolin-4-amine | The title compound was prepared starting from amine A-9c and 3-fluorobenzenesulfonyl chloride, and isolated as HCl salt. Yield 89%, $C_{21}H_{19}FN_4O_2S$, MW 410.46, Monoisotopic Mass 410.12 [M + H]⁺ 411.2 | |
| 9 | (S)-1-((3-fluorophenyl)sulfonyl)-N-(pyrrolidin-3-yl)-1H-pyrrolo[3,2-c]quinolin-4-amine | The title compound was prepared starting from amine A-9d and 3-fluorobenzenesulfonyl chloride, and isolated as HCl salt. Yield 85%, $C_{21}H_{19}FN_4O_2S$, MW 410.46, Monoisotopic Mass 410.12 [M + H]⁺ 411.2 | |
| 10 | (R)-1-((3-fluorophenyl)sulfonyl)-N-(pyrrolidin-3-yl)-1H-pyrrolo[3,2-c]quinolin-4-amine | The title compound was prepared starting from amine A-9e and 3-fluorobenzenesulfonyl chloride, and isolated as HCl salt. Yield 90%, $C_{21}H_{19}FN_4O_2S$, MW 410.46, Monoisotopic Mass 410.12 [M + H]⁺ 411.2 | |
| 11 | 1-((4-fluorophenyl)sulfonyl)-N-(pyrrolidin-3-yl)-1H-pyrrolo[3,2-c]quinolin-4-amine | The title compound was prepared starting from amine A-9c and 4-fluorobenzenesulfonyl chloride, and isolated as HCl salt. Yield 88%, $C_{21}H_{19}FN_4O_2S$, MW 410.46, Monoisotopic Mass 410.12, [M + H]⁺ 411.3 | ¹H NMR (300 MHz, $CD_3OD/CDCl_3$) δ (ppm) 2.10-2.26 (m, 1 H) 2.43-2.57 (m, 1 H) 3.15-3.18 (m, 1 H) 3.22-3.34 (m, 1 H) 3.47-3.68 (m, 3 H) 5.36 (b s, 1 H) 7.00-7.05 (t, 2 H, J = 7.95 Hz) 7.28-7.37 (m, 1 H) 7.44-7.50 (t, 1 H, J = 7.82 Hz) 7.62-7.71 (dd, 2 H, J = 7.82, J = 4.74 Hz) 7.74-7.80 (m, 1 H) 7.82-7.84 (dd, 1 H, J = 3.85, J = 1.28 Hz) 8.26-8.29 (d, 1 H, J = 8.46 Hz) 8.67-8.74 (d, 1 H, J = 8.72 Hz) |
| 12 | 1-((2,5-difluorophenyl)sulfonyl)-N-(pyrrolidin-3-yl)-1H-pyrrolo[3,2-c]quinolin-4-amine | The title compound was prepared starting from amine A-9c and 2,5-difluoro-benzenesulfonyl chloride, and isolated as HCl salt. Yield 79%, $C_{21}H_{18}F_2N_4O_2S$, MW 428.46, Monoisotopic Mass 428.11, [M + H]⁺ 429.0 | |
| 13 | 1-((3-methoxyphenyl)sulfonyl)-N-(pyrrolidin-3-yl)-1H-pyrrolo[3,2-c]quinolin-4-amine | The title compound was prepared starting from amine A-9c and 3-methoxybenzenesulfonyl chloride, and isolated as HCl salt. Yield 95%, $C_{22}H_{22}N_4O_3S$, MW 422.50, Monoisotopic Mass 422.14. [M + H]⁺ 423.2 | ¹H NMR (300 MHz, DMSO-$d_6$) δ (ppm) 2.37-2.43 (m, 3 H) 2.62-2.72 (m, 4 H) 3.67-3.78 (m, 4 H) 6.88-6.89 (d, 1 H, J = 3.85 Hz) 7.04-7.1 (m, 1 H) 7.29-7.44 (m, 1 H) 7.57-7.75 (m, 3 H) 7.79-7.82 (dd, 1 H, J = 8.46, J = 0.77 Hz) |

| | | | 7.87-7.93 (m, 1 H) 7.97-8.04 (m, 1 H) 8.44-8.50 (dd, 1 H, J = 8.46, J = 0.77 Hz) 8.56-8.63 (m, 1 H) |
|---|---|---|---|
| 14 | 1-((3-(trifluoromethyl)phenyl)sulfonyl)-N-(pyrrolidin-3-yl)-1H-pyrrolo[3,2-c]quinolin-4-amine | The title compound was prepared starting from amine A-9c and 3-(trifluoromethyl) benzenesulfonyl chloride, and isolated as HCl salt. Yield 90%, $C_{22}H_{19}F_3N_4O_2S$, MW 460.47, Monoisotopic Mass 460.12, $[M + H]^+$ 461.3 | |
| 15 | (S)-1-((3-(trifluoromethyl)phenyl)sulfonyl)-N-(pyrrolidin-3-yl)-1H-pyrrolo[3,2-c]quinolin-4-amine | The title compound was prepared starting from amine A-9d and 3-(trifluoromethyl)-benzenesulfonyl chloride, and isolated as HCl salt. Yield 91%, $C_{22}H_{19}F_3N_4O_2S$, MW 460.47, Monoisotopic Mass 460.12, $[M + H]^+$ 461.3 | |
| 16 | (R)-1-((3-(trifluoromethyl)phenyl)sulfonyl)-N-(pyrrolidin-3-yl)-1H-pyrrolo[3,2-c]quinolin-4-amine | The title compound was prepared starting from amine A-9e and 3-(trifluoromethyl)-benzenesulfonyl chloride, and isolated as HCl salt. Yield 88%, $C_{22}H_{19}F_3N_4O_2S$, MW 460.47, Monoisotopic Mass 460.12, $[M + H]^+$ 461.3 | |
| 17 | 1-((4-(tert-butyl)phenyl)sulfonyl)-N-(pyrrolidin-3-yl)-1H-pyrrolo[3,2-c]quinolin-4-amine | The title compound was prepared starting from amine A-9c and 4-tert-butylbenzene-sulfonyl chloride, and isolatd as HCl salt. Yield 78%, $C_{25}H_{28}N_4O_2S$, MW 448.58, Monoisotopic Mass 448.19, $[M + H]^+$ 449.3 | $^1$H NMR (300 MHz, CD$_3$OD/CDCl$_3$) δ (ppm) 1.17 (s, 9 H) 2.23-2.39 (m, 1 H) 2.53-2.70 (m, 1 H) 3.28 (b s, 2 H) 3.62 (b s, 3 H) 5.49-5.64 (m, 1 H) 7.26 (s, 1 H) 7.32-7.46 (m, 2 H) 7.49-7.70 (m, 3 H) 7.80-7.92 (m, 2 H) 8.36-8.49 (m, 1 H) 8.83-8.86 (d, 1 H, J = 8.53 Hz) |
| 18 | 1-((4-aminophenyl)sulfonyl)-N-(pyrrolidin-3-yl)-1H-pyrrolo[3,2-c]quinolin-4-amine | The title compound was prepared starting from amine A-9c and 4-aminobenzene-sulfonyl chloride, and isolated as HCl salt. Yield 66%, $C_{21}H_{21}N_5O_2S$, MW 407.49, Monoisotopic Mass 407.14, $[M + H]^+$ 408.2 | |
| 19 | (S)-1-((4-aminophenyl)sulfonyl)-N-(pyrrolidin-3-yl)-1H-pyrrolo[3,2-c]quinolin-4-amine | The title compound was prepared starting from amine A-9d and 4-aminobenzene-sulfonyl chloride, and isolated as HCl salt. Yield 67%, $C_{21}H_{21}N_5O_2S$, MW 407.49, Monoisotopic Mass 407.14, $[M + H]^+$ 408.2 | |
| 20 | (R)-1-((4-aminophenyl)sulfonyl)-N-(pyrrolidin-3-yl)-1H-pyrrolo[3,2-c]quinolin-4-amine | The title compound was prepared starting from amine A-9e and 4-aminobenzene-sulfonyl chloride, and isolated as HCl salt. Yield 66%, $C_{21}H_{21}N_5O_2S$, MW 407.49, Monoisotopic Mass 407.14, $[M + H]^+$ 408.2 | $^1$H NMR (300 MHz, CD$_3$OD/CDCl$_3$) δ (ppm) 2.25-2.37 (m, 1 H) 2.48-2.62 (m, 4 H) 3.70-3.82 (m, 2 H) 6.88-6.89 (d, 1 H, J = 3.92 Hz) 7.09-7.15 (m, 1 H) 7.29-7.47 (m, 1 H) 7.63-7.78 (m, 3 H) 7.80-7.86 (m, 1 H), 7.90-7.97 (m, 1 H) 8.01-8.06 (m, 1 H) 8.52-8.58 (dd, 1 H, J = 9.30 Hz, J = 0.80 Hz) 8.64-8.67 (m, 1 H) |
| 21 | 1-(naphthalen-1-ylsulfonyl)-N-(pyrrolidin-3-yl)-1H-pyrrolo[3,2-c]quinolin-4-amine | The title compound was prepared starting from amine A-9c and 1-naphtalenesulfonyl chloride, and isolated as HCl salt. Yield 88%, $C_{25}H_{22}N_4O_2S$, MW 442.53, Monoisotopic Mass 442.15, $[M + H]^+$ 443.3 | $^1$H NMR (300 MHz, CD$_3$OD/CDCl$_3$) δ (ppm) 2.17-2.31 (m, 1 H), 2.41-2.56 (m, 5 H), 3.25-3.40 (d, 1 H, J = 5.39 Hz) 5.42 (b s, 1 H), 7.21-7.34 (t, 1 H, J = 7.69 Hz) 7.47-7.72 (m, 4 H) 7.99-8.08 (m, 2 H) 8.10-8.15 (d, 1 H, J = 3.85 Hz) 8.16-8.21 (d, 1 H, J = 7.44 Hz) 8.22-8.26 (d, 1 H, J = 8.21 Hz,) 8.28-8.35 (d, 1 H, J = 8.46 Hz) 8.36-8.46 (d, 1 H, J = 5.90 Hz) 8.48-8.55 (d, 1 H, J = 7.69 Hz) |

| | | |
|---|---|---|
| 21' tert-butyl 3-((1/-(naphthalen-1-ylsulfonyl)-1H-pyrrolo[3,2-c]quinolin-4-yl)amino)pyrrolidine-1-carboxylate | The title compound was prepared starting from amine A-9c and 1-naphtalenesulfonyl chloride. Yield 88%, C$_{30}$H$_{30}$N$_4$O$_4$S, MW 542.65, Monoisotopic Mass 542.20, [M + H]$^+$ 543.27 | / |
| 22 1-(quinolin-8-ylsulfonyl)-N-(pyrrolidin-3-yl)-1H-pyrrolo[3,2-c]quinolin-4-amine | The title compound was prepared starting from amine A-9c and 8-quinolinesulfonyl chloride, and isolated as HCl salt. Yield 86%, C$_{24}$H$_{21}$N$_5$O$_2$S, MW 443.52, Monoisotopic Mass 443.14, [M + H]$^+$ 444.2 | $^1$H NMR (300 MHz, CD$_3$OD/CDCl$_3$) δ (ppm) 2.17-2.33 (m, 1 H) 2.48-2.63 (m, 1 H) 3.28-30 (m, 3 H) 3.56 (b s, 2 H) 5.39-5.55 (m, 1 H) 7.27-7.52 (m, 2 H) 7.57-7.76 (m, 2 H) 8.00-8.16 (dd, 2 H, J = 10.26, J = 8.46 Hz) 8.22-8.39 (m, 2 H) 8.50-8.80 (m, 3 H) |
| 23 1-((5-methylbenzo[b]thiophen-2-yl)sulfonyl)-N-(pyrrolidin-3-yl)-1H-pyrrolo[3,2-c]quinolin-4-amine | The title compound was prepared starting from amine A-9c and 5-methylbenzo[b]-thiophene-2-sulfonyl chloride, and isolated as HCl salt. Yield 65%, C$_{24}$H$_{22}$N$_4$O$_2$S$_2$, MW 462.59, Monoisotopic Mass 462.12, [M + H]$^+$ 463.0 | |
| 24 7-fluoro-1-((3-chlorophenyl)sulfonyl)-N-(pyrrolidin-3-yl)-1H-pyrrolo[3,2-c]quinolin-4-amine | The title compound was prepared starting from amine A-9f and 3-chlorobenzene-sulfonyl chloride, and isolated as HCl salt. Yield 82%, C$_{21}$H$_{19}$Cl$_2$FN$_4$O$_2$S, MW 481.37, Monoisotopic Mass 480.06, [M + H]$^+$ 481.1 | |
| 25 8-chloro-1-((3-chlorophenyl)sulfonyl)-N-(pyrrolidin-3-yl)-1H-pyrrolo[3,2-c]quinolin-4-amine | The title compound was prepared starting from amine A-9g and 3-chlorobenzene-sulfonyl chloride, and isolated as HCl salt. Yield 80%, C$_{21}$H$_{18}$Cl$_2$N$_4$O$_2$S, MW 461.36, Monoisotopic Mass 460.05, [M + H]$^+$ 461.1 | $^1$H NMR (300 MHz, DMSO-d$_6$) δ (ppm) 2.22-2.28 (m, 1 H), 2.40-2.46 (m, 1 H), 3.25-3.38 (m, 1 H), 3.51-3.59 (m, 4 H), 5.25 (s, 1 H), 7.36-7.46 (m, 1 H), 7.59-7.65 (t, 2 H, J = 7.9 Hz), 7.81-7.84 (m, 2 H), 7.89- 8.07 (m, 1 H), 8.20-8.22 (m, 1 H), 8.30-8.35 (m, 1 H), 8.66-8.69 (m, 1 H), 9.50 (s, 1 H) |
| 26 N-methyl-1-(1-(phenylsulfonyl)-1H-pyrrolo[3,2-c]quinolin-4-yl)pyrrolidin-3-amine | The title compound was prepared starting from amine A-9h and benzenesulfonyl chloride, and isolated as HCl salt. Yield 68%, C$_{22}$H$_{22}$N$_4$O$_2$S, MW 406.50, Monoisotopic Mass 406.15, [M + H]$^+$ = 407.2 | $^1$H NMR (300 MHz, CD$_3$OD/CDCl$_3$) δ (ppm) 1.52-1.80 (m, 1 H), 2.74-3.02 (m, 5 H), 3.32 (s, 3 H), 6.34-6.37 (d, 1 H, J = 3.61 Hz), 7.28-7.30 (d, 1 H, J = 3.52 Hz), 7.30-7.35 (m, 2 H), 7.62 (m, 2 H), 7.69-7.73 (m, 2 H), 7.84-7.87 (m, 3 H), 8.47-8.56 (m, 1 H) |
| 27 1-(phenylsulfonyl)-4-(piperazin-1-yl)-1H-pyrrolo[3,2-c]quinoline | The title compound was prepared starting from amine A-9i and benzenesulfonyl chloride, and isolated as HCl salt. Yield 70%, C$_{21}$H$_{20}$N$_4$O$_2$S, MW 392.47, Monoisotopic Mass 392.13, [M + H]$^+$ = 393.5 | $^1$H NMR (300 MHz, methanol-d4) δ (ppm) 3.25-3.33 (d, 2 H, J = 1.28 Hz) 3.54 (b s, 4 H) 7.22-7.31 (m, 2 H) 7.41-7.57 (m, 4 H) 7.58-7.71 (d, 2 H, J = 7.44 Hz) 7.77-7.85 (d, 2 H, J = 7.69 Hz) 8.15 (b s, 1 H) 8.20-8.29 (m, 1 H) 8.85-8.93 (d, 1 H, J = 8.46 Hz) |
| 27' tert-butyl 4-(1-(phenylsulfonyl)-1H-pyrrolo[3,2-c]quinolin-4-yl)piperazine-1-carboxylate | The title compound was prepared starting from amine A-9i and benzenesulfonyl chloride. Yield 70%, C$_{26}$H$_{28}$N$_4$O$_4$S, MW 492.59, Monoisotopic Mass 492.18, [M + H]$^+$ = 493.30 | |
| 28 1-((2-bromophenyl)sulfonyl)-4-(piperazin-1-yl)-1H-pyrrolo[3,2-c]quinoline | The title compound was prepared starting from amine A-9i and 2-bromobenzene-sulfonyl chloride, and isolated as HCl salt. Yield 60%, C$_{21}$H$_{19}$BrN$_4$O$_2$S, MW 471.37, Monoisotopic Mass 470.04, [M + H]$^+$ 471.2 | $^1$H NMR (300 MHz, CD$_3$OD/CDCl$_3$) δ (ppm) 3.04-3.21 (b s, 4 H) 4.26 (b s, 3 H) 7.03-7.26 (m, 2 H) 7.29-7.62 (m, 4 H) 7.92-8.26 (m, 3 H) 8.29-8.43 (m, 1 H) |
| 29 1-((3-chlorophenyl)sulfonyl)-4-(piperazin-1-yl)-1H-pyrrolo[3,2-c]quinoline | The title compound was prepared starting from amine A-9i and 3-chlorobenzene-sulfonyl chloride, and isolated as HCl salt. Yield 95%, Mp 161-163° C., | $^1$H NMR (300 MHz, CD$_3$OD/CDCl$_3$) δ (ppm) 3.43 (b s, 4 H), 4.29 (b s, 4 H), 7.24 (s, 1 H), 7.26-7.50 (m, 3 H), 7.56-7.61 (m, 2 H), 7.68 (s, 1 |

-continued

| # | Name | Preparation / Yield / Formula | NMR |
|---|------|------------------------------|-----|
| | | $C_{21}H_{19}ClN_4O_2S$, MW 426.92, Monoisotopic Mass 426.09, [M + H]$^+$ 427.2 | H), 8.02 (s, 1 H), 8.22-8.32 (d, 1 H, J = 8.47 Hz), 8.74-8.76 (d, 1 H, J = 8.31 Hz) |
| 29' | tert-butyl 4-(1-((3-chlorophenyl)sulfonyl)-1H-pyrrolo[3,2-c]quinolin-4-yl)piperazine-1-carboxylate | The title compound was prepared starting from amine A-9i and 3-chlorobenzenesulfonyl chloride. Yield 95%, $C_{26}H_{27}ClN_4O_4S$, MW 527.03, Monoisotopic Mass 526.14, [M + H]$^+$ 427.46 | |
| 30 | 1-((3-fluorophenyl)sulfonyl)-4-(piperazin-1-yl)-1H-pyrrolo[3,2-c]quinoline | The title compound was prepared starting from amine A-9i and 3-fluorobenzenesulfonyl chloride, and isolated as HCl salt. Yield 93%, Mp 192-193° C., $C_{21}H_{19}FN_4O_2S$, MW 410.46, Monoisotopic Mass 410.12, [M + H]$^+$ 411.3 | $^1$H NMR (300 MHz, CD$_3$OD/CDCl$_3$) δ (ppm) 3.45 (b s, 4 H) 4.28 (b s, 4 H) 7.13-7.23 (d, 2 H, J = 6.92 Hz) 7.34-7.61 (m, 5 H) 8.01 (b s, 1 H) 8.24-8.34 (d, 1 H, J = 7.44 Hz) 8.69-8.78 (d, 1 H, J = 8.46 Hz) |
| 31 | 1-((4-fluorophenyl)sulfonyl)-4-(piperazin-1-yl)-1H-pyrrolo[3,2-c]quinoline | The title compound was prepared starting from amine A-9i and 4-fluorobenzenesulfonyl chloride, and isolated as HCl salt. Yield 95%, $C_{21}H_{19}FN_4O_2S$, MW 410.46, Monoisotopic Mass 410.12, [M + H]$^+$ 411.3 | |
| 32 | 1-((2,5-difluorophenyl)sulfonyl)-4-(piperazin-1-yl)-1H-pyrrolo[3,2-c]quinoline | The title compound was prepared starting from amine A-9i and 2,5-difluorobenzene-sulfonyl chloride, and isolated as HCl salt. Yield 81%, $C_{21}H_{18}F_2N_4O_2S$, MW 428.46, Monoisotopic Mass 428.11, [M + H]$^+$ 429.2 | |
| 33 | 1-((3,4-difluorophenyl)sulfonyl)-4-(piperazin-1-yl)-1H-pyrrolo[3,2-c]quinoline | The title compound was prepared starting from amine A-9i and 3,4-difluorobenzenesulfonyl chloride, and isolated as HCl salt. Yield 83%, $C_{21}H_{18}F_2N_4O_2S$, MW 428.46, Monoisotopic Mass 428.11, [M + H]$^+$ 429.4 | |
| 34 | 1-((3,4-dichlorophenyl)sulfonyl)-4-(piperazin-1-yl)-1H-pyrrolo[3,2-c]quinoline | The title compound was prepared starting from amine A-9i and 3,4-dichlorobenzene-sulfonyl chloride, and isolated as HCl salt. Yield 80%, $C_{21}H_{18}Cl_2N_4O_2S$, MW 461.36, Monoisotopic Mass 460.05, [M + H]$^+$ 461.2 | |
| 35 | 1-((3-(trifluoromethyl)phenyl)sulfonyl)-4-(piperazin-1-yl)-1H-pyrrolo[3,2-c]quinoline | The title compound was prepared starting from amine A-9i and 3-(trifluoromethyl)-benzenesulfonyl chloride, and isolated as HCl salt. Yield 92%, $C_{22}H_{19}F_3N_4O_2S$, MW 460.47, Monoisotopic Mass 460.12, [M + H]$^+$ 461.3 | $^1$H NMR (300 MHz, CD$_3$OD/CDCl$_3$) δ (ppm) 3.40 (b s, 4 H) 4.25 (b s, 4 H) 7.22-7.26 (m, 1 H) 7.33-7.44 (t, 1 H, J = 7.79 Hz), 7.52-7.62 (t, 1H, J = 7.83 Hz), 7.61-7.70 (d, 2H, J = 8.22 Hz), 7.80-7.89 (d, 2H, J = 8.18 Hz), 8.03-8.08 (d, 1H, J = 3.32 Hz), 8.27-8.34 (d, 1H, J = 8.43 Hz), 8.72-8.77 (d, 1 H, J = 8.68 Hz) |
| 36 | 1-((4-(trifluoromethyl)phenyl)sulfonyl)-4-(piperazin-1-yl)-1H-pyrrolo[3,2-c]quinoline | The title compound was prepared starting from amine A-9i and 4-(trifluoromethyl)-benzene-sulfonyl chloride, and isolated as HCl salt. Yield 89%, $C_{22}H_{19}F_3N_4O_2S$, MW 460.47, Monoisotopic Mass 460.12, [M + H]$^+$ 461.3 | |
| 37 | 1-((3-methoxyphenyl)sulfonyl)-4-(piperazin-1-yl)-1H-pyrrolo[3,2-c]quinoline | The title compound was prepared starting from amine A-9i and 3-methoxybenzene-sulfonyl chloride, and isolated as HCl salt. Yield 91%, $C_{22}H_{22}N_4O_3S$, MW 422.50, Monoisotopic Mass 422.14, [M + H]$^+$ 423.3 | |
| 38 | 1-((3-cyanophenyl)sulfonyl)-4-(piperazin-1-yl)-1H-pyrrolo[3,2-c]quinoline | The title compound was prepared starting from amine A-9i and 3-cyanobenzene-sulfonyl chloride, and isolated as HCl salt. Yield 89%, $C_{22}H_{19}N_5O_2S$, MW 417.48, Monoisotopic Mass 417.13. [M + H]$^+$ | $^1$H NMR (300 MHz, CD$_3$OD/CDCl$_3$) δ (ppm) 3.42 (b s, 4 H) 4.24 (b s, 4 H) 7.21 (b s, 1 H) 7.36-7.41 (m, 1 H) 7.51-7.58 (m, 2 H) 7.73-7.83 (d, 1 H, J = 6.67 Hz) 7.88 (b |

| | | |
|---|---|---|
| | 418.2 | s, 1 H) 8.02 (s, 2 H) 8.18-8.27 (d, 1 H, J = 8.21 Hz) 8.63-8.72 (d, 1 H, J = 8.46 Hz) |
| 39 1-((3-methylphenyl)sulfonyl)-4-(piperazin-1-yl)-1H-pyrrolo[3,2-c]quinoline | The title compound was prepared starting from amine A-9i and 3-methylbenzene sulfonyl chloride, and isolated as HCl salt. Yield 80%, C$_{22}$H$_{23}$ClN$_4$O$_2$S, MW 406.50, Monoisotopic Mass 406.15, [M + H]$^+$ 407.1 | |
| 40 1-((4-isopropylphenyl)sulfonyl)-4-(piperazin-1-yl)-1H-pyrrolo[3,2-c]quinoline | The title compound was prepared starting from amine A-9i and 4-isopropylbenzene-sulfonyl chloride, and isolated as HCl salt. Yield 79%, C$_{24}$H$_{26}$N$_4$O$_2$S, MW 434.55, Monoisotopic Mass 434.18, [M + H]$^+$ 435.3 | $^1$H NMR (300 MHz, CD$_3$OD/CDCl$_3$) δ (ppm) 1.99 (s, 6 H) 2.85 (m, 1 H) 3.50 (b s, 4 H) 4.34 (b s, 4 H) 7.15-7.28 (m, 3 H) 7.37-7.46 (t, 1 H, J = 7.57 Hz) 7.53-7.69 (m, 3 H) 8.02 (b s, 1 H) 8.31-8.40 (d, 1 H, J = 8.21 Hz) 8.81-8.88 (d, 1 H, J = 8.46 Hz) |
| 41 1-((4-(tert-butyl) phenyl)sulfonyl)-4-(piperazin-1-yl)-1H-pyrrolo[3,2-c]quinoline | The title compound was prepared starting from amine A-9i and 4-tert-butylbenzene-sulfonyl chloride, and isolated as HCl salt. Yield 70%, C$_{25}$H$_{28}$N$_4$O$_2$S, MW 448.58, Monoisotopic Mass 448.19, [M + H]$^+$ 449.3 | |
| 42 1-(4-(aminophenyl)sulfonyl)-4-(piperazin-1-yl)-1H-pyrrolo[3,2-c]quinoline | The title compound was prepared starting from amine A-9i and 4-aminobenzene-sulfonyl chloride, and isolated as HCl salt. Yield 68%, C$_{21}$H$_{21}$N$_5$O$_2$S, MW 407.49, Monoisotopic Mass 407.14, [M + H]$^+$ 408.2 | |
| 43 1-(naphthalen-1-ylsulfonyl)-4-(piperazin-1-yl)-1H-pyrrolo[3,2-c]quinoline | The title compound was prepared starting from amine A-9i and 1-naphtalenesulfonyl chloride, and isolated as HCl salt. Yield 86%, Mp 158-160° C., C$_{25}$H$_{22}$N$_4$O$_2$S, MW 442.53, Monoisotopic Mass 442.15, [M + H]$^+$ 443.3 | $^1$H NMR (300 MHz, CD$_3$OD/CDCl$_3$) δ (ppm) 3.36-3.55 (m, 4 H), 4.20-4.40 (m, 4 H), 7.16-7.29 (m, 2 H), 7.35-7.45 (d, 1 H, J = 6.16 Hz), 7.46-7.62 (m, 3 H), 7.80-7.89 (d, 1 H, J = 7.69 Hz), 7.95-8.10 (m, 3 H), 8.17-8.30 (t, 2 H, J = 8.08 Hz), 8.54-8.64 (d, 1 H, J = 8.72 Hz) |
| 43' tert-butyl 4-(1-(naphthalen-1-ylsulfonyl)-1H-pyrrolo[3,2-c]quinolin-4-yl)piperazine-1-carboxylate | The title compound was prepared starting from amine A-9i and 1-naphtalenesulfonyl chloride. Yield 86%, C$_{30}$H$_{30}$N$_4$O$_4$S, MW 542.65, Monoisotopic Mass 542.20, [M + H]$^+$ 543.34 | |
| 44 1-(naphthalen-2-ylsulfonyl)-4-(piperazin-1-yl)-1H-pyrrolo[3,2-c]quinoline | The title compound was prepared starting from amine A-9i and 2-naphtalenesulfonyl chloride, and isolated as HCl salt. Yield 88%, C$_{25}$H$_{23}$ClN$_4$O$_2$S, MW 442.53, Monoisotopic Mass: 442.15, [M + H]$^+$ 443.1 | |
| 45 1-(quinolin-8-ylsulfonyl)-4-(piperazin-1-yl)-1H-pyrrolo[3,2-c]quinoline | The title compound was prepared starting from amine A-9i and 8-quinolinesulfonyl chloride, and isolated as HCl salt. Yield 85%, C$_{24}$H$_{21}$N$_5$O$_2$S, MW 443.53, Monoisotopic Mass 443.14, [M + H]$^+$ 444.2 | $^1$H NMR (300 MHz, CD$_3$OD/CDCl$_3$) δ (ppm) 3.45 (b s, 4 H), 4.30 (b s, 4 H), 7.07 (b s, 1 H), 7.31-7.41 (m, 2 H), 7.47-7.52 (t, 1 H, J = 7.44 Hz), 7.63-7.68 (t, 1 H, J = 7.95 Hz), 8.07-8.13 (t, 2 H, J = 7.18 Hz), 8.25-8.28 (d, 1 H, J = 8.46 Hz), 8.42 (b s, 1 H), 8.68-8.70 (m, 2 H), 8.78-8.81 (d, 1 H, J = 8.46 Hz) |
| 46 1-((5-chlorothiophen-2-yl)sulfonyl)-4-(piperazin-1-yl)-1H-pyrrolo[3,2-c]quinoline | The title compound was prepared starting from amine A-9i and 5-chlorothiophene-2-sulfonyl chloride, and isolated as HCl salt. Yield 65%, C$_{19}$H$_{17}$ClN$_4$O$_2$S$_2$, MW 432.95, Monoisotopic Mass 432.05, [M + H]$^+$ 433.2 | $^1$H NMR (300 MHz, CD$_3$OD/CDCl$_3$) δ (ppm) 3.34 (b s, 4 H), 3.97 (b s, 4 H), 7.51-7.56 (t, 1 H, J = 7.69 Hz), 7.64-7.69 (t, 1 H, J = 7.43 Hz), 7.90-8.14 (m, 3 H), 8.84-8.86 (d, 1 H, J = 7.69 Hz), 9.62 (s, 2 H) |
| 46' tert-butyl 4-(1-((5-chlorothiophen-2-yl)sulfonyl)-1H- | The title compound was prepared starting from amine A-9i and 5-chlorothiophene-2-sulfonyl | |

-continued

| # | Compound | Preparation | NMR/Data |
|---|---|---|---|
| | pyrrolo[3,2-c]quinolin-4-yl)piperazine-1-carboxylate | chloride.<br>Yield 65%, $C_{24}H_{25}ClN_4O_4S_2$, MW 533.06, Monoisotopic Mass 532.10, $[M + H]^+$ 533.2. | |
| 47 | 1-((5-methylbenzo[b]thiophen-2-yl)sulfonyl)-4-(piperazin-1-yl)-1H-pyrrolo[3,2-c]quinoline | The title compound was prepared starting from amine A-9i and 5-methylbenzo[b]-thiophene-2-sulfonyl chloride, and isolated as HCl salt.<br>Yield 68%, $C_{24}H_{22}N_4O_2S_2$, MW 462.59, Monoisotopic Mass 462.12, $[M + H]^+$ 463.9 | |
| 48 | 1-((5-chloro-3-methylbenzo[b]thiophen-2-yl)sulfonyl)-4-(piperazin-1-yl)-1H-pyrrolo[3,2-c]quinoline | The title compound was prepared starting from amine A-9i and 5-chloro-3-methylbenzo[b]thiophene-2-sulfonyl chloride, and isolated as HCl salt.<br>Yield 63%, $C_{24}H_{21}ClN_4O_2S_2$, MW 497.03, Monoisotopic Mass 497.08, $[M + H]^+$ 497.2 | $^1$H NMR (300 MHz, CD$_3$OD/CDCl$_3$) δ (ppm) 2.58 (s, 3 H), 3.51 (b s, 4 H), 4.32 (b s, 4 H), 7.24-7.26 (m, 3 H), 7.39-7.58 (m, 2 H), 7.61-7.71 (m, 1 H), 8.01 (s, 1 H), 8.33 (s, 1 H), 8.81-8.83 (m, 1 H) |
| 48' | tert-butyl 4-(1-((5-chloro-3-methylbenzo[b]thiophen-2-yl)sulfonyl)-1H-pyrrolo[3,2-c]quinolin-4-yl)piperazine-1-carboxylate | The title compound was prepared starting from amine A-9i and 5-chloro-3-methylbenzo[b]-thiophene-2-sulfonyl chloride.<br>Yield 63% $C_{29}H_{29}ClN_4O_4S_2$, MW 597.15, Monoisotopic Mass 596.13, $[M + H]^+$ 597.19, 599.42, 600.38 | |
| 49 | 1-(3-chlorobenzyl)-4-(piperazin-1-yl)-1H-pyrrolo[3,2-c]quinoline | The title compound was prepared starting from amine A-9i and 1-chloro-3-(chloromethyl)-benzene and isolated as HCl salt.<br>Yield 90%, $C_{21}H_{20}Cl_2N_4O_2S$, MW 376.88, Monoisotopic Mass 376.15, $[M + H]^+$ 377.2 | |
| 50 | 1-(3-fluorobenzyl)-4-(piperazin-1-yl)-1H-pyrrolo[3,2-c]quinoline | The title compound was prepared starting from amine A-9i and 1-(chloromethyl)-3-fluoro-benzene and isolated as HCl salt.<br>Yield 91%, $C_{22}H_{21}FN_4$, MW 360.43, Monoisotopic Mass 360.18, $[M + H]^+$ 361.2 | |
| 51 | (3-chlorophenyl)-(4-(piperazin-1-yl)-1H-pyrrolo[3,2-c]quinolin-1-yl)methanone | The title compound was prepared starting from amine A-9i and 3-chlorobenzoyl chloride, and isolated as HCl salt.<br>Yield 87%, $C_{22}H_{20}Cl_2N_4O$, MW 427.33, Monoisotopic Mass 426.10, $[M + H]^+$ 427.1 | |
| 52 | (3-methylphenyl)-(4-(piperazin-1-yl)-1H-pyrrolo[3,2-c]quinolin-1-yl)methanone | The title compound was prepared starting from amine A-9i and 3-fluorobenzoyl chloride, and isolated as HCl salt.<br>Yield 86%, $C_{23}H_{22}N_4O$, MW 370.45, Monoisotopic Mass 370.18, $[M + H]^+$ 371.2 | |
| 53 | 1-(phenylsulfonyl)-4-(4-methylpiperazin-1-yl)-1H-pyrrolo[3,2-c]quinoline | The title compound was prepared starting from amine A-9j and benzenesulfonyl chloride.<br>Yield 85%, $C_{22}H_{22}N_4O_2S$, MW 406.50, Monoisotopic 406.15, $[M + H]^+$ 407.2 | $^1$H NMR (300 MHz, CDCl$_3$) δ (ppm) 2.38 (s, 3 H) 2.54-2.72 (m, 4 H) 3.56-3.77 (m, 4 H) 6.83 (s, 1 H) 7.21-7.28 (m, 1 H) 7.32-7.40 (m, 2 H) 7.40-7.52 (m, 2 H) 7.60-7.74 (m, 2 H) 7.77-7.85 (m, 1 H) 7.87-7.95 (m, 1 H) 8.76-8.79 (dd, 1 H, J = 8.59, J = 0.90 Hz) |
| 54 | 1-((3-chlorophenyl)sulfonyl)-4-(4-methylpiperazin-1-yl)-1H-pyrrolo[3,2-c]quinoline | The title compound was prepared starting from amine A-9j and 3-chlorobenzene-sulfonyl chloride.<br>Yield 91%, $C_{22}H_{21}ClN_4O_2S$, MW 440.95, Monoisotopic Mass 440.11, $[M + H]^+$ 441.2 | $^1$H NMR (300 MHz, CDCl$_3$) δ (ppm) 2.39 (s, 3 H) 2.60-2.68 (m, 4 H) 3.65-3.72 (m, 4 H) 6.86-6.87 (d, 1 H, J = 3.59 Hz) 7.27-7.34 (m, 2 H) 7.42-7.58 (m, 3 H) 7.71-7.72 (t, 1 H, J = 1.92 Hz) 7.81-7.89 (m, 2 H) 8.74-8.77 (dd, 1 H, J = 8.59, J = 0.90 Hz) |
| 55 | 1-((3-fluorophenyl)sulfonyl)-4-(4-methylpiperazin-1-yl)-1H-pyrrolo[3,2-c]quinoline | The title compound was prepared starting from amine A-9j and 3-fluorobenzene-sulfonyl chloride.<br>Yield 88%, $C_{22}H_{21}FN_4O_2S$, MW 424.49, Monoisotopic Mass 424.14, $[M + H]^+$ 425.3 | $^1$H NMR (300 MHz, CDCl$_3$) δ (ppm) 2.39 (s, 3 H) 2.55-2.72 (m, 4 H) 3.60-3.76 (m, 4 H) 6.86-6.87 (d, 1 H, J = 3.85 Hz) 7.19-7.22 (m, 1 H) 7.26-7.42 (m, 3 H) 7.43-7.55 (m, 2 H) 7.77-7.92 (m, 2 H) |

| 56 | 1-((4-fluorophenyl)sulfonyl)-4-(4-methylpiperazin-1-yl)-1H-pyrrolo[3,2-c]quinoline | The title compound was prepared starting from amine A-9j and 4-fluorobenzene-sulfonyl chloride. Yield 81%, $C_{22}H_{21}FN_4O_2S$, MW 424.49, Monoisotopic Mass 424.14, $[M + H]^+$ 425.1 | 8.74-8.77 (dd, 1 H, J = 8.59, J = 0.90 Hz) |
|---|---|---|---|
| 57 | 1-((4-aminophenyl)sulfonyl)-((4-(4-methylpiperazin-1-yl)-1H-pyrrolo[3,2-c]quinoline | The title compound was prepared starting from amine A-9j and 4-aminobenzene-sulfonyl chloride. Yield 65%, $C_{21}H_{22}ClN_5O_2S$, MW 421.52 Monoisotopic Mass 421.16, $[M + H]^+$ 422.2 | $^1$H NMR (300 MHz, CDCl$_3$) δ (ppm) 2.38 (s, 3 H) 2.55-2.74 (m, 4 H) 3.55-3.76 (m, 4 H) 6.50 (s, 1 H) 6.60-6.74 (m, 1 H) 6.86 (s, 1 H) 7.21-7.29 (m, 1 H) 7.36-7.42 (m, 2 H) 7.44-7.55 (m, 2 H) 7.68-7.76 (m, 1 H) 7.88-7.95 (m, 1 H) 8.77-8.81 (dd, 1 H, J = 8.6, J = 0.9 Hz) |
| 58 | 1-(naphthalen-1-ylsulfonyl)-4-(4-methylpiperazin-1-yl)-1H-pyrrolo[3,2-c]quinoline | The title compound was prepared starting from amine A-9j and 1-naphtalenesulfonyl chloride. Yield 89%, $C_{26}H_{24}N_4O_2S$, MW 456.56, Monoisotopic Mass 456.16, $[M + H]^+$ 457.2. | $^1$H NMR (300 MHz, CDCl$_3$) δ (ppm) 2.43 (s, 3 H), 2.65-2.73 (t, 4 H, J = 4.88 Hz), 3.74-3.77 (t, 4 H, J = 4.87 Hz), 6.87-6.89 (d, 1 H, J = 3.85 Hz), 7.05-7.27 (m, 1 H), 7.30-7.42 (m, 2 H), 7.60-7.74 (m, 3 H), 7.79-7.82 (dd, 1 H, J = 1.03 Hz, J = 8.34 Hz), 7.86-7.92 (m, 1 H), 7.98-8.03 (m, 2 H), 8.46-8.50 (dd, 1 H, J = 8.46 Hz, J = 0.77 Hz,), 8.57-8.60 (d, 1 H, J = 8.72 Hz) |
| 59 | 1-(quinolin-8-ylsulfonyl)-4-(4-methylpiperazin-1-yl)-1H-pyrrolo[3,2-c]quinolone | The title compound was prepared starting from amine A-9j and 8-quinolnesulfonyl chloride. Yield 72%, $C_{22}H_{22}N_4O_2S$, MW 457.55, Monoisotopic Mass 457.16, $[M + H]^+$ 458.4 | |
| 60 | 1-(phenylsulfonyl)-4-(4-benzylpiperazin-1-yl)-1H-pyrrolo[3,2-c]quinoline | The title compound was prepared starting from amine A-9k and benzenesulfonyl chloride. Yield 93%, $C_{28}H_{26}N_4O_2S$, MW 482.60, Monoisotopic Mass 482.18, $[M + H]^+$ 483.4 | |
| 61 | 1-((5-chlorothiophen-2-yl)sulfonyl)-4-(4-benzylpiperazin-1-yl)-1H-pyrrolo[3,2-c]quinoline | The title compound was prepared starting from amine A-9k and 5-chlorothiophene-2-sulfonyl chloride. Yield 81%, $C_{26}H_{23}ClN_4O_2S_2$, MW 523.07, Monoisotopic Mass 522.10, $[M + H]^+$ 523.4 | |
| 62 | 1-(quinolin-8-ylsulfonyl)-4-(4-benzylpiperazin-1-yl)-1H-pyrrolo[3,2-c]quinoline | The title compound was prepared starting from amine A-9k and 8-quinolinesulfonyl chloride. Yield 88%, $C_{31}H_{27}N_5O_2S$, MW 533.64, Monoisotopic Mass 533.19, $[M + H]^+$ 534.5 | $^1$H NMR (300 MHz, CDCl$_3$) δ (ppm) 2.70-2.79 (m, 4 H) 3.63-3.80 (m, 6 H) 6.77-6.78 (d, 1 H, J = 3.85 Hz) 7.12-7.18 (m, 1 H) 7.28-7.47 (m, 6 H) 7.55-7.62 (m, 1 H) 7.75-7.79 (dd, 1 H, J = 8.46, J = 1.03 Hz) 8.01-8.04 (dd, 1 H, J = 8.33, J = 1.41 Hz) 8.11-8.16 (m, 1 H) 8.11-8.16 (m, 1 H) 8.25-8.26 (d, 1 H, J = 3.85 Hz) 8.47-8.50 (dd, 1 H, J = 7.44, J = 1.28 Hz) 8.66-8.69 (dd, 1 H, J = 8.59, J = 0.90 Hz) 8.87-8.88 (dd, 1 H, J = 4.10, J = 1.80 Hz) |
| 63 | 8-nitro-1-((4-isopropylphenyl)sulfonyl)-4-(piperazin-1-yl)-1H-pyrrolo[3,2-c]quinoline | The title compound was prepared starting from amine A-9l and 4-isopropylbenzene-sulfonyl chloride, and isolated as HCl salt. Yield 70%, $C_{24}H_{25}N_5O_4S$, MW 479.55, Monoisotopic Mass 479.16, $[M + H]^+$ 480.2 | $^1$H NMR (300 MHz, CD$_3$OD/CDCl$_3$) δ (ppm) 1.25 (s, 6 H), 2.90-2.92 (m, 1 H), 3.44 (b s, 4 H), 4.31 (b s, 4 H), 7.25 (s, 1 H), 7.28-7.53 (m, 2 H), 7.58-7.65 (m, 2 H), 7.70 (s, 1 H), 8.23-8.35 (d, 1 H, J = 8.5 Hz), 8.74-8.76 (d, 1 H, J = 8.3 Hz), 9.06 (s, 1 H) |
| 64 | 8-nitro-1-((3-(trifluoromethyl)phenyl)sulfonyl)-4-(piperazin-1-yl)-1H-pyrrolo[3,2-c] | The title compound was prepared starting from amine A-9l and 3-(trifluoromethyl)-benzenesulfonyl chloride, and isolated | |

-continued

| # | Compound | Preparation | NMR |
|---|---|---|---|
| | c]quinoline | as HCl salt. Yield 84%, $C_{22}H_{18}F_3N_5O_4S$, MW 505.47, Monoisotopic Mass: 505.10, $[M + H]^+$ 506.1 | |
| 65 | 8-amino-1-((3,4-dichlorophenyl)sulfonyl)-4-(piperazin-1-yl)-1H-pyrrolo[3,2-c]quinoline | The title compound was prepared starting from amine A-9m and 3,4-dichloro-benzenesulfonyl chloride, and isolated as HCl salt. Yield 63%, $C_{21}H_{19}Cl_2N_5O_2S$, MW 476.38, Monoisotopic Mass 475.06, $[M + H]^+$ 476.1 | |
| 66 | 8-carbonitrile-1-(3-methylphenyl)-4-(piperazin-1-yl)-1H-pyrrolo[3,2-c]quinoline | The title compound was prepared starting from amine A-9n and 3-methylbenzene-sulfonyl chloride, and isolated as HCl salt. Yield 72%, $C_{23}H_{21}N_5O_2S$, MW 431.14, Monoisotopic Mass 431.51, $[M + H]^+$ 432.2 | |
| 67 | 8-carbonitrile-1-(naphthalen-1-ylsulfonyl)-4-(piperazin-1-yl)-1H-pyrrolo[3,2-c]quinoline | The title compound was prepared starting from amine A-9n and 1-naphtalenesulfonyl chloride, and isolated as HCl salt. Yield 88%, $C_{26}H_{22}ClN_5O_2S$, MW 504.00, Monoisotopic Mass 503.12, $[M + H]^+$ 504.1 | |
| 68 | 8-methoxy-1-((3-(trifluoromethyl)phenyl)sulfonyl)-4-(piperazin-1-yl)-1H-pyrrolo[3,2-c]quinoline | The title compound was prepared starting from amine A-9o and 3-(trifluoromethyl)-benzenesulfonyl chloride, and isolated as HCl salt. Yield 86%, $C_{23}H_{21}F_3N_4O_3S$, MW 490.50, Monoisotopic Mass 490.13, $[M + H]^+$ 491.1 | |
| 69 | 8-methoxy-1-((3-fluorophenyl)sulfonyl)-4-(piperazin-1-yl)-1H-pyrrolo[3,2-c]quinoline | The title compound was prepared starting from amine A-9o and 3-fluorobenzene-sulfonyl chloride, and isolated as HCl salt. Yield 91%, $C_{22}H_{21}FN_4O_3S$, MW 440.49, Monoisotopic Mass 440.13, $[M + H]^+$ 441.1 | $^1$H NMR (300 MHz, CD$_3$OD/CDCl$_3$) δ (ppm) 3.46 (b s, 4 H) 3.85 (s, 3 H) 4.33 (b s, 4 H) 7.28 (s, 1 H) 7.29-7.55 (m, 3 H) 7.56-7.69 (m, 2 H) 7.77 (s, 1 H) 8.26-8.33 (d, 1 H, J = 8.47 Hz) 8.77-8.79 (d, 1 H, J = 8.3 Hz) |
| 70 | 8-chloro-1-((3-chlorophenyl)sulfonyl)-4-(piperazin-1-yl)-1H-pyrrolo[3,2-c]quinoline | The title compound was prepared starting from amine A-9p and 3-chlorobenzene-sulfonyl chloride, and isolated as HCl salt. Yield 93%, $C_{21}H_{18}Cl_2N_4O_2S$, MW 461.36, Monoisotopic Mass: 460.05, $[M + H]^+$ 461.1 | $^1$H NMR (300 MHz, CD$_3$OD/CDCl$_3$) δ (ppm) 2.27-2.41 (m, 1 H) 2.55-2.67 (m, 1 H) 3.24-3.35 (m, 1 H) 3.40-3.45 (m, 1 H) 3.58-3.77 (m, 3 H) 5.50-5.65 (m, 1 H) 7.30-7.65 (m, 5 H) 7.70-7.72 (t, 1 H, J = 1.80 Hz) 7.85-8.00 (m, 1 H) 8.41-8.49 (d, 1 H, J = 8.46 Hz) 8.72-8.78 (dd, 1 H, J = 8.59, J = 1.15 Hz) |
| 71 | 8-chloro-1-(naphthalen-1-ylsulfonyl)-4-(piperazin-1-yl)-1H-pyrrolo[3,2-c]quinoline | The title compound was prepared starting from amine A-9p and 1-naphtalenesulfonyl chloride, and isolated as HCl salt. Yield 88%, $C_{25}H_{21}ClN_4O_2S$, MW 476.98, Monoisotopic Mass: 476.11, $[M + H]^+$ 477.1 | |
| 72 | 7-fluoro-1-((3-methylphenyl)sulfonyl)-4-(piperazin-1-yl)-1H-pyrrolo[3,2-c]quinoline | The title compound was prepared starting from amine A-9q and 3-methylbenzene-sulfonyl chloride, and isolated as HCl salt. Yield 77%, $C_{22}H_{21}FN_4O_2S$, MW 424.49, Monoisotopic Mass: 424.14, $[M + H]^+$ 425.1 | |
| 73 | 7-fluoro-1-((3-chlorophenyl)sulfonyl)-4-(piperazin-1-yl)-1H-pyrrolo[3,2-c]quinoline | The title compound was prepared starting from amine A-9q and 3-chlorobenzene-sulfonyl chloride, and isolated as HCl salt. Yield 82%, $C_{21}H_{18}ClFN_4O_2S$, MW 444.91, Monoisotopic Mass: 444.08, $[M + H]^+$ 453.2 | |
| 74 | 1-((3,4-difluorophenyl)sulfonyl)-4-(1,4-diazepan-1-yl)-1H-pyrrolo[3,2-c]quinoline | The title compound was prepared starting from amine A-9r and 2,5-difluorobenzene-sulfonyl chloride, and isolated as HCl salt. Yield 89%, $C_{22}H_{20}F_2N_4O_2S$, MW 442.48, Monoisotopic Mass: 442.13, $[M + H]^+$ | $^1$H NMR (300 MHz, DMSO-d$_6$) δ (ppm)1.62-1.66 (m, 2 H), 2.52-2.59 (t, 2 H, J = 7.2 Hz), 2.73-2.79 (t, 2 H, J = 7.2 Hz), 3.64-3.72 (t, 2 H, J = 7.1 Hz), 3.12-1.22 (t, 2 H, J = 7.2 Hz), |

| | | | 443.1 | 6.30-6.36 (s, 1 H), 7.24-7.30 (s, 1 H), 7.25-7.29 (m, 1 H), 7.34-7.39 (m, 1 H), 7.62-7.68 (m, 1 H), 7.70-7.74 (m, 1 H), 7.75-79 (m, 1 H), 7.82-7.89 (m, 1 H), 8.07-8.12 (m, 1 H), 8.22-8.28 (m, 1 H) |
|---|---|---|---|---|
| 75 | 1-((3-chlorophenyl)sulfonyl)-4-(1,4-diazepan-1-yl)-1H-pyrrolo[3,2-c]quinoline | | The title compound was prepared starting from amine A-9r and 3-chlorobenzenesulfonyl chloride, and isolated as HCl salt. Yield 91%, $C_{22}H_{21}ClN_4O_2S$, MW 440.95, Monoisotopic Mass: 440.11, $[M + H]^+$ 441.1 | |
| 76 | 1-((3-chlorophenyl)sulfonyl)-4-(piperidin-1-yl)-1H-pyrrolo[3,2-c]quinoline | | The title compound was prepared starting from amine A-9s and 3-chlorobenzene-sulfonyl chloride. Yield 94%, $C_{22}H_{20}ClN_3O_2S$, MW 425.93, Monoisotopic Mass: 425.10, $[M + H]^+$ 426.0 | |
| 77 | 1-(quinolin-8-ylsulfonyl)-4-(piperidin-1-yl)-1H-pyrrolo[3,2-c]quinoline | | The title compound was prepared starting from amine A-9s and 8-quinolinesulfonyl chloride. Yield 95%, $C_{25}H_{22}N_4O_2S$, MW 442.53, Monoisotopic Mass: 442.15, $[M + H]^+$ 443.1 | $^1$H NMR (300 MHz, DMSO-$d_6$) δ (ppm) 1.75 (b s, 3 H) 3.84-4.05 (m, 6 H) 7.19-7.40 (m, 2 H) 7.52-7.69 (m, 1 H) 7.80-7.88 (t, 1 H, J = 7.92 Hz) 7.93-8.03 (t, 1 H, J = 7.53 Hz) 8.10-8.23 (dd, 1 H, J = 7.92, J = 5.58 Hz) 8.36-8.64 (m, 4 H) 8.79-8.89 (m, 1 H) 9.27-9.42 (m, 2 H) |
| 78 | 1-((3-chlorophenyl)sulfonyl)-4-(morpholine-4-yl)-1H-pyrrolo[3,2-c]quinoline | | The title compound was prepared starting from amine A-9t and 3-chlorobenzene-sulfonyl chloride. Yield 96%, $C_{21}H_{18}ClN_3O_3S$, MW: 427.90, Monoisotopic Mass 427.08, $[M + H]^+$ 428.0 | $^1$H NMR (300 MHz, DMSO-$d_6$) δ (ppm) 3.48-3.57 (m, 4 H) 3.73-3.81 (m, 4 H) 7.17-7.20 (d, 1 H, J = 3.72 Hz) 7.28-7.34 (m, 1 H) 7.45-7.51 (m, 1 H) 7.53-7.58 (m, 1 H) 7.67-7.76 (m, 3 H) 7.94-7.97 (t, 1 H, J = 1.86 Hz) 8.05-8.08 (d, 1 H, J = 3.91 Hz) 8.60-8.64 (dd, 1 H, J = 8.51, J = 0.88 Hz) |
| 79 | 1-(quinolin-8-ylsulfonyl)-4-(morpholine-4-yl)-1H-pyrrolo[3,2-c]quinoline | | The title compound was prepared starting from amine A-9t and 8-quinolinesulfonyl chloride. Yield 89%, $C_{24}H_{20}N_4O_3S$, MW 444.51, Monoisotopic Mass: 444.13, $[M + H]^+$ 445.2 | |
| 80 | 1-((3-methylphenyl)sulfonyl)-4-(pyrrolidin-3-yloxy)-1H-pyrrolo[3,2-c]quinoline | | The title compound was prepared starting from alcohol A-9x and 3-methylbenzene-sulfonyl chloride. Yield 79%, $C_{22}H_{21}N_3O_3S$, MW 407.49, Monoisotopic Mass: 407.13, $[M + H]^+$ 408.1 | $^1$H NMR (300 MHz, DMSO-$d_6$) δ (ppm) 1.75-2.20 (m, 3 H) 2.37 (s, 3 H) 2.66-2.80 (m, 3 H) 2.99-3.20 (m, 2 H) 3.60-3.77 (m, 1 H) 6.30-6.35 (d, 1 H, J = 6.1 Hz) 7.25-7.30 (d, 1 H, J = 6.1 Hz) 7.45-7.50 (m, 1 H) 7.65-7.80 (m, 3 H) 7.88-7.92 (m, 1 H) 8.17-8.25 (m, 2 H) |
| 81 | 1-((2,5-difluorophenyl)sulfonyl)-4-(pyrrolidin-3-yloxy)-1H-pyrrolo[3,2-c]quinoline | | The title compound was prepared starting from alcohol A-9x and 2,5-difluorobenzene-sulfonyl chloride, and isolated as HCl salt. Yield 82%, $C_{21}H_{17}F_2N_3O_3S$, MW 429.44, Monoisotopic Mass: 429.10, $[M + H]^+$ 430.1 | |

Example 2a—In Vitro Evaluation

Radioligand binding assays were employed for determining the affinity and the selectivity profile of the synthesized compounds for cloned serotonin: $5-HT_{1A}$, $5-HT_{2A}$, $5-HT_6$, $5-HT_7$ and dopamine $D_{2L}$ receptors. This was accomplished by displacement of respective radioligands from cloned human receptors, all stably expressed in HEK293 cells: [$^3$H]-8-OH-DPAT for $5-HT_{1A}R$, [$^3$H]-ketanserin for $5-HT_{2A}R$, and [$^3$H]-LSD for $5-HT_6R$, [$^3$H]-5-CT for $5-HT_7R$ and [$^3$H]-raclopride for $D_2R$ Cell Culture and Preparation of Cell Membranes HEK293 cells with stable expression of human serotonin $5-HT_{1A}R$, $5-HT_{2A}$, $5-HT_6$, $5-HT_{7b}R$ or dopamine $D_{2L}R$ (all prepared with the use of Lipofectamine 2000) were maintained at 37° C. in a humidified atmosphere with 5% $CO_2$ and were grown in Dulbeco's Modifier Eagle Medium containing 10% dialysed foetal bovine serum and 500 mg/ml G418 sulphate. For membranes preparations, cells were subcultured in 10 cm diameter dishes, grown to 90% confluence, washed twice with prewarmed to 37° C. phosphate buffered saline (PBS) and were pelleted by centrifugation (200 g) in PBS containing 0.1 mM EDTA and 1 mM dithiothreitol. Prior to membrane preparations pellets were stored at −80° C.

Radioligand Binding Assays

Cell pellets were thawed and homogenized in 20 volumes of assay buffer using an Ultra Turrax tissue homogenizer and centrifuged twice at 35 000 g for 20 min at 4° C., with incubation for 15 min at 37° C. in between. The composition of the assay buffers was as follows: for 5-$HT_{1A}$R: 50 mM Tris-HCl, 0.1 mM EDTA, 4 mM $MgCl_2$, 10 mM pargyline and 0.1% ascorbate; for 5-$HT_{2A}$R: 50 mM Tris-HCl, 0.1 mM EDTA, 4 mM $MgCl_2$ and 0.1% ascorbate; for 5-$HT_6$R: 50 mM Tris-HCl, 0.5 mM EDTA and 4 mM $MgCl_2$, for 5-$HT_{7b}$R: 50 mM Tris-HCl, 4 mM $MgCl_2$, 10 mM pargyline and 0.1% ascorbate; for dopamine $D_{2L}$R: 50 mM Tris-HCl, 1 mM EDTA, 4 mM $MgCl_2$, 120 mM NaCl, 5 mM KCl, 1.5 mM $CaCl_2$ and 0.1% ascorbate.

All assays were incubated in a total volume of 200 ml in 96-welt microtitre plates for 1 h at 37° C., except for 5-$HT_{1A}$R and 5-$HT_{2A}$R which were incubated at room temperature for 1 h and 1.5 h, respectively. The process of equilibration is terminated by rapid filtration through Unifilter plates with a 96-well cell harvester and radioactivity retained on the filters was quantified on a Microbeta plate reader.

For displacement studies the assay samples contained as radioligands: 1.5 nM [$^3$H]-8-OH-DPAT (135.2 Ci/mmol) for 5-$HT_{1A}$R; 2 nM [$^3$H]-Ketanserin (53.4 Ci/mmol) for 5-$HT_{2A}$R; 2 nM [$^3$H]-LSD (83.6 Ci/mmol) for 5-$HT_6$R; 0.6 nM [$^3$H]-5-CT (39.2 Ci/mmol) for 5-$HT_7$R or 2.5 nM [$^3$H]-Raclopride (76.0 Ci/mmol).

Non-specific binding is defined with 10 μM of 5-HT in 5-$HT_{1A}$R and 5-$HT_7$R binding experiments, whereas 10 μM of chlorpromazine, 10 μM of methiothepine or 1 μM of (+)butaclamol were used in 5-$HT_{2A}$R, 5-$HT_6$R and $D_{2L}$ assays, respectively. Each compound was tested in triplicate at 7-8 concentrations ($10^{-11}$-$10^{-4}$ M). The inhibition constants ($K_i$) were calculated from the Cheng-Prusoff equation (Cheng et al., 1973)

Results were Expressed as Means of at Least Three Separate Experiments.

Membrane preparation and general assay procedures for cloned receptors were adjusted to 96-microwell format based on described protocols (Bojarski et al., 1993; Paluchowska et al., 2007; Zajdel et al., 2012a; Zajdel et al., 2012b).

TABLE 1

The binding data of the library members for 5-$HT_{1A}$, 5-$HT_6$, 5-$HT_7$ and $D_2$ receptors.

| No | $K_i$ [nM][a] | | | |
|----|---------|--------|--------|--------|
|    | 5-$HT_{1A}$ | 5-$HT_6$ | 5-$HT_7$ | $D_2$ |
| 1  | 1880 | 10 | 3967 | 2257 |
| 2  | NT[b] | 98[c] | NT | NT |
| 4  | 9148 | 4 | 7890 | NT |
| 5  | 3026 | 8 | 2133 | 1437 |
| 6  | 2351 | 3 | 4989 | 1012 |
| 7  | 2675 | 7 | 3943 | 754 |
| 8  | 3006 | 5 | 9594 | 900 |
| 9  | NT | 99[c] | NT | NT |
| 10 | NT | 100[c] | NT | NT |
| 11 | 5832 | 18 | 6877 | 664 |
| 12 | 7058 | 9 | 5222 | NT |
| 13 | 5187 | 6 | 4850 | 513 |
| 14 | NT | 7 | 3816 | 1282 |
| 15 | NT | 98[c] | NT | NT |

TABLE 1-continued

The binding data of the library members for 5-$HT_{1A}$, 5-$HT_6$, 5-$HT_7$ and $D_2$ receptors.

| No | $K_i$ [nM][a] | | | |
|----|---------|--------|--------|--------|
|    | 5-$HT_{1A}$ | 5-$HT_6$ | 5-$HT_7$ | $D_2$ |
| 16 | NT | 99[c] | NT | NT |
| 17 | 6308 | 101 | 1289 | NT |
| 18 | NT | 100[c] | NT | NT |
| 19 | NT | 100[c] | NT | NT |
| 20 | NT | 99[c] | NT | NT |
| 21 | 5330 | 19 | 1421 | 2260 |
| 22 | 15230 | 4 | 18470 | 6400 |
| 23 | 19140 | 94 | 1314 | 1548 |
| 24 | NT | 95[c] | NT | NT |
| 25 | NT | 96[c] | NT | NT |
| 26 | NT | 90[c] | NT | NT |
| 27 | 298 | 11 | NT | 1129 |
| 28 | 1223 | 3 | 7901 | 7154 |
| 29 | 773 | 3 | 1794 | 1345 |
| 30 | 437 | 3 | 2797 | NT |
| 31 | 214 | 18 | 6404 | 5943 |
| 32 | 238 | 4 | 7693 | 5086 |
| 33 | 311 | 18 | 5007 | 1775 |
| 34 | NT | 12 | 1979 | 1548 |
| 35 | NT | 3 | 6389 | 2634 |
| 36 | 194 | 34 | 2265 | 13320 |
| 37 | 372 | 7 | 5252 | 7041 |
| 38 | 218 | 14 | 2388 | 4689 |
| 39 | 760 | 3 | 4139 | 2156 |

[a]$K_i$ values were calculated from three independent binding experiments with SEM ±22%
[b]NT - not tested
[c]displacement % at $10^{-6}$M

TABLE 2

The binding data of the library members for 5-$HT_{1A}$, 5-$HT_6$, 5-$HT_7$ and $D_2$ receptors.

| No | $K_i$ [nM][a] | | | |
|----|---------|--------|--------|--------|
|    | 5-$HT_{1A}$ | 5-$HT_6$ | 5-$HT_7$ | $D_2$ |
| 40 | 148 | 14 | 3258 | 2545 |
| 41 | NT[b] | 41 | 8445 | 1677 |
| 42 | NT | 97[c] | NT | NT |
| 43 | 711 | 14 | 1985 | 4012 |
| 44 | NT | 99[c] | NT | NT |
| 45 | 922 | 5 | 7807 | 6336 |
| 46 | 590 | 8 | NT | 817 |
| 47 | NT | 28 | 2958 | 1565 |
| 48 | 1473 | 16 | 8820 | 190 |
| 49 | 3258 | 17 | 3268 | 2071 |
| 51 | NT | 90[c] | NT | NT |
| 53 | 127 | 2 | 3795 | 342 |
| 54 | 519 | 2 | 3488 | 1257 |
| 55 | 640 | 2 | 8249 | 894 |
| 56 | 152 | 10 | NT | 393 |
| 58 | 211 | 36 | NT | 826 |
| 59 | 208 | <1 | 7687 | 1915 |
| 60 | 32980 | 220 | 2361 | 415 |
| 61 | 12840 | 93 | 16150 | 239 |
| 62 | 3522 | 66 | 5869 | 1466 |
| 63 | NT | 86[c] | NT | NT |
| 65 | NT | 90[c] | NT | NT |
| 67 | NT | 100[c] | NT | NT |
| 71 | NT | 98[c] | NT | NT |
| 74 | 4183 | 20 | 6461 | 4892 |
| 75 | NT | 100[c] | NT | NT |
| 76 | NT | 361 | 22270 | 14460 |
| 77 | 85360 | 188 | 27020 | 5832 |
| 78 | 456500 | 157 | 20100 | 37250 |

TABLE 2-continued

The binding data of the library members
for 5-HT$_{1A}$, 5-HT$_6$, 5-HT$_7$ and D$_2$ receptors.

| | K$_i$ [nM][a] | | | |
|---|---|---|---|---|
| No | 5-HT$_{1A}$ | 5-HT$_6$ | 5-HT$_7$ | D$_2$ |
| 79 | NT | 95 | 3425 | 1228 |
| 81 | NT | 96[c] | NT | NT |

[a]K$_i$ values were calculated from three independent binding experiments with SEM ±22%
[b]NT - not tested
[c]displacement % at 10$^{-6}$M

Example 2b—In Vitro Evaluation

Radioligand binding assays were employed for determining the affinity of the selected compounds for $\alpha_1$ receptors (Greengrass et al., 1979) in rat cerebral cortex, H$_1$ receptors (Smit et al., 1996) and 5-HT$_{2C}$ receptors (Stam et al.) expressed in HEK-293 cells, and M$_1$ receptors (Dorje et al., 1991) and D$_3$ receptors (Mackenzie et al., 1994) expressed in CHO cells, 1994). This was accomplished by displacement of respective radioligands: [$^3$H]prazosin for a$_1$R, [$^3$H]pyrilamine for H$_1$R, [$^3$H]pirenzepine for M$_1$R, [$^3$H]mesulergine for 5-HT$_{2C}$R and [$^3$H]methyl-spiperone for D$_3$R.

Non specific binding was defined with 0.5 µM prazosine in a$_1$R binding experiments and 1 µM pyrilamine in H$_1$R assays. Solutions containing 1 µM of atropine, 10 µM of RS 102221 and 10 µM of (+)butaclamol were used in M$_1$R, 5-HT$_{2C}$R and D$_3$R experiments, respectively. Each compound was tested in duplicate at 10$^{-6}$ M concentration. Results were expressed as a mean of two separate experiments (Table 3).

TABLE 3

The binding data of the library members for
$\alpha_1$, H$_1$, M$_1$, 5-HT$_{2C}$ and D$_3$ receptors.

| | % inhibition of control binding at 10$^{-6}$M | | | | |
|---|---|---|---|---|---|
| Compd | $\alpha_1$ | H$_1$ | M$_1$ | 5-HT$_{2C}$ | D$_3$ |
| 6 | 17 | NT[a] | 9 | 21 | 69 |
| 7 | 10 | 17 | −1 | 2 | 82 |
| 29 | 20 | NT | −11 | 13 | 66 |
| 30 | 16 | 41 | 15 | 11 | 57 |

[a]NT - not tested

Example 3—In Vitro Functional Activity Ago-/Antago-Nism) on Human 5-HT$_6$ Receptors The CHO-human-5HT$_6$-Aequorin assay was bought from Euroscreen, Brussels (Euroscreen, Technical dossier, Human recombinant serotonin 5-HT$_6$-A1 receptor, DNA clone and CHO AequoScreen™ recombinant cell line, catalog no.: ES-316-A, February 2003). Human-5HT$_6$-Aequorin cells express mitochondrial targeted apo-Aequorin. Cells have to be loaded with coelanterazine, in order to reconstitute active Aequorin. After binding of agonists to the human 5-HT$_6$ receptor the intracellular calcium concentration increases and binding of calcium to the apo-Aequorin/coelanterazine leads to an oxidation reaction of coelanterazine, which results in the production of apo-Aequorin, coelenteramide, CO$_2$ and light ($\lambda_{max}$ 469 nm). This luminescent response is dependent on the agonist concentration. Luminescence is measured using the MicroBeta Jet (Perkin Elmer). Agonistic effects of compounds are expressed as pEC$_{50}$. Antagonistic effects of compounds were determined as inhibition of 10$^{-6}$ M $\alpha$-methylserotonin induced luminescence and the pA$_2$ was calculated according to Cheng-Preushoff equation. Compounds were tested at 2 independent experiment were performed in duplicate.

TABLE 4

The agonist and antagonist
effect of the selected library members.

| Compound | % inhibition of control agonist response | % inhibition of control antagonist response |
|---|---|---|
| 5 | −2.0 | 93.7 |
| 6 | 13.6 | 92.5 |
| 7 | 0.8 | 85.9 |
| 8 | 9.6 | 80.8 |
| 11 | 4.8 | 51.8 |
| 13 | 6.5 | 68.8 |
| 14 | 10.8 | 88.8 |
| 21 | 10.6 | 60.0 |
| 22 | 16.4 | 70.2 |
| 29 | 5.1 | 99.8 |
| 30 | 1.2 | 91.6 |
| 32 | 4.3 | 84.3 |
| 34 | −2.1 | 71.4 |
| 35 | 1.2 | 90.1 |
| 38 | 7.0 | 61.3 |
| 39 | 8.9 | 89.0 |
| 40 | −5.2 | 65.3 |
| 43 | 2.4 | 94.7 |
| 45 | 7.8 | 75.8 |
| 48 | 2.7 | 37.7 |
| 54 | 2.8 | 89.6 |
| 55 | 7.8 | 82.8 |
| 57 | 1.5 | 97.3 |
| 59 | 16.9 | 61.0 |
| 76 | 22.2 | 11.6 |
| 78 | 21.3 | 23.8 |

TABLE 5

The intrinsic activity for 5-HT$_6$
receptors of selected library member.

| Compound | IC$_{50}$ [nM] | K$_B$ [nM] |
|---|---|---|
| 29 | 32 | 5 |
| methiothepin | 18 | 2.8 |

Example 4—Formulation Used in In Vivo Animal Experiments

For intraperitoneal (i.p.) administration: to the desired quantity of the solid compound in a glass beaker, required volume of sterile water for injection was added and swirled with glass bar until complete dissolution of the compound.

Example 5—Forced Swim Test (FST) in Wistar Rats

Animals.

Male Wistar rats weighing 220-250 g were used in the test. The animals were housed in polycarbonate Makrolon type 3 cages (dimensions 26.5×15×42 cm) in groups of four. All animals were kept in an environmentally controlled rooms (ambient temperature 22±2° C.; relative humidity 50-60%; 12:12 light:dark cycle, lights on at 8:00). They were allowed to acclimatize with the environment for one week before commencement of the experiments. Standard laboratory food (Ssniff M-Z) and filtered water were freely available. The experiments were conducted in the light phase between 09.00 and 14.00 hours. 1 h before the start of the experiment, rats were transferred to the experimental room for acclimation.

Apparatus and Procedure.

The experiment was carried out according to the method of Porsolt et al. (1978). On the first day of experiment, the animals were gently individually placed in Plexiglas cylinders (40 cm high, 18 cm in diameter) containing 15 cm of water maintained at 25° C. for 15 min. Upon removal from water, the rats were placed in a Plexiglas box for 30 min under a 60-W bulb to dry off. On the following day, the rats were placed again in the cylinder and the total duration of immobility was recorded throughout the 5-min test period. Fresh water was used for each animal.

Experimental Design.

The compounds were administered IP, 60 minutes before the test.

Drugs.

The experimental compounds were dissolved in the distilled water. All compounds were administered in the volume of 2 ml/kg.

Example 6—Conflict Drinking Test (Vogel Test) in Wistar Rats

Animals.

Male Wistar rats weighing 220-250 g were used in the test. The animals were housed in polycarbonate Makrolon type 3 cages (dimensions 26.5×15×42 cm) in groups of four. All animals were kept in an environmentally controlled rooms (ambient temperature 22±2° C.; relative humidity 50-60%; 12:12 light:dark cycle, lights on at 8:00). They were allowed to acclimatize with the environment for one week before commencement of the experiments. Standard laboratory food (Ssniff M-Z) and filtered water were freely available. The experiments were conducted in the light phase between 09.00 and 14.00 hours. 1 h before the start of the experiment, rats were transferred to the experimental room for acclimation.

Apparatus and Procedure.

A modification of the method of Vogel et al. (1971) was employed using Anxiety Monitoring System "Vogel test" produced by TSE Systems. It was consisted of polycarbonate cages (dimensions 26.5×15×42 cm), equipped with a grid floor made from stainless steel bars and drinking bottles containing tap water. Experimental chambers were connected to PC software by control chassis and electric shocks' generator. On the first day of the experiment, the rats were adapted to the test chambers for 10 min. After the adaptation period, the animals were deprived of water for 24 h and were then placed in the test chambers for another 10-min adaptation period during which they had free access to the drinking bottles. Afterwards, they were allowed a 30-min free-drinking session in their home cages. After another 24-h water deprivation period, the rats were placed again in the test chambers. Recording data started immediately after the first lick and every 20 licks rats were punished with an electric shock (0.5 mA, lasting 1 s). The impulses were released via the spout of the drinking bottles. If a rat was drinking when an impulse was released, it received a shock. The number of licks and the number of shocks received during a 5-min experimental session was recorded automatically.

Experimental Design.

The compounds were administered IP, 60 minutes before the test.

Drugs.

The experimental compounds were dissolved in the distilled water. All compounds were administered in the volume of 2 ml/kg.

Example 7—Novel Object Recognition (NOR) Test in Sprague-Dawley Rats

Animals.

Male Sprague-Dawley rats (Charles River, Germany) weighing ~250 g at the arrival were housed in the standard laboratory cages, under standard colony A/C controlled conditions: room temperature 21±2° C., humidity (40-50%), 12-hr light/dark cycle (lights on: 06:00) with ad libitum access to food and water. Rats were allowed to acclimatize for at least 7 days before the start of the experimental procedure. During this week animals were handled for at least 3 times. Behavioral testing was carried out during the light phase of the light/dark cycle. At least 1 h before the start of the experiment, rats were transferred to the experimental room for acclimation.

Apparatus and Procedure.

Rats were tested in a dimly lit (25 lx) "open field" apparatus made of a dull gray plastic (66×56×30 cm). After each measurement, the floor was cleaned and dried.

The procedure lasting for 2 days consisted of the habituation to the test arena (without any objects) for 5 min. The test session comprising of two trials separated by an intertrial interval (ITI) of 1 h was carried out on the next day.

During the first trial (familiarization, T1) two identical objects (A1 and A2) were presented in the opposite corners of the open field, approximately 10 cm from the walls. During the second trial (recognition, T2) one of the A objects was replaced by a novel one, so that the animals were presented with the A=familiar and B=novel objects. Both trials lasted for 3 min and the animals were returned to their home cages after T1.

The objects used were the glass beakers filled with the gravel and the plastic bottles filled with the sand. The heights of the objects were comparable (~12 cm) and the objects were heavy enough not to be displaced by the animals.

The sequence of presentations and the location of the objects was randomly assigned to each rat. By definition, animals explored the objects when looking, licking, sniffing or touching the object white sniffing, but not when leaning against, standing or sitting on the object.

Any rat exploring the two objects for less than 5 s within 3 min of T1 or T2 was eliminated from the study. Exploration time of the objects and the distance traveled were measured using the Any-Maze® video tracking system. Based on exploration time (E) of two objects during T2, discrimination index (DI) was calculated according to the formula:

$$DI=(E_B-E_A)/(E_A+A_B).$$

Experimental Design.

Phencyclidine (PCP), used to attenuate learning, was administered at the dose of 5 mg/kg (IP) 45 min before familiarization phase (T1). The compounds were administrated IP, 1 hour and 15 min before T1.

Drugs.

Phencyclidine hydrochloride (Sigma-Aldrich) and the experimental compounds were dissolved in the distilled water. All compounds were administered in the volume of 1 ml/kg.

TABLE 6

Results of behavioral evaluation of the selected compounds.

| Pharmacological model | Compd 6 | Compd 7 | Compd 10 | Compd 29 | Compd 30 | Compd 42 |
|---|---|---|---|---|---|---|
| | Minimum effective dose (mg/kg) | | | | | |
| Forced swim test in rats (potential antidepressant properties) | 10 | 3 | NT | >10 | 10 | 0.1 |
| Conflict drinking (Vogel test) in rats (potential anxiolytic properties) | 3 | 10 | 10 | 10 | 10 | 3 |
| | Tested and active doses (mg/kg) | | | | | |
| Novel object recognition test in rats (potential procognitive properties) | 1 and 3 | 1 and 3 | NT | 1 and 3 | 1 and 3 | NT |

Results of the behavioral tests, i.e. forced swim test and conflict drinking test in rats, described in Examples 8 and 9 confirm potential activity of the compounds of invention in therapy of depression and/or anxiety. In the forced swim test, a reference antidepressant drug imipramine was effective after administration of a dose of 15 mg/kg increasing the climbing time. SB-271046 (selective 5-HT$_6$ receptor antagonist) displayed it's antidepressant-like activity at dose of 10 mg/kg. In the conflict drinking test (Vogel test) in rats all the investigated compounds as well as SB-271046 were active at a dose of ≤10 mg/kg increasing the number of licks and the number of shocks received. By comparison diazepam, used as a reference anxiolytic drug, was effective in doses of 5-10 mg/kg Results of the behavioral NOR test in rats, described in Example 10 confirm the potential pro-cognitive activity of the compounds in the therapy of psychiatric disorders like schizophrenia, affective disorders and neurodegenerative diseases. This is because all four compounds tested reduced PCP-induced cognitive deficits at the doses of 1 and 3 mg/kg. SB-271046, used as a reference compound, was effective against PCP-induced deficit also at the dose of 1 mg/kg.

CITED LITERATURE

1. Benakki, H.; Colacino, E.; André, C.; Guenoun, F.; Martinez, J.; Lamaty, F. *Tetrahedron*, 2008, 64, 5949-5955.
2. Bentley, J. C.; Bourson, A.; Boess, F. G.; Fone, K. C.; Marsden, C. A.; Petit, N.; Sleight, A. J. *Br. J. Pharmacol.* 1999, 126, 1537-1542.
3. Berge, S. M.; Bighley, L. D.; Monkhause, D. C. *J. Pharm. Sci.* 1977, 66, 1-19.
4. Boissier J R, Simon P, Aron C. *Eur. J. Pharmacol.* 1968, 4, 145-151.
5. Bojarski, A. J.; Cegta, M. T.; Charakchieva-Minol, S.; Mokrosz, M. J.; Maćkowiak, M.; Misztal, S.; Mokrosz, J. L. *Pharmazie* 1993, 48, 289-294.
6. Brown, T. H.; Ife, R. I.; Keeling, D. J.; Laing, S. M.; Leach, C. A., Parsons, M. E.; Price, C. A.; Reavill, D. R.; Wiggal, K. J. *J. Med. Chem.* 1990, 33, 527-533.
7. Cheng, Y.; Prusoff, W. H. *Biochem Pharmacol.* 1973, 22, 3099.
8. Cole, D. C.; Kelly, M. G.; Bravo, B. A.; Palmer, Y. L. US Patent 2003232843, 2003.
9. Dawson, L. A.; Nguyen, H. Q.; Li, P. *Neuropsychopharmacology*, 2001, 25, 662-668.
10. Dorje, F.; Wess, J.; Lambrecht, G.; Tacke, R.; Mutschler, E.; Brann, M. R. *J. Pharmacol. Exp. Theor.* 1991, 256, 727-733.
11. Dwyer, F. P.; Sargeson, A. M.; James, L. B. *J. Am. Chem. Soc.* 1964, 86, 590-592.
12. Gérard, C.; Martres, M. P.; Lefèvre, K.; Miguel, M. C.; Vergé, D.; Lanfumey, L.; Doucet, E.; Hamon, M.; el Mestikawy, S. *Brain. Res.* 1997, 746, 207-219
13. Greengrass, P.; Bremmer, R. *Eur. J. Pharmacol.* 1979, 55, 323-326.
14. Hannon, J.; Hoyer, D. *Behav. Brain Res.* 2008, 195, 198-213.
15. Heal, D. J.; Smith, S. L.; Fisas, A.; Codony, X.; Buschmann, H. *Pharmacol. Ther.* 2008, 117, 207.
16. Heidempergher, F.; Pavarello, P.; Pillan, A.; Pinciroli, V.; Torre, A. D.; Speciale, C.; Marconi, M.; Cini, M.; Toma, S.; Greco, F.; Varasi, M. *Il Farmaco*, 1999, 54, 152-160.
17. Helissey, P.; Parrot-Lopez, H.; Renault, J.; Cross, S. *Eur. J. Med. Chem.* 1987, 22, 366-368.
18. Hirano, K.; Piers, T. M.; Searle, K. M.; Miller, N. D.; Rutter, R.; Chapman, P. F. *Life Sci.* 2009, 84, 558-562.
19. Hoyer, D.; Hannon, J. *Pharmacol. Biochem. Beh.*, 2002, 71, 533-554.
20. King, M. W.; Sleight, A. J.; Wolley, M. L.; Topham, I. A.; Marsden, C. A.; Fone, K. C. F. *Neuropharmacology*, 2004, 47, 195-204.
21. Kohen, R.; Metclaf, M. A.; Khan, N.; Druck, T.; Huebner, K.; Lachowicz, J. E.; Meltzer, H. Y.; Sibley, D. R.; Roth, B. L.; Hamblin, M. W. *J. Neurochem.* 1996, 66, 47.
22. López-Rodriguez, M. L.; Benhamú, B.; de la Fuente, T.; Sanz, A.; Pardo, L.; Campillo, M.; *J. Med. Chem.* 2005, 48, 4216.
23. MacKenzie, R. G.; VanLeeuwen, D.; Pugsley, T. A.; Shih, Y-H.; Demaltos, S.; Tang, L.; Todd, R. D.; O'Malley, K. L. *Eur. J. Pharmacol.* 1994, 266, 79-85.
24. Martin, C. M.; Dyson, P. J.; Ingham, S. L.; Johnson, B. F. G.; Blake, A. J. *Chem. Soc. Dalton Trans.* 1995, 2741-2748.
25. Mitchell, E.; Neumaier, J. F. *Pharmacol. Ther.* 2005, 108, 320.
26. Monsma, F. J., Jr.; Shen, Y.; Ward, R. P.; Hamblin, M. W.; Simbley, D. R. *Mol. Pharmacol.* 1993, 43, 320-327.
27. Paluchowska, M. H.; Bugno, R.; Tatarczyńska, E.; Nikiforuk, A.; Lenda, T.; Chojnacka-Wójcik, E. *Bioorg. Med. Chem.* 2007, 15, 7116.
28. Porsolt, R. D.; Bertin, A.; Jelfre, M. *Arch. Int. Pharmacodyn. Ther.* 1977, 229, 327-336.
29. Pouzet, B.; Didriksen, M.; Arnt, J. *Pharmacol. Biochem. Behav.* 2002, 71, 634-643.

30. Pullagurla, M. R.; Westkaemper, R. B.; Glennon, R. A. *Bioorg. Med. Chem. Lett.* 2004, 14, 4569.
31. Riemer, C.; Borroni, E.; Levet-Trafit, B.; Martin, J. R.; Poli, S.; Porter, R. H.; Bös, M. *J. Med. Chem.* 2003, 46, 1273-1276.
32. Rodefer, S. J.; Nguyen, T. N.; Karlsson, J. J.; Arnt, J. *Neuropschopharmacology,* 2008, 33, 2657-2666.
33. Rogers, D. C.; Hagan, J. J.; *Psychopharmacology,* 2001, 158, 114-119.
34. Ruat, M.; Traiffort, E.; Arrang, J. M.; Tardivel-Lacombe, J.; Diaz, J.; Leurs, R.; Schwartz, J. C. *Biochem. Biophys. Res. Commun.* 1993, 193, 268-276.
35. Schechter, L. E.; Smith, D. L.; Li, P.; Lin, Q.; *Soc. Neurosci. Meet,* 2004, 394, 11.
36. Schoeffter, P.; Waeber, C.; *Naudyn-Schmied. Arch. Pharmacol.* 1994, 350, 356-360.
37. Smit, M. J; Timmerman, H.; Hijzlelendoorn, J. C.; Fukui, H.; Leurs, R.; *Brit. J. Pharmacol.* 1996, 117, 1071-1080.
38. Stam, N. J.; Vanderheyden, P.; van Alebeek, C.; Klomp, J.; de Boer, T.; van Delft, A. M.; Olijve, W. *Eur. J. Pharmacol.* 1994, 269, 339-348.
39. Upton, N.; Chuang, T. T.; Hunter, A. J.; Virley, D. J. *Neurotherapeutics* 2008, 5, 458.
40. Ward, R. P.; Hamblin, M. W.; Lachowicz, J. E.; Hoffman, B. J.; Sibley, B. R.; Dorsa, D. M. *Neuroscience* 1995, 64, 1105.
41. Wesołowska, A.; Nikiforuk, A. *Behav. Pharmacol.,* 2007a, 18, 439-46.
42. Wesołowska, A.; Nikiforuk, A. *Neuropharmacology,* 2007b, 52, 1274-1283.
43. Wright, G. C.; Watson, E. J.; Ebetino, F. F.; Lougheed, G.; Stevenson, B. F.; Winterstein, A.; Bickerton, R. K.; Halliday, R. P.; Pals, D. T. *J. Med. Chem.* 1971, 14, 1060-1066.
44. Zajdet P.; Kurczab R; Grychowska K.; Satata G.; Pawtowski M.; Bojarski A. J., *Eur. J. Med. Chem.,* 2012a, 56, 348-60.
45. Zajdel, P.; Marciniec, K.; Maślankiewicz, A.; Satata, G.; Duszyńska, B.; Bojarski, A. J.; Partyka, A.; Jastrzębska-Więsek, M.; Wróbel, D.; Wesołowska, A.; Pawtowski, M. Bioorg. *Med. Chem.,* 2012b, 20, 1545-1556.

The invention claimed is:

1. A compound of the general formula (XIV):

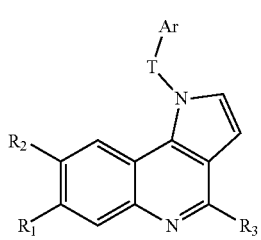

XIV or a tautomer, stereoisomer, N-oxide, isotopically-labelled analogue, or a pharmacologically acceptable salt, hydrate or solvate thereof, wherein:

$R_1$ and $R_2$ are independently selected from the group consisting of hydrogen, an unsubstituted alkyl($C_1$-$C_3$) group, an alkyl($C_1$-$C_3$) group substituted with one or more halogen atoms, an alkoxyl($C_1$-$C_3$) group, cyano, nitro, amino, and hydroxyl;

T is CO, $CH_2$, substituted alkyl($C_1$-$C_2$) group, SO, or $SO_2$;

Ar is unsubstituted aryl (5-6 membered), biaryl (8-10 membered), heteroaryl (5-6 membered), heteroaryl (8-10 membered) having 1-3 heteroatoms independently selected from the group consisting of N, O, S, optionally substituted with one or more substituents selected from alkyl($C_1$-$C_3$) group, an alkyl($C_1$-$C_3$) group substituted with one or more halogen atoms, alkoxy($C_1$-$C_3$) group, alkenyl($C_2$-$C_4$), halogen, nitro, hydroxyl, cyano, amino, alkylamino, carboxamide;

$R_3$ is a substituent selected from the group consisting of cyclic or linear substituted or unsubstituted groups of structures XV-XVIII:

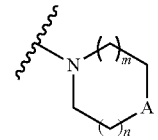

XV

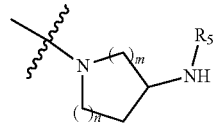

XVII

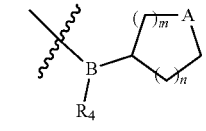

XVI

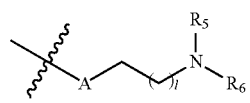

XVIII wherein:
A is NH, O, $CH_2$, or $NR_5$;
B—$R_4$ is NH, O or $NR_7$;
$R_7$ is hydrogen atom or alkyl($C_1$-$C_3$) group;
$R_5$ is alkyl($C_1$-$C_3$) group or benzyl;
$R_6$ is alkyl($C_1$-$C_3$) group;
n is 0, 1, or 2;
m is 0, 1, or 2;
l is 1 or 2.

2. The compound as claimed in claim 1, wherein:
$R_1$ and $R_2$ are independently selected from the group consisting of hydrogen, a methyl group optionally substituted with one or more halogen atoms, an ethyl group optionally substituted with one or more halogen atoms, cyano, nitro, amino, hydroxyl, and methoxyl;
T is CO, $CH_2$, substituted alkyl($C_1$-$C_2$) group, or $SO_2$;
Ar is unsubstituted aryl (5-6 membered), biaryl (8-10 membered), heteroaryl (8-10 membered) having 1-3 heteroatoms independently selected from the group consisting of N, O, S, optionally substituted with one or more substituents selected from alkyl($C_1$-$C_3$) group, an alkyl($C_1$-$C_3$) group substituted with one or more halogen atoms, methoxy, ethoxy, halogen, nitro, hydroxyl, cyano, amino, alkylamino, carboxamide;
B—$R_4$ is NH or O.

3. The compound as claimed in claim 1, selected from the group consisting of:
N1,N1-dimethyl-N2-(1-(phenylsulfonyl)-1H-pyrrolo[3,2-c]quinolin-4-yl)ethane-1,2-diamine;

1-((3-chlorophenyl)sulfonyl)-N-(azetidin-3-yl)-1H-pyrrolo[3,2-c]quinolin-4-amine;
1-(naphthalen-1-ylsulfonyl)-N-(azetidin-3-yl)-1H-pyrrolo[3,2-c]quinolin-4-amine;
1-(phenylsulfonyl)-N-(pyrrolidin-3-yl)-1H-pyrrolo[3,2-c]quinolin-4-amine;
1-((3-chlorophenyl)sulfonyl)-N-(pyrrolidin-3-yl)-1H-pyrrolo[3,2-c]quinolin-4-amine;
(S)-1-((3-chlorophenyl)sulfonyl)-N-(pyrrolidin-3-yl)-1H-pyrrolo[3,2-c]quinolin-4-amine;
(R)-1-((3-chlorophenyl)sulfonyl)-N-(pyrrolidin-3-yl)-1H-pyrrolo[3,2-c]quinolin-4-amine;
1-((3-fluorophenyl)sulfonyl)-N-(pyrrolidin-3-yl)-1H-pyrrolo[3,2-c]quinolin-4-amine;
(S)-1-((3-fluorophenyl)sulfonyl)-N-(pyrrolidin-3-yl)-1H-pyrrolo[3,2-c]quinolin-4-amine;
(R)-1-((3-fluorophenyl)sulfonyl)-N-(pyrrolidin-3-yl)-1H-pyrrolo[3,2-c]quinolin-4-amine;
1-((4-fluorophenyl)sulfonyl)-N-(pyrrolidin-3-yl)-1H-pyrrolo[3,2-c]quinolin-4-amine;
1-((2,5-difluorophenyl)sulfonyl)-N-(pyrrolidin-3-yl)-1H-pyrrolo[3,2-c]quinolin-4-amine;
1-((3-methoxyphenyl)sulfonyl)-N-(pyrrolidin-3-yl)-1H-pyrrolo[3,2-c]quinolin-4-amine;
1-((3-(trifluoromethyl)phenyl)sulfonyl)-N-(pyrrolidin-3-yl)-1H-pyrrolo[3,2-c]quinolin-4-amine;
(S)-1-((3-(trifluoromethyl)phenyl)sulfonyl)-N-(pyrrolidin-3-yl)-1H-pyrrolo[3,2-c]quinolin-4-amine;
(R)-1-((3-(trifluoromethyl)phenyl)sulfonyl)-N-(pyrrolidin-3-yl)-1H-pyrrolo[3,2-c]quinolin-4-amine;
1-((4-(tert-butyl)phenyl)sulfonyl)-N-(pyrrolidin-3-yl)-1H-pyrrolo[3,2-c]quinolin-4-amine;
1-((4-aminophenyl)sulfonyl)-N-(pyrrolidin-3-yl)-1H-pyrrolo[3,2-c]quinolin-4-amine;
(S)-1-((4-aminophenyl)sulfonyl)-N-(pyrrolidin-3-yl)-1H-pyrrolo[3,2-c]quinolin-4-amine;
(R)-1-((4-aminophenyl)sulfonyl)-N-(pyrrolidin-3-yl)-1H-pyrrolo[3,2-c]quinolin-4-amine;
1-(naphthalen-1-ylsulfonyl)-N-(pyrrolidin-3-yl)-1H-pyrrolo[3,2-c]quinolin-4-amine;
1-(quinolin-8-ylsulfonyl)-N-(pyrrolidin-3-yl)-1H-pyrrolo[3,2-c]quinolin-4-amine;
1-((5-methylbenzo[b]thiophen-2-yl)sulfonyl)-N-(pyrrolidin-3-yl)-1H-pyrrolo[3,2-c]quinolin-4-amine;
7-fluoro-1-((3-chlorophenyl)sulfonyl)-N-(pyrrolidin-3-yl)-1H-pyrrolo[3,2-c]quinolin-4-amine;
8-chloro-1-((3-chlorophenyl)sulfonyl)-N-(pyrrolidin-3-yl)-1H-pyrrolo[3,2-c]quinolin-4-amine;
N-methyl-1-(1-(phenylsulfonyl)-1H-pyrrolo[3,2-c]quinolin-4-yl) pyrrolidin-3-amine;
1-(phenylsulfonyl)-4-(piperazin-1-yl)-1H-pyrrolo[3,2-c]quinoline;
1-((2-bromophenyl)sulfonyl)-4-(piperazin-1-yl)-1H-pyrrolo[3,2-c]quinoline;
1-((3-chlorophenyl)sulfonyl)-4-(piperazin-1-yl)-1H-pyrrolo[3,2-c]quinoline;
1-((3-fluorophenyl)sulfonyl)-4-(piperazin-1-yl)-1H-pyrrolo[3,2-c]quinoline;
1-((4-fluorophenyl)sulfonyl)-4-(piperazin-1-yl)-1H-pyrrolo[3,2-c]quinoline;
1-((2,5-difluorophenyl)sulfonyl)-4-(piperazin-1-yl)-1H-pyrrolo[3,2-c]quinoline;
1-((3,4-difluorophenyl)sulfonyl)-4-(piperazin-1-yl)-1H-pyrrolo[3,2-c]quinoline;
1-((3,4-dichlorophenyl)sulfonyl)-4-(piperazin-1-yl)-1H-pyrrolo[3,2-c]quinoline;
1-((3-(trifluoromethyl)phenyl)sulfonyl)-4-(piperazin-1-yl)-1H-pyrrolo[3,2-c]quinoline;
1-((4-(trifluoromethyl)phenyl)sulfonyl)-4-(piperazin-1-yl)-1H-pyrrolo[3,2-c]quinoline;
1-((3-methoxyphenyl)sulfonyl)-4-(piperazin-1-yl)-1H-pyrrolo[3,2-c]quinoline;
1-((3-cyanophenyl)sulfonyl)-4-(piperazin-1-yl)-1H-pyrrolo[3,2-c]quinoline;
1-((3-methylphenyl)sulfonyl)-4-(piperazin-1-yl)-1H-pyrrolo[3,2-c]quinoline;
1-((4-isopropylphenyl)sulfonyl)-4-(piperazin-1-yl)-1H-pyrrolo[3,2-c]quinoline;
1-((4-(tert-butyl)phenyl)sulfonyl)-4-(piperazin-1-yl)-1H-pyrrolo[3,2-c]quinoline;
1-(4-(aminophenyl)sulfonyl)-4-(piperazin-1-yl)-1H-pyrrolo[3,2-c]quinoline;
1-(naphthalen-1-ylsulfonyl)-4-(piperazin-1-yl)-1H-pyrrolo[3,2-c]quinoline;
1-(naphthalen-2-ylsulfonyl)-4-(piperazin-1-yl)-1H-pyrrolo[3,2-c]quinoline;
1-(quinolin-8-ylsulfonyl)-4-(piperazin-1-yl)-1H-pyrrolo[3,2-c]quinoline;
1-((5-chlorothiophen-2-yl)sulfonyl)-4-(piperazin-1-yl)-1H-pyrrolo[3,2-c]quinoline;
1-((5-methylbenzo[b]thiophen-2-yl)sulfonyl)-4-(piperazin-1-yl)-1H-pyrrolo[3,2-c]quinoline;
1-((5-chloro-3-methylbenzo[b]thiophen-2-yl)sulfonyl)-4-(piperazin-1-yl)-1H-pyrrolo[3,2-c]quinoline;
1-(3-chlorobenzyl)-4-(piperazin-1-yl)-1H-pyrrolo[3,2-c]quinoline;
1-(3-fluorobenzyl)-4-(piperazin-1-yl)-1H-pyrrolo[3,2-c]quinoline;
(3-chlorophenyl)-(4-(piperazin-1-yl)-1H-pyrrolo[3,2-c]quinolin-1-yl)methanone;
(3-methylphenyl)-(4-(piperazin-1-yl)-1H-pyrrolo[3,2-c]quinolin-1-yl) methanone;
1-(phenylsulfonyl)-4-(4-methylpiperazin-1-yl)-1H-pyrrolo[3,2-c]quinoline;
1-((3-chlorophenyl)sulfonyl)-4-(4-methylpiperazin-1-yl)-1H-pyrrolo[3,2-c]quinoline;
1-((3-fluorophenyl)sulfonyl)-4-(4-methylpiperazin-1-yl)-1H-pyrrolo[3,2-c]quinoline;
1-((4-fluorophenyl)sulfonyl)-4-(4-methylpiperazin-1-yl)-1H-pyrrolo[3,2-c]quinoline;
1-((4-aminophenyl)sulfonyl)-4-(4-methylpiperazin-1-yl)-1H-pyrrolo[3,2-c]quinoline;
1-(naphthalen-1-ylsulfonyl)-4-(4-methylpiperazin-1-yl)-1H-pyrrolo[3,2-c]quinoline;
1-(quinolin-8-ylsulfonyl)-4-(4-methylpiperazin-1-yl)-1H-pyrrolo[3,2-c]quinolone;
1-(phenylsulfonyl)-4-(4-benzylpiperazin-1-yl)-1H-pyrrolo[3,2-c]quinoline;
1-((5-chlorothiophen-2-yl)sulfonyl)-4-(4-benzylpiperazin-1-yl)-1H-pyrrolo[3,2-c]quinoline 41-1-(quinolin-8-ylsulfonyl)-4-(4-benzylpiperazin-1-yl)-1H-pyrrolo[3,2-c]quinoline;
8-nitro-1-((4-isopropylphenyl)sulfonyl)-4-(piperazin-1-yl)-1H-pyrrolo[3,2-c]quinoline;
8-nitro-1-((3-(trifluoromethyl)phenyl)sulfonyl)-4-(piperazin-1-yl)-1H-pyrrolo[3,2-c]quinoline;
8-amino-1-((3,4-dichlorophenyl)sulfonyl)-4-(piperazin-1-yl)-1H-pyrrolo[3,2-c]quinoline;
8-carbonitrile-1-(3-methylphenyl)-4-(piperazin-1-yl)-1H-pyrrolo[3,2-c]quinoline;
8-carbonitrile-1-(naphthalen-1-ylsulfonyl)-4-(piperazin-1-yl)-1H-pyrrolo[3,2-c]quinoline;

8-methoxy-1-((3-(trifluoromethyl)phenyl)sulfonyl)-4-(piperazin-1-yl)-1H-pyrrolo[3,2-c]quinoline;
8-methoxy-1-((3-fluorophenyl)sulfonyl)-4-(piperazin-1-yl)-1H-pyrrolo[3,2-c]quinoline;
8-chloro-1-((3-chlorophenyl)sulfonyl)-4-(piperazin-1-yl)-1H-pyrrolo[3,2-c]quinoline;
8-chloro-1-(naphthalen-1-ylsulfonyl)-4-(piperazin-1-yl)-1H-pyrrolo[3,2-c]quinoline;
7-fluoro-1-((3-methylphenyl)sulfonyl)-4-(piperazin-1-yl)-1H-pyrrolo[3,2-c]quinoline;
7-fluoro-1-((3-chlorophenyl)sulfonyl)-4-(piperazin-1-yl)-1H-pyrrolo[3,2-c]quinoline;
1-((3,4-difluorophenyl)sulfonyl)-4-(1,4-diazepan-1-yl)-1H-pyrrolo[3,2-c]quinoline;
1-((3-chlorophenyl)sulfonyl)-4-(1,4-diazepan-1-yl)-1H-pyrrolo[3,2-c]quinoline;
1-((3-chlorophenyl)sulfonyl)-4-(piperidin-1-yl)-1H-pyrrolo[3,2-c]quinoline;
1-(quinolin-8-ylsulfonyl)-4-(piperidin-1-yl)-1H-pyrrolo[3,2-c]quinoline;
1-((3-chlorophenyl)sulfonyl)-4-(morpholine-4-yl)-1H-pyrrolo[3,2-c]quinoline;
1-(quinolin-8-ylsulfonyl)-4-(morpholine-4-yl)-1H-pyrrolo[3,2-c]quinoline;
1-((3-methylphenyl)sulfonyl)-4-(pyrrolidin-3-yloxy)-1H-pyrrolo[3,2-c]quinoline; and
1-((2,5-difluorophenyl)sulfonyl)-4-(pyrrolidin-3-yloxy)-1H-pyrrolo[3,2-c]quinoline.

4. The compound as claimed in claim 1, said compound being an optically active enantiomer.

5. A pharmaceutical composition comprising:
a compound according to claim 1, and
a pharmaceutically acceptable carrier or diluent.

6. A pharmaceutical composition comprising:
a compound according to claim 4, and
a pharmaceutically acceptable carrier or diluent.

7. The composition of claim 5, further comprising at least one additional therapeutic agent.

8. A process to prepare the compound of the general formula (XIV) according to claim 1, comprising:
reacting a substituted pyrroloquinolines of formula XIX

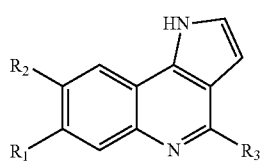

XIX with an arylsulfonyl halide, arylacyl halide, or arylalkyl halide of formula Ar-T-X, where X is halogen, in the presence of a base to yield the compound of the general formula (XIV),
wherein $R_1$, $R_2$, $R_3$, T, and Ar are as defined in claim 1.

9. The process of claim 8, wherein the substituted pyrroloquinolines of formula XIX is prepared by:
a) Converting a lactam of formula A-6 into a compound of formula A-7

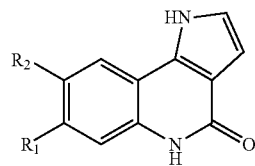

A-6

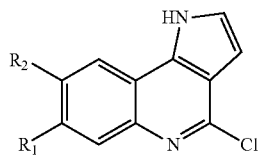

A-7 by treating the lactam of formula A-6 with a chlorinating agent at an elevated temperature; and
b) Preparing a substituted pyrroloquinolines of formula XIX

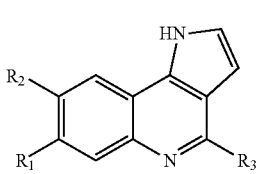

XIX by reacting the compound of formula A-7 with an amine or alcohol of formula H—$R_3$,
wherein $R_1$, $R_2$, and $R_3$ are as defined in claim 8.

10. The process of claim 9, wherein the chlorinating agent is selected from the group consisting of $POCl_3$, $SOCl_2$, $PCl_5$, and mixtures thereof.

11. The process of claim 8, wherein said reacting the compound of formula A-7 is carried out in the presence of microwave radiation.

12. The process of claim 8, wherein the base is a strong base or a phosphazene base.

13. A method of treatment of anxiety, depression or a combination thereof, said method comprising administering to a patient in need of such treatment a therapeutically effective amount of a compound as defined in claim 1.

14. A method of treatment of anxiety, depression or a combination thereof, said method comprising administering to a patient in need of such treatment a therapeutically effective amount of a compound as defined in claim 4.

15. The method of claim 13, wherein the method treats anxiety.

16. The method of claim 13, wherein:
the compound of formula XIV is administered in combination with a second medicament;
said compound of formula XIV and said second medicament being administered simultaneously or sequentially to said patient.

17. The method of claim 13, wherein the method treats depression.

* * * * *